United States Patent
Faas McKnight et al.

(10) Patent No.: US 9,180,186 B2
(45) Date of Patent: Nov. 10, 2015

(54) BIOMARKERS OF IMMUNOMODULATORY EFFECTS IN HUMANS TREATED WITH ANTI-CD200 ANTIBODIES

(75) Inventors: Susan Faas McKnight, Old Lyme, CT (US); Roxanne Cofiell, Glastonbury, CT (US); Yan Yan, Cheshire, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 507 days.

(21) Appl. No.: 13/521,671

(22) PCT Filed: Jan. 11, 2011

(86) PCT No.: PCT/US2011/020750
§ 371 (c)(1),
(2), (4) Date: Apr. 17, 2013

(87) PCT Pub. No.: WO2011/085343
PCT Pub. Date: Jul. 14, 2011

(65) Prior Publication Data
US 2013/0202602 A1    Aug. 8, 2013

Related U.S. Application Data

(60) Provisional application No. 61/294,066, filed on Jan. 11, 2010, provisional application No. 61/337,997, filed on Feb. 11, 2010, provisional application No. 61/401,442, filed on Aug. 12, 2010, provisional application No. 61/416,974, filed on Nov. 24, 2010.

(51) Int. Cl.
| | |
|---|---|
| *A61K 39/395* | (2006.01) |
| *C07K 16/28* | (2006.01) |
| *G01N 33/50* | (2006.01) |
| *G01N 33/53* | (2006.01) |
| *G01N 33/574* | (2006.01) |
| *G01N 33/68* | (2006.01) |
| *A61K 39/00* | (2006.01) |

(52) U.S. Cl.
CPC ....... *A61K 39/39558* (2013.01); *C07K 16/2803* (2013.01); *G01N 33/5094* (2013.01); *G01N 33/57484* (2013.01); *G01N 33/68* (2013.01); *A61K 2039/505* (2013.01); *A61K 2039/545* (2013.01); *A61K 2039/57* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,403,484 A | 4/1995 | Ladner et al. |
| 5,595,721 A | 1/1997 | Kaminski et al. |
| 6,338,851 B1 | 1/2002 | Gorczynski |
| 6,652,858 B2 | 11/2003 | Gorczynski et al. |
| 6,749,854 B2 | 6/2004 | Gorczynski et al. |
| 6,955,811 B2 | 10/2005 | Gorczynski et al. |
| 6,984,625 B2 | 1/2006 | Gorczynski |
| 7,238,352 B2 | 7/2007 | Gorczynski et al. |
| 7,368,535 B2 | 5/2008 | Gorczynski et al. |
| 7,408,041 B2 | 8/2008 | Bowdish et al. |
| 7,422,739 B2 | 9/2008 | Anderson et al. |
| 7,427,665 B2 | 9/2008 | Bowdish et al. |
| 7,435,412 B2 | 10/2008 | Bowdish et al. |
| 7,435,803 B2 | 10/2008 | Hansen et al. |
| 7,452,536 B2 | 11/2008 | Gorczynski et al. |
| 7,598,353 B2 | 10/2009 | Bowdish et al. |
| 7,887,798 B2 | 2/2011 | Gorczynski et al. |
| 8,114,403 B2 * | 2/2012 | Bowdish et al. ........... 424/155.1 |
| 8,709,415 B2 * | 4/2014 | Bowdish et al. ........... 424/130.1 |
| 8,840,885 B2 * | 9/2014 | Bowdish et al. ........... 424/130.1 |
| 2002/0168364 A1 | 11/2002 | Gorczynski et al. |
| 2002/0192215 A1 | 12/2002 | Hoek et al. |
| 2004/0018972 A1 | 1/2004 | Gorczynski et al. |
| 2004/0054145 A1 | 3/2004 | Gorczynski |
| 2004/0175692 A1 | 9/2004 | Bowdish et al. |
| 2004/0198661 A1 | 10/2004 | Bowdish et al. |
| 2005/0074452 A1 | 4/2005 | Bowdish et al. |
| 2005/0107314 A1 | 5/2005 | Gorczynski et al. |
| 2005/0129690 A1 | 6/2005 | Bowdish et al. |
| 2005/0169870 A1 | 8/2005 | Truitt et al. |
| 2006/0057651 A1 | 3/2006 | Bowdish et al. |
| 2007/0036786 A1 | 2/2007 | Tuaillon et al. |
| 2007/0065438 A1 | 3/2007 | Liversidge et al. |
| 2013/0189258 A1 * | 7/2013 | Rother et al. ............ 424/135.1 |

FOREIGN PATENT DOCUMENTS

| | | |
|---|---|---|
| JP | 2-46297 | 2/1990 |
| WO | 85/03508 A1 | 8/1985 |
| WO | 94/28027 A1 | 12/1994 |
| WO | 97/21450 A1 | 6/1997 |
| WO | 99/24565 A1 | 5/1999 |
| WO | 01/87336 A1 | 11/2001 |
| WO | 02/11762 A2 | 2/2002 |

(Continued)

OTHER PUBLICATIONS

Ravandi et al., Leukemia Research (2003); 27: 853-857.*

(Continued)

*Primary Examiner* — Ilia Ouspenski

(74) *Attorney, Agent, or Firm* — Nelson Mullins Riley & Scarborough LLP; Jane E. Remillard, Esq.; Christopher L. Frank

(57) ABSTRACT

The present disclosure relates to anti-CD200 antibodies (e.g., variant anti-CD200 antibodies having decreased or no effector function) and to biomarkers for use in a variety of diagnostic and therapeutic methods, e.g., determining whether a human has been administered one or more of the antibodies at a dose sufficient to induce a desired immunomodulatory effect in the human and/or selecting an appropriate dosing schedule for a patient.

24 Claims, 14 Drawing Sheets

(56) References Cited

FOREIGN PATENT DOCUMENTS

| WO | 02/42332 A2 | 5/2002 |
|---|---|---|
| WO | 02/059280 A2 | 8/2002 |
| WO | 02/095030 A2 | 11/2002 |
| WO | 2004/060295 A2 | 7/2004 |
| WO | WO 2004/060295 A2 | 7/2004 |
| WO | 2004/078938 A2 | 9/2004 |
| WO | WO 2006/020266 A2 | 2/2006 |
| WO | WO 2007/084321 A2 | 7/2007 |
| WO | 2008/089022 A2 | 7/2008 |

OTHER PUBLICATIONS

Sequence alignment, 2015, 3 pages.*
Almasri, Nidal M. et al., "Reduced Expression of CD20 Antigen as a Characteristic Marker for Chronic Lymphocytic Leukemia," American Journal of Hematology, vol. 40:259-263 (1992).
Banerjee, Debatri et al., "Blocking CD200-CD200 receptor axis augments NOS-2 expression and aggravates experimental autoimmune uveoretinitis in Lewis rats," Ocular Immunology and Inflammation, vol. 12(2):115-125 (2004).
Barclay, A. Neil et al., "CD200 and membrane protein interactions in the control of myeloid cells," Trends in Immunology, vol. 23(6):285-290 (2002).
Bello, Celeste et al., "Monoclonal Antibodies for B-Cell Lymphomas: Rituximab and Beyond," Hematology, pp. 233-242 (2007).
Borriello, Frank et al., "MRC OX-2 Defines a Novel T Cell Costimulatory Pathway," The Journal of Immunology, vol. 158:4548-4554 (1997).
Broderick, Cathryn et al., "Constitutive Retinal CD200 Expression Regulates Resident Microglia and Activation State of Inflammatory Cells during Experimental Autoimmune Uveoretinitis," American Journal of Pathology, vol. 161 (5):1669-1677 (2002).
Burge, Daniel J. et al., "Pharmacokinetic and Pharmacodynamic Properties of TRU-015, a CD20-Directed Small Modular Immunopharmaceutical Protein Therpeutic, in Patients with Rheumatoid Arthritis: A Phase I, Open-Label, Dose-Escalation Clinical Study," Clinical Therapeutics, vol. 30(10):1806-1816 (2008).
Chen, Z. et al., "Cloning and characterization of the murine homologue of the rat/human MRC OX-2 gene," Biochimica et Biophysica Acta, vol. 1362:6-10 (1997).
Chen, Dang-Xiao et al., "Discrete Monoclonal Antibodies Define Functionally Important Epitopes in the CD200 Molecule Responsible for Immunosuppression Function," Transplantation, vol. 79:282-288 (2005).
Chen, Dang-Xiao et al., "Synthetic peptides from the N-terminal regions of CD200 and CD200R1 modulate immunosuppressive and anti-inflammatory effects of CD200-CD200R1 interaction," International Immunology, vol. 17 (3):289-296 (2005).
Cherwinski, Holly M. et al., "The CD200 Receptor Is a Novel and Potent Regulator of Murine and Human Mast Cell Function," the Journal of Immunology, vol. 174:1348-1356 (2005).
Cui, Weiguo et al., "CD200 and its receptor, CD200R, modulate bone mass via the differentiation of osteoclasts," PNAS, vol. 104(36):14436-14441 (2007).
Ebert, Ellen C. et al., "Selective Immunosuppressive Action of a Factor Produced by Colon Cancer Cells," Cancer Research, vol. 50:6158-6161 (1990).
Ennishi, D. et al., "CD5 expression is potentially predictive of poor outcome among biomarkers in patients with diffuse large B-cell lymphoma receiving rituximab plus CHOP therapy," Annals of Oncology, vol. 19:1921-1926 (2008).
Fallarino, Francesca et al., "Murine Plasmacytoid Dendritic Cells Initiate the Immunosuppressive Pathway of Tryptophan Catabolism in Response to CD200 Receptor Engagement," The Journal of Immunology, vol. 173:3748-3754 (2004).
Frediberg, Jonathan W., "Unique Toxicities and Resistance Mechanisms Associated with Monoclonal Antibody Therapy," Hematology, pp. 329-334 (2005).
Gorczynski, R.M. et al., "A CD200FC Immunoadhesin Prolongs Rat Islet Xenograft Survival in Mice," Transplantation, vol. 73(12):1948-1953 (2002).
Gorczynski, Reginald M. et al., "An Immunoadhesin Incorporating the Molecule OX-2 Is a Potent Immunosuppressant That Prolongs Allo-and Xenograft Survival," The Journal of Immunology, vol. 163:1654-1660 (1999).
Gorczynski, Reginald M. et al., "Anti-CD200R Ameliorates Collagen-Induced Arthritis in Mice," Clinical Immunology, vol. 104(3):256-264 (2002).
Gorczynski, R.M. et al., "Anti-Rat OX-2 Blocks Increased Small Intestinal Transplant Survival After Portal Vein Immunization," Transplantation Proceedings, vol. 31:577-578 (1999).
Gorczynski, Reginald M. et al., "Augmented Induction of CD4+ CD25+ Treg using Monoclonal Antibodies to CD200R," Transplantation, vol. 79:1180-1183 (2005).
Gorczynski, Reginald M., "CD200 and its receptors as targets for immunoregulation," Current Opinion in Investigational Drugs, vol. 6(5):483-488 (2005).
Gorczynski, Reginald M. et al., "CD200 Immunoadhesin Suppresses Collagen-Induced Arthritis in Mice," Clinical Immunology, vol. 101(3):328-334 (2001).
Gorczynski, Reginald et al., "CD200 Is a Ligand for All Members of the CD200R Family of Immunoregulatory Molecules," The Journal of Immunology, vol. 172:7744-7749 (2004).
Gorczynski, R. et al., "Dendritic Cells Expressing TGFbeta/IL-10, and CHO Cells With OX-2, Increase Graft Survival," Transplantation Proceedings, vol. 33:1585-1566 (2001).
Gorczynski, Reg M., "Evidence for an Immunoregulatory Role of OX2 with Its Counter Ligand (OX2L) in the Regulation of Transplant Rejection, Fetal Loss, Autoimmunity and Tumor Growth," Archivum Immunologiae et Therapiae Experimentalis, vol. 49:303-309 (2001).
Gorczynski, R.M. et al., "Evidence for Persistent Expression of OX2 as a Necessary Component of Prolonged Renal Allograft Survival Following Portal Vein Immunization," Clinical Immunology, vol. 97(1):69-78 (2000).
Gorczynski, R.M. et al., "Evidence of a role for CD200 in regulation of immune rejection of leukaemic tumour cells in C57BL/6 mice," Clin. Exp. Immunol., vol. 126:220-229 (2001).
Gorczynski, Laura et al., "Evidence That an OX-2-Positive Cell Can Inhibit the Stimulation of Type 1 Cytokine Production by Bone Marrow-Derived B7-1 (and B7-2)-Positive Dendritic Cells," The Journal of Immunology, vol. 162:774-781 (1999).
Gorczynski, Reginald M. et al., "Increased Expression of the Novel Molecule OX-2 is Involved in Prolongation of Murine Renal Allograft Survival," Transplantation, vol. 65(8):1106-1114 (1998).
Gorczynski, Reginald M. et al., "Induction of Tolerance-Inducing Antigen-Presenting Cells in Bone Marrow Cultures In Vitro Using Monoclonal Antibodies to CD200R," Transplantation, vol. 77(8):1138-1144 (2004).
Gorczynski, R.M. et al., "Persistent expression of OX-2 is necessary for renal allograft survival," FASEB Journal, vol. 14(6):A1069, Poster Presentation No. 102.4 (2000).
Gorczynski, Reginald M. et al., "Receptor Engagement on Cells Expressing a Ligand for the Tolerance-Inducing Molecule OX2 Induces an Immunoregulatory Population That Inhibits Alloreactivity In Vitro and In Vivo," The Journal of Immunology, vol. 165:4845-4860 (2000).
Gorczynski, R.M. et al., "Structural and Functional Heterogeneity in the CD200R Family of Immoregulatory Molecules and their Expression at the Feto-maternal Interface," American Journal of Reproeuctive Immunology, vol. 52:147-163 (2004).
Gorczynski, R.M. et al., "Synergy in Induction of Increased Renal Allograft Survival after Portal Vein Infusion of Dendritic Cells Transduced to Expression TGFbeta and IL-10, along with Administration of CHO Cells Expressing the Regulatory Molecule OX-2," Clinical Immunology, vol. 95(3):182-189 (2000).
Gorczynski, Reginald M., "Transplant tolerance modifying antibody to CD200 receptor, but not CD200, alters cytokine production profile from stimulated macrophages," Eur. J. Immunol., vol. 31:2331-2337 (2001).

(56) References Cited

OTHER PUBLICATIONS

Hatherley, Deborah et al., "The CD200 and CD200 receptor cell surface proteins interact through their N-terminal immunoglobulin-like domains," Eur. J. Immunol., vol. 34:1688-1694 (2004).
Hernandez-Ilizaliturri, F.J. et al., "Strategies to overcoming rituximab-chemotherapy resistance by targeting the autophagy pathway using bortezomib in combination with the Bcl-2 inhibitor obatoclax in non-Hodgkin's lymphomas (NHL)," Journal of Clinical Oncology, 2009 ASCO Annual Meeting Proceedings, vol. 27(15S), Poster Presentation No. 8543, 1 page (2009).
Hoek, Robert M., "Down-Regulation of the Macrophage Lineage Through Interaction with OX2 (CD200)," Science, vol. 290(5497):1768-1771 (2000).
Hoek, R.M., et al., "Macrophage regulation by the B7.1/2 homologue OX2?" FASEB Journal, vol. 14(6):A1232, Poster Presentation No. 193.1 (2000).
Holodick, Nichol E. et al., "Adult BM generates CD5+ B1 cells containing abundant N-region additions," Eur. J. Immunol., vol. 39(9):2383-2394 (2009).
Hutchings, N.J. et al., "Interactions of Cytoplasmic Region of OX2R are Consistent wtih an Inhibitory Function," Annual Congress of the British Society for Immunology, vol. 101(Suppl. 1), Poster Presentation No. 10.6, 1 page (2000).
Kausar, Fariha et al., "Ocrelizumab: a step forward in the evolution of B-cell therapy," Expert Opin. Biol. Ther., vol. 9(7):889-895 (2009).
Kretz-Rommel, Anke et al., "CD200 Expression on Tumor Cells Suppresses Antitumor Immunity: New Approaches to Cancer Immunotherapy," The Journal of Immunology, vol. 178:5595-5605 (2007).
Kretz-Rommel, Anke et al., "The Immuno-Regulatory Protein CD200 Is Overexpressed in a Subset of B-Cell Lymphocytic Leukemias and Plays a Role in Down-Regulating the TH1 Immune Response," J. Immunother., vol. 27(6):S46 (2004).
Levene, Adam P. et al., "Therapeutic monoclonal antibodies in oncology," Journal of the Royal Society of Medicine, vol. 98:146-152 (2005).
Marti, G.E. et al., "CD20 and CD5 Expression in B-Chronic Lymphocytic Leukemia," Ann. N.Y. Acad. Sci., vol. 651:480-483 (1992).
Mcwhirter, John R. et al., "Antibodies selected from combinatorial libraries block a tumor antigen that plays a key role in immunomodulation," PNAS, vol. 103(4):1041-1046 (2006).
Milani, Cannon et al., "Veltuzumab, an anti-CD20 mAb for the treatment of non-Hodgkin's lymphoma, chronic lymphocytic leukemia and immune thrombocytopenic purpura," Current Opinion in Molecular Therapeutics, vol. 11(2):200-207 (2009).
Morschhauser, Franck et al., "Humanized Anti-CD20 Antibody, Veltuzumab, in Refractory/Recurrent Non-Hodgkin's Lymphoma: Phase I/II Results," Journal of Clinical Oncology, vol. 27(20):3346-3353 (2009).
Gorczynski et al., "Breast Cancer Cell CD200 Expression Regulates Immune Response to EMT6 Tumor Cells in Mice," Breast Cancer Research and Treatment, vol. 123(2): 405-415 (2009).
Supplementary European Search Report for EP 11 73 2296, dated Sep. 30, 2013.
Kretz-Rommel and Bowdish, "Rationale for anti-CD200 immunotherapy in B-CLL and other hematologic malignancies: new concepts in blocking immune suppression," Expert Opinion on Biological Therapy, vol. 8(1), pp. 5-15 (2008).
Kretz-Rommel et al., "CD200 expression on tumor cells suppresses antitumor immunity: New approaches to cancer immunotherapy," Journal of Immunology, vol. 178(9), pp. 5595-5605 (2007).

Pallasch et al., "Disruption of T cell suppression in chronic lymphocytic leukemia by CD200 blockade," Leukemia Research, vol. 33(3), pp. 460-464 (2009).
Simelyte et al., "CD200-Fc, a novel antiarthritic biological agent that targets proinflammatory cytokine expression in the joint of mice with collagen-induced arthritis," Arthritis & Rheumatism, vol. 58(4), pp. 1038-1043 (2008).
Nathan, Carl et al., "Putting the brakes on innate immunity: a regulatory role for CD200?" Nature Immunology, vol. 2(1):17-19 (2001).
Ni, J. et al., "An immunoadhesin incorporating the molecule OX-2 is a potent immunosuppressant which prolongs allograft survival," FASEB Journal, vol. 13(5):A983, Poster Presentation 712.35 (1999).
Petermann, Kimberly B. et al., "CD200 is induced by ERK and is a potential therapeutic target in melanoma," The Journal of Clinical Investigation, vol. 117(12):3922-3929 (2007).
Preston, Sandy et al., "The leukocyte/neuron cell surface antigen OX2 binds to a ligand on macrophages," Eur. J. Immunol., vol. 27(8):1911-1918 (1997).
Ragheb, Rafik F.A. et al., "Exploration of OX-2 function in tolerance induction and graft acceptance using an anti-mouse OX-2 monoclonal antibody," Masters Abstracts International, vol. 38(4):971-972 (2000).
Ragheb, Rafik et al., "Preparation and functional properties of monoclonal antibodies to human, mouse and rat OX-2," Immunology Letters, vol. 68:311-315 (1999).
Reddy, N.M. et al., Rituximab resistance and its association with changes in the internal domain of CD20 antigen and down-regulation of pro-apoptotic protein Bax and Bak in both rituximab-resistant cell lines (RRCL) and diffuse large B-cell lymphoma (DLBCL) patient (pt) samples, Journal of Clinical Oncology, 2006 ASCO Annual Meeting Proceedings, vol. 24(18S), Poster Presentation No. 17509 (2006).
Rijkers, Eva S.K. et al., "The inhibitory CD200R is differentially expressed on human and mouse T and B lymphocytes," Molecular Immunology, vol. 45:1126-1135 (2008).
Romagnani, Sergio et al., "Short Analytical Review, TH1 and TH2 in Human Diseases," Clinical Immunology and Immunopathology, vol. 80(3):225-235 (1996).
Rosenblum, Michael D. et al., "CD200 is a novel p53-target gene involved in apoptosis-associated immune tolerance," Blood, vol. 103(7):2691-2698 (2004).
Taylor, Neil et al., "Enhanced Tolerance to Autoimmune Uveitis in CD200-Deficient Mice Correlates wtih a Pronounced Th2 Switch in Response to Antigen Challenge," The Journal of Immunology, vol. 174:143-154 (2005).
Tedder, Thomas F. et al., "Isolation and structure of a cDNA encoding the B1 (CD20) cell-surface antigen of human B lymphocytes," Proc. Natl. Acad. Sci. USA, vol. 85:208-212 (1988).
Teeling, Jessica L. et al., "The Biological Activity of Human CD20 Monoclonal Antibodies Is Linked to Unique Epitopes on CD20," The Journal of Immunology, vol. 177:362-371 (2006).
Transplantation Tech., Inc. WO02095030, "Modulation of CD200 Receptors as a Novel Method of Immunosuppression," Expert Opin. Ther. Patents, vol. 13(5):711-715 (2003).
Wright, Gavin J. et al., "Lymphoid/Neuronal Cell Surface OX2 Glycoprotein Recognizes a Novel Receptor on Macrophages Implicated in the Control of Their Function," Immunity, vol. 13:233-242 (2000).
Wright, G.J. et al., "The lymphoid/neuronal OX-2 glycoprotein Interacts with a nove protein expressed by macrophages," Tissue Antigens, vol. 55(Suppl. 1):11, Poster Presentation A. 9 (2000).
Zhang, Shuli et al., "Molecular Mechanisms of CD200 Inhibition of Mast Cell Activation," The Journal of Immunology, vol. 173:6786-6793 (2004).

\* cited by examiner

BIOMARKERS OF IMMUNOMODULATORY EFFECTS IN HUMANS TREATED WITH ANTI-CD200 ANTIBODIES

CROSS-REFERENCE TO RELATED APPLICATIONS

This application is a national stage filing under 35 U.S.C. 371 of International Application No. PCT/US11/20750, filed Jan. 11, 2011, which claims priority to and the benefit of U.S. Provisional Patent Application Ser. Nos. 61/416,974, filed Nov. 24, 2010; 61/401,442, filed Aug. 12, 2010; 61/337,997, filed Feb. 11, 2010; 61/294,066, filed Jan. 11, 2010, the entire contents of which are incorporated herein by reference. International Application PCT/US11/20750 was published under PCT Article 21(2) in English.

SEQUENCE LISTING

The instant application contains a Sequence Listing which has been submitted via EFS-Web and is hereby incorporated by reference in its entirety. Said ASCII copy, created on Apr. 17, 2013, is named ALXN151301_Seq.txt, and is 16,618 bytes in size.

TECHNICAL FIELD

The field of the invention is medicine, immunology, molecular biology, and protein chemistry.

BACKGROUND

Human CD200 protein is a type 1a transmembrane glycoprotein that is normally expressed on thymocytes (e.g., T cells and B cells), neurons, and endothelial cells. Through engagement with its cognate receptor, CD200R, CD200 protein transduces an immunoregulatory signal that can suppress T-cell-mediated immune responses. CD200 knockout animal studies as well as experiments using antagonist anti-CD200 antibodies and recombinant CD200-Fc fusion proteins have demonstrated that CD200 protein functions as an immunosuppressive agent in autoimmune disorder and during transplantation. (See, e.g., Hoek et al. (2000) *Science* 290:1768-1771 and Gorczynski et al. (1999) *J Immunol* 163:1654-1660). The interaction between CD200 and CD200R results in altered cytokine profiles and promotes a $T_H2$ T cell response (humoral immune response) over a $T_H1$ response (cellular immune response). See, e.g., Kretz-Rommel (2007) *J Immunol* 178:5595-5605.

The human immune system employs a variety of immunosurveillance mechanisms, which can identify malignant cells within a host organism and kill the cells before a cancer develops. See, e.g., Geertsen et al. (1999) *Int J Mol Med* 3(1):49-57; Kerebijn et al. (1999) *Crit. Rev Oncol Hematol* 31(1):31-53; and Pardoll (2003) *Annu Rev Immunol* 21:807-39. However, cancer cells are known to evade detection by the immune system. One potential mechanism by which cancer cells escape immunosurveillance is expression or overexpression of CD200 protein. In fact, CD200 protein has been shown to be expressed or overexpressed on a variety of human cancer cells including, e.g., B cell chronic lymphocytic leukemia cells, prostate cancer cells, breast cancer cells, colon cancer cells, and brain cancer cells. See, e.g., Kawasaki et al. (2007) *Biochem Biophys Res Commun* 364(4):778-782; Kretz-Rommel et al. (2007), supra; and Siva et al. (2008) *Cancer Immunol Immunother* 57(7):987-96.

Molecular biomarkers are often used in early drug development studies to determine, for example, whether a drug is biologically active in a patient—that the drug produced a measurable biological effect in the patient to which the drug is administered. For example, biomarkers can be useful during phase I studies to establish dosing schedules for future phase II studies and in general to help determine clinically-meaningful and optimized dosing schedules for treating patients suffering from disease. Biomarkers can also be useful for identifying the occurrence of potential side-effects or other non-therapeutic effects in a human treated with a drug to thereby determine a safety profile for the drug.

SUMMARY

The present disclosure is based, at least in part, on the discovery by the inventors of several biomarkers, a change (e.g., an increase or decrease) in one or more of which evidences the occurrence in a human of a desired immunomodulatory effect as a result of administration of an anti-CD200 antibody to the human. For example, the inventors have observed that following administration of an anti-CD200 antibody to a human, the concentration of circulating $CD200^+$ leukocytes (e.g., subsets of $CD200^+$ T cells including, e.g., $CD200^+/CD4^+$ T cells and/or activated $CD200^+/CD4+$ T cells) is reduced in the human. While the disclosure is not bound by any particular theory or mechanism of action, the inventors believe that the observed loss of $CD200^+$ leukocytes is due to one or both of: (a) loss of CD200 expression by the leukocytes and (b) mobilization of the cells out of the periphery, rather than a deletion of the $CD200^+$ leukocytes. Also observed by the inventors was that upon administration of an anti-CD200 antibody, the expression level of CD200R by a variety of leukocyte subsets (e.g., CD4+ T cells, $CD8^+$ T cells, activated CD4+ T cells, NK T cells, or $CD21^+/CD25^+/Fox3P^+$ T cells) was increased. In addition, the inventors further observed that administration of an anti-CD200 antibody to a human afflicted with a cancer resulted in: (i) an increased concentration of activated T cells as compared to the concentration of the cells in the human prior to administration of the anti-CD200 antibody; (ii) a decreased concentration of regulatory T cells, as compared to the concentration of the cells in the human prior to administration of the anti-CD200 antibody; and (iii) an increase in the ratio of percent activated T cells to percent regulatory T cells, as compared to the corresponding ratio in the human prior to administration of the anti-CD200 antibody. In fact, as elaborated on in the working examples, the concentration of regulatory T cells decreased in four of seven (57%) patients whose clinical disease stabilized or improved, whereas only 29% of patients whose clinical disease progressed clinically experienced a similar decrease in the concentration of regulatory T cells.

Anti-CD200 antibodies are currently under investigation as potential therapeutic agents for treating a variety of diseases including, but not limited to, cancer, inflammatory disorders (e.g., graft rejection), and bone disorders. For example, the humanized anti-CD200 antibody ALXN6000 (samalizumab; Alexion Pharmaceuticals, Inc., Cheshire, Conn.) is being evaluated presently in clinical trials for the treatment of cancer. While the disclosure is not bound by any particular theory or mechanism of action, the inventors believe that monitoring a patient treated with an anti-CD200 antibody such as samalizumab for a change (e.g., an increase or a decrease) in one or more of the biomarkers described herein is useful for determining whether the anti-CD200 antibody is capable of producing a desired immunomodulatory effect in the human to which the antibody is administered. Moreover, monitoring the extent of the immunomodulatory effect (e.g., by detecting a change in one or more of the biomarkers described herein) is also useful for identifying a dose—a threshold dose or a dosing schedule—of an anti-CD200 antibody (e.g., samalizumab) that, by virtue of the immunomodulatory effect of the antibody in the human, is sufficient to achieve a clinically-meaningful effect on the disease (i.e., sufficient to treat a disease such as cancer). To with, seven of twenty-five B-CLL and multiple myeloma patients administered samalizumab in a phase I safety study exhibited stable disease as determined by serial assessments of peripheral blood counts and CT scans. A desired immunomodulatory effect of the anti-CD200 antibody was observed in treated patients as reflected in a change (e.g., an increase or reduction) in one or more of the anti-CD200 antibody-associated biomarkers described herein.

Accordingly, in one aspect, the disclosure provides a method for determining whether an anti-CD200 antibody has produced a desired immunomodulatory effect in a human (e.g., a cancer patient). The method includes detecting an increase or decrease of at least one immunomodulatory biomarker (sometimes referred to herein as an "anti-CD200 antibody-associated immunomodulatory biomarker") described herein in a blood sample obtained from a human who has been administered an anti-CD200 antibody to thereby determine whether the anti-CD200 antibody has produced an immunomodulatory effect in the human. The immunomodulatory effect can be characterized by a change (e.g., an increase or a decrease) in at least one biomarker, e.g., an anti-CD200 antibody-associated immunomodulatory biomarker described herein, the change selected from the group consisting of: (i) a reduced concentration of regulatory T cells, relative to the concentration of regulatory T cells of the same histological type in the human prior to the first administration of the antibody; (ii) an increased concentration of $CD8^+$ T cells, relative to the concentration of $CD8^+$ T cells of the same histological type in the human prior to the first administration of the antibody; (iii) an increased concentration of activated T cells, relative to the concentration of activated T cells of the same histological type in the human prior to the first administration of the antibody; (iv) a reduced concentration of $CD200^+$ leukocytes (e.g., $CD200^+$ T cells), relative to the concentration of $CD200^+$ leukocytes of the same histological type in the human prior to the first administration of the antibody; (v) an increase in the concentration of $CD200R^+$ leukocytes (e.g., $CD200R^+$ T cells), relative to the concentration of $CD200R^+$ leukocytes of the same histological type in the human prior to the first administration of the antibody; (vi) a ratio of percent activated T cells to percent regulatory T cells (T regs) of at least 2:1 (e.g., at least 3:1, at least 4:1, at least 5:1, at least 6:1, or at least 7:1), relative to the ratio of activated T cells to T regs in the human prior to the first administration of the antibody; (vii) a decreased level of CD200 expression by a plurality of leukocytes in a biological sample obtained from a patient prior to administration to the patient of an anti-CD200 antibody, relative to the level of CD200 expression by a plurality of leukocytes of the same histological type in a biological sample from the patient prior to administration of the antibody; and (viii) an increased level of CD200R expression by a plurality of leukocytes in a biological sample from a patient administered an anti-CD200 antibody, relative to the level of CD200R expression by a plurality of leukocytes in a biological sample from the patient prior to administration of the anti-CD200 antibody. In some embodiments, a reduction in CD200 expression by a plurality of leukocytes (e.g., bone marrow cells or splenocytes) in a biological sample obtained from the patient after administration of the anti-CD200 antibody, as compared to a control expression level (e.g., the level of CD200 expression in a plurality of leukocytes of the same histological type in a biological sample obtained from the patient prior to administration of the anti-CD200 antibody) indicates that the anti-CD200 antibody has produced a desired immunomodulatory effect in the human. It is understood that any of the methods described herein can involve determining whether there has been a change (e.g., an increase or a decrease) in two or more (e.g., three, four, five, six, seven, eight, nine, or 10 or more) of the anti-CD200 antibody-associated biomarkers described herein. Where interrogation of more than one of the biomarkers is practiced, any combination of two or more (e.g., three, four, five, six, seven, eight, nine, or 10 or more) of the biomarkers can be analyzed.

It is understood that in some embodiments, a change in expression can be a change in protein expression or a change in mRNA expression. That is, for example, the methods can interrogate a population of leukocytes from a patient to determine if a reduction in the level of CD200 mRNA and/or CD200 protein expression has occurred, relative to a control level of mRNA and/or protein expression. Methods for measuring protein and mRNA expression are well known in the art and described herein.

In some embodiments, a reduction in the concentration of one or more subsets of $CD200^+$ bone marrow cells in a biological sample obtained from the patient, as compared to the concentration of the same subsets of $CD200^+$ bone marrow cells in a control sample, indicates that the anti-CD200 antibody has produced a desired immunomodulatory effect in the human. The $CD200^+$ leukocytes (e.g., bone marrow cells or splenocytes) or subsets can be, but are not limited to, any of the $CD200^+$ leukocytes (e.g., bone marrow cells or splenocytes) or subsets described herein (infra).

It is understood that the detecting can comprise, e.g., measuring the concentration of the appropriate selected cell type (e.g., CD200+ or $CD200R^+$ leukocytes) or quantifying the level of expression of one or more expression markers such as CD200 or CD200R.

In some embodiments of any of the methods described herein, the detecting can occur following the first dose of the anti-CD200 antibody. For example, the detecting (i.e., detecting a change (e.g., an increase or decrease) in at least one of the biomarkers) can occur within (or less than) two (2) months (e.g., less than eight weeks, seven weeks, six weeks, five weeks, one month, four weeks, three weeks, two weeks or 13 days, 12 days, 11 days, 10 days, nine days, eight days, seven days, six days, five days, or less than 5 days) after the first therapeutic dose of the anti-CD200 antibody is administered to the human. In some embodiments of any of the methods described herein, the detecting does not occur until at least 10 days (e.g., at least 11 days, 12 days, 13 days, 14 days or one week, two weeks, three weeks, four weeks, a month, five weeks, six weeks, seven weeks, or eight weeks or more) after the first therapeutic dose of the anti-CD200 antibody is administered to the human. It is understood that, e.g., in the following methods described herein, measuring the concentration of the specified cell types or quantifying the level of expression of an expression marker (e.g., CD200 or CD200R) can occur, e.g., within any one of the aforementioned time periods.

In embodiments in which at least two (e.g., at least three, four, five, six, seven, eight, nine, 10, 11, 12, 13, or 14 or more) doses of the anti-CD200 antibody are administered to the human prior to detecting a change (e.g., an increase or a decrease) in the at least one biomarker, the detecting can occur, e.g., within (or less than) two months (e.g., less than eight weeks, seven weeks, six weeks, five weeks, one month, four weeks, three weeks, two weeks or 13 days, 12 days, 11 days, 10 days, nine days, eight days, seven days, six days, five days, or less than 5 days), and/or not until at least 1 day (e.g., at least two days, three days, four days, five days, six days, seven days, eight days, nine days, 10 days, 11 days, 12 days, 13 days, 14 days, 15 days, 16 days, 17 days, 18 days, 19 days, 20 days, or three weeks, four weeks, a month, five weeks, six weeks, seven weeks, or eight weeks or more) after, the last dose of the multiple dose anti-CD200 antibody regimen is administered to the human. In some embodiments, the detecting can occur between dosing (e.g., between the first and second dose, between the second and third dose, between the third and fourth dose, between the fifth and six dose, and/or between the seventh and eighth dose). Such detection can be useful for determining a dosing schedule for the human that is effective to maintain the immunomodulatory effect (e.g., the peak or maximum level of the immunomodulatory effect) in the human over the course of treatment. It is understood that, e.g., in the following methods described herein, measuring the concentration of the specified cell types or quantifying the level of expression of an expression marker (e.g., CD200 or CD200R) can occur, e.g., within any one of the aforementioned time periods. In some embodiments, detecting a change in one or more of the biomarkers described herein can occur throughout the treatment of the patient (e.g., before and/or after each dose of the anti-CD200 antibody administered to the patient). Such detection can be useful for, among other things, a longitudinal evaluation of the effect of the anti-CD200 antibody on the physiology of the patient and allowing for a more precise correlation between the occurrence of immunomodulatory effects and efficacy of the anti-CD200 antibody treatment.

In some embodiments, a positive determination that a desired immunomodulatory effect has occurred in the human results in a decision by a medical practitioner to continue, or officially begin, a treatment regimen for the human (e.g., where the human has, is suspected of having, or at risk for developing, a disease (e.g., a cancer) which the medical practitioner believes will benefit from an anti-CD200 antibody immunomodulatory therapy) that includes administration of an anti-CD200 antibody in an amount and with a frequency effective to maintain the occurrence in the human of the desired immunomodulatory effect. In some embodiments, a positive determination that a desired immunomodulatory effect has occurred in the human results in the medical practitioner continuing to prescribe and/or select an anti-CD200 antibody therapy for the human. In some embodiments, a positive determination that a desired immunomodulatory effect has occurred in the human as a result of administration of the anti-CD200 antibody results in a continued monitoring of the human for a change (e.g., an increase or decrease) in the one or more biomarkers in the human, e.g., after each dose of the anti-CD200 antibody administered or after every two doses, etc. This practice can also be useful for determining a dosing schedule for the human that is effective to maintain the immunomodulatory effect (e.g., the peak or maximum level of the desired immunomodulatory effect) in the human over the course of treatment.

In another aspect, the disclosure features a method for determining whether an anti-CD200 antibody has produced a desired immunomodulatory effect in a human. The method comprises measuring the concentration of CD200$^+$ leukocytes in a blood sample obtained from a human administered an anti-CD200 antibody, wherein a reduction in the concentration of CD200$^+$ leukocytes in the blood sample as compared to the concentration of CD200+ leukocytes of the same histological type in a control sample indicates that the anti-CD200 antibody has produced a desired immunomodulatory effect in the human. The CD200$^+$ leukocytes can be, e.g., any of the CD200$^+$ leukocytes described herein.

In another aspect, the disclosure features a method for determining whether an anti-CD200 antibody has produced a desired immunomodulatory effect in a human. The method comprises measuring the concentration of CD200$^+$ T cells in a blood sample obtained from a human administered an anti-CD200 antibody, wherein a reduction in the concentration of CD200$^+$ T cells in the blood sample as compared to the concentration of CD200$^+$ T cells of the same histological type in a control sample indicates that the anti-CD200 antibody has produced a desired immunomodulatory effect in the human.

In another aspect, the disclosure features a method for determining whether an anti-CD200 antibody has produced a desired immunomodulatory effect in a human, which method comprises measuring the concentration of CD200R$^+$ leukocytes in a blood sample obtained from a human administered an anti-CD200 antibody, wherein an increase in the concentration of CD200R$^+$ leukocytes in the blood sample as compared to the concentration of CD200R$^+$ leukocytes of the same histological type in a control sample indicates that the anti-CD200 antibody has produced a desired immunomodulatory effect in the human.

In another aspect, the disclosure features a method for determining whether an anti-CD200 antibody has produced a desired immunomodulatory effect in a human. The method comprises quantifying the level of CD200 expression by a plurality of leukocytes in a biological sample from a human administered an anti-CD200 antibody, wherein a reduction in CD200 expression by the plurality as compared to the expression level of a plurality of leukocytes of the same histological type in a control sample indicates that the anti-CD200 antibody has produced a desired immunomodulatory effect in the human.

In yet another aspect, the disclosure features a method for determining whether an anti-CD200 antibody has produced a desired immunomodulatory effect in a human, wherein the method comprises quantifying the level of CD200R expression by a plurality of leukocytes in a biological sample from a human administered an anti-CD200 antibody, wherein an increase in CD200R expression by the plurality as compared to the expression level of CD200R by a plurality of leukocytes of the same histological type in a control sample indicates that the anti-CD200 antibody has produced a desired immunomodulatory effect in the human.

In some embodiments, any of the methods described herein (e.g., the methods for determining whether an anti-CD200 has produced a desired immunomodulatory effect in a human) can include administering the anti-CD200 antibody to the human in accordance with the methods. For example, the disclosure features a method for determining whether an anti-CD200 antibody has produced a desired immunomodulatory effect in a human, which method comprises: administering an anti-CD200 antibody to a human and quantifying the level of CD200R expression by a plurality of leukocytes in a biological sample from the human after administration of the anti-CD200 antibody, wherein an increase in CD200R expression by the plurality as compared to the expression level of CD200R by a plurality of leukocytes of the same histological type in a control sample indicates that the anti-CD200 antibody has produced a desired immunomodulatory effect in the human.

In some embodiments, any of the methods described herein (e.g., the methods for determining whether an anti-CD200 has produced a desired immunomodulatory effect in a human) can include measuring the concentration of the specified cell type, or quantifying the level of expression of a specified expression marker on a specified cell type, in a biological sample obtained from the human prior to administration of the antibody. For example, the disclosure features a method for determining whether an anti-CD200 antibody has produced a desired immunomodulatory effect in a human, wherein the method comprises: measuring the concentration of $CD200^+$ T cells in a blood sample from a human prior to administering an anti-CD200 antibody to the human; and measuring the concentration of $CD200^+$ T cells in a blood sample from the human after an anti-CD200 antibody has been administered to the human (e.g., by the same practitioner or a different practitioner), wherein a reduction in the concentration of CD200+ T cells in the post-treatment blood sample as compared to the concentration of $CD200^+$ T cells of the same histological type in the blood sample obtained prior to treatment indicates that the anti-CD200 antibody has produced a desired immunomodulatory effect in the human.

In some embodiments, any of the methods described herein includes obtaining the biological sample (e.g., the blood sample) from the patient before and/or after administration of the anti-CD200 antibody to the human.

In another aspect, the disclosure features a method for determining whether an anti-CD200 antibody has produced a desired immunomodulatory effect in a human. The method comprises measuring the concentration of a population of $CD200^+$ leukocytes (e.g., $CD200^+$ T cells) in a blood sample obtained from a human administered an anti-CD200 antibody; and quantifying the level of CD200R expression by a plurality of leukocytes in a biological sample from the human administered an anti-CD200 antibody, wherein one or both of: (i) a reduction in the concentration of a population of $CD200^+$ leukocytes in the blood sample as compared to the concentration of a corresponding population of CD200+ leukocytes of the same histological type in a control sample and (ii) an increase in CD200R expression by the plurality as compared to a control expression level, indicates that the anti-CD200 antibody has produced a desired immunomodulatory effect in the human.

In yet another aspect, the disclosure features a method for determining whether an anti-CD200 antibody has produced a desired immunomodulatory effect in a human, the method comprising: (i) measuring the concentration of a population of $CD200^+$ leukocytes (e.g., $CD200^+$ T cells) in a biological sample obtained from a human prior to administration to the human of an anti-CD200 antibody to thereby obtain a pre-treatment $CD200^+$ leukocyte population concentration; (ii) administering to the human the antibody; and (iii) measuring the concentration of a population of $CD200^+$ leukocytes of the same histological type in a blood sample obtained from the human following administration of the antibody to thereby obtain a post-treatment $CD200^+$ leukocyte population concentration, wherein a reduction in the post-treatment $CD200^+$ leukocyte concentration as compared to the pre-treatment $CD200^+$ leukocyte concentration indicates that the antibody has produced a desired immunomodulatory effect in the human.

In another aspect, the disclosure features a method for determining whether an anti-CD200 antibody has produced a desired immunomodulatory effect in a human, the method comprising: (i) measuring the concentration of $CD200R^+$ leukocytes (e.g., $CD200R^+$ T cells) in a biological sample obtained from a human prior to administration to the human of an anti-CD200 antibody to thereby obtain a pre-treatment $CD200R^+$ leukocyte concentration; (ii) administering to the human the antibody; and (iii) measuring the concentration of $CD200R^+$ leukocytes (e.g., $CD200R^+$ T cells) of the same histological type in a blood sample obtained from the human following administration of the antibody to thereby obtain a post-treatment $CD200R^+$ leukocyte concentration, wherein an increase in the post-treatment $CD200R^+$ leukocyte concentration as compared to the pre-treatment $CD200R^+$ leukocyte concentration indicates that the antibody has produced a desired immunomodulatory effect in the human.

In yet another aspect, the disclosure features a method for determining whether an anti-CD200 antibody has produced a desired immunomodulatory effect in a human, the method comprising: (i) quantifying the level of CD200 expression by a plurality of leukocytes in a biological sample from a human prior to administration to the human of an anti-CD200 antibody to thereby obtain a pre-treatment CD200 expression level; (ii) administering to a human the anti-CD200 antibody; and (iii) quantifying the level of CD200 expression by a plurality of leukocytes in a biological sample from the human obtained after the administration of the antibody to thereby obtain a post-treatment CD200 expression level, wherein a reduction in post-treatment CD200 expression level as compared to the pre-treatment CD200 expression level indicates that the antibody has produced a desired immunomodulatory effect in the human.

In another aspect, the disclosure features a method for determining whether an anti-CD200 antibody has produced a desired immunomodulatory effect in a human. The method includes: (i) quantifying the level of CD200R expression by a plurality of leukocytes in a biological sample from a human prior to administration to the human of an anti-CD200 antibody to thereby obtain a pre-treatment CD200R expression level; (ii) administering to a human the anti-CD200 antibody; and (iii) quantifying the level of CD200R expression by a plurality of leukocytes in a biological sample obtained from the human after the administration of the antibody to thereby obtain a post-treatment CD200R expression level, wherein an increase in post-treatment CD200R expression level as compared to the pre-treatment CD200R expression level indicates that the antibody has produced a desired immunomodulatory effect in the human.

With respect to CD200 expression by leukocytes, the leukocytes can be, e.g., T cells such as $CD200^+/CD4^+$ T cells, activated $CD200^+/CD4^+$ T cells, or $CD200^+/CD8^+$ T cells. In some embodiments of any of the methods described herein, the leukocytes are T cells such as $CD200^+/CD4^+$ T cells or activated $CD200^+$/CD4+ T cells.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % reduction of the concentration of $CD200^+$ leukocytes indicates that a desired immunomodulatory effect has been produced in the human. In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % reduction of the concentration of $CD200^+$ leukocytes indicates that the antibody is therapeutically effective in the human.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 or more) % increase in the concentration of $CD200R^+$ leukocytes indicates that a desired immunomodulatory effect has been produced in the human. In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 or more) % increase in the concentration of CD200R⁺ leukocytes indicates that the antibody is therapeutically effective in the human.

In some embodiments of any of the methods described herein, e.g., with respect to CD200R expression by leukocytes, the leukocytes can be, e.g., CD4⁺ T cells, CD8⁺ T cells, activated CD4⁺ T cells, CD21⁺/CD25⁺/Fox3P⁺ T cells, and NK T cells.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % reduction in CD200 expression by the leukocytes (e.g., T cells) indicates that a desired immunomodulatory effect has been produced in the human.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % reduction in CD200 expression by the leukocytes (e.g., T cells) indicates that the antibody is therapeutically effective in the human.

In some embodiments of any of the methods described herein, at least a 1.5 (e.g., 2, 2.5, 3, 3.5, 4, 4.5, 5, 5.5, 6, 6.5, 7, 7.5, 8, 8.5, 9, 9.5, or 10 or more)-fold increase in CD200R expression by the plurality of leukocytes indicates that a desired immunomodulatory effect has been produced by the antibody in the human. In some embodiments of any of the methods described herein, at least a 1.5 (e.g., 2, 2.5, 3, 3.5, 4, 4.5, 5, 5.5, 6, 6.5, 7, 7.5, 8, 8.5, 9, 9.5, or 10 or more)-fold increase in CD200R expression by the plurality of leukocytes indicates that the anti-CD200 antibody is therapeutically effective in the human.

In some embodiments of any of the methods described herein, a reduction in the concentration of CD200⁺ T cells in the blood sample as compared to the concentration of CD200+ T cells of the same histological type in the control sample indicates that the antibody is therapeutically effective in the human.

In some embodiments of any of the methods described herein, an increase in the concentration of CD200R⁺ T cells in the blood sample as compared to the concentration of CD200R⁺ T cells of the same histological type in the control sample indicates that the antibody is therapeutically effective in the human.

In some embodiments of any of the methods described herein, a reduction in the level of CD200 expression by the plurality as compared to the control expression level indicates that the anti-CD200 antibody is therapeutically effective in the human.

In some embodiments of any of the methods described herein, an increase in the level of CD200R expression by the plurality as compared to the control expression level indicates that the anti-CD200 antibody is therapeutically effective in the human.

In another aspect, the disclosure features a method for determining whether an anti-CD200 antibody has produced a desired immunomodulatory effect in a human, which method comprises measuring the concentration of regulatory T cells (T regs) in a blood sample obtained from a human administered an anti-CD200 antibody. A reduction in the concentration of T regs in the blood sample, as compared to the concentration of T regs of same histological type in a control sample, indicates that the anti-CD200 antibody has produced a desired immunomodulatory effect in the human. The control sample can be, e.g., a blood sample obtained from the patient prior to administration of the first therapeutic dose of the anti-CD200 antibody.

In another aspect, the disclosure features a method for determining whether an anti-CD200 antibody has produced a desired immunomodulatory effect in a human, wherein the method includes: (i) measuring the concentration of regulatory T cells (T regs) in a blood sample obtained from a human prior to administration to the human of an anti-CD200 antibody to thereby obtain a pre-treatment T regs concentration; (ii) administering to the human the anti-CD200 antibody; and (iii) measuring the concentration of T regs of the same defined histological type in a blood sample obtained from the human after administration of the anti-CD200 antibody, wherein a reduction in the concentration of T regs in the post-treatment blood sample, as compared to the pre-treatment T regs concentration, indicates that the anti-CD200 antibody has produced a desired immunomodulatory effect in the human.

In some embodiments of the methods described herein, the T regs can be, e.g., CD3⁺CD4⁺CD25⁺FoxP3⁺ T cells or CD3⁺CD4⁺FoxP3⁺ T cells.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % reduction of the concentration of T regs indicates that a desired immunomodulatory effect has been produced in the human. In some embodiments, the T regs (for example, the T regs defined by the foregoing expression markers) can express CD200 or CD200R.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % reduction of the concentration of T regs indicates that the antibody is therapeutically effective in the human.

In yet another aspect, the disclosure features a method for determining whether an anti-CD200 antibody has produced a desired immunomodulatory effect in a human, which method comprises measuring the concentration of activated T cells in a blood sample obtained from a human administered an anti-CD200 antibody, wherein an increase in the concentration of activated T cells in the blood sample, as compared to the concentration of activated T cells of same histological type in a control sample, indicates that the anti-CD200 antibody has produced a desired immunomodulatory effect in the human. The control sample can be, e.g., a blood sample obtained from the patient prior to administration of the first therapeutic dose of the anti-CD200 antibody.

In another aspect, the disclosure features a method for determining whether an anti-CD200 antibody has produced a desired immunomodulatory effect in a human, the method comprising: (i) measuring the concentration of activated T cells in a blood sample obtained from a human prior to administration to the human of an anti-CD200 antibody to thereby obtain a pre-treatment activated T cell concentration; (ii) administering to the human the anti-CD200 antibody; and (iii) measuring the concentration of activated T cells of the same defined histological type in a blood sample obtained from the human after administration of the anti-CD200 antibody, wherein an increase in the concentration of activated T cells in the post-treatment blood sample, as compared to the pre-treatment activated T cell concentration, indicates that the anti-CD200 antibody has produced a desired immunomodulatory effect in the human.

In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 or more) % increase in the concentration of activated T cells indicates that a desired immunomodulatory effect has been produced in the human. In some embodiments of any of the methods described herein, at least a 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 or more) % increase in the concentration of activated T cells indicates that the antibody is therapeutically effective in the human.

In yet another aspect, the disclosure features a method for determining whether an anti-CD200 antibody has produced a desired immunomodulatory effect in a human, which method comprises determining the ratio of percent activated T cells to percent regulatory T cells in a blood sample obtained from a human administered an anti-CD200 antibody, wherein an increase in the ratio of percent activated T cells to percent regulatory T cells in the blood sample, as compared to the ratio of percent activated T cells to percent regulatory T cells in a control sample, indicates that the anti-CD200 antibody has produced a desired immunomodulatory effect in the human.

In yet another aspect, the disclosure features a method for determining whether an anti-CD200 antibody has produced a desired immunomodulatory effect in a human, which method comprises determining the ratio of percent activated T cells to percent regulatory T cells in a blood sample obtained from a human administered an anti-CD200 antibody, wherein a ratio of percent activated T cells to percent regulatory T cells of at least 2:1 (e.g., at least 3:1, at least 4:1, at least 5:1, at least 6:1, or at least 7:1) indicates that the anti-CD200 antibody has produced a desired immunomodulatory effect in the human.

In another aspect, the disclosure features a method for determining whether an anti-CD200 antibody has produced a desired immunomodulatory effect in a human, the method comprising: (i) determining the ratio of percent activated T cells to percent regulatory T cells in a blood sample obtained from a human administered an anti-CD200 antibody to thereby determine a pre-treatment ratio; (ii) administering to the human the anti-CD200 antibody; and (iii) determining the ratio of percent activated T cells to percent regulatory T cells in a blood sample obtained from the human after administration of the anti-CD200 antibody, wherein an increase in the ratio of percent activated T cells to percent regulatory T cells in the post-treatment blood sample, as compared to the pre-treatment ratio, indicates that the anti-CD200 antibody has produced a desired immunomodulatory effect in the human.

In some embodiments of any of the methods described herein, the activated T cells can be, e.g., $CD3^+CD4^+CD25^+FoxP3^{neg}$ T cells or $CD3^+CD4^+FoxP3^{neg}$ T cells.

In some embodiments, the activated T cells (for example, the activated T cells defined by the foregoing expression markers) can express CD200 or CD200R.

In some embodiments of any of the methods described herein, the control sample can be or contain a blood sample from the human obtained prior to administering the anti-CD200 antibody.

In another aspect, the disclosure features a method for determining whether an anti-CD200 antibody has produced a desired immunomodulatory effect in a human. The method includes measuring: (a): (i) the concentration of $CD200^+$ leukocytes in a biological sample obtained from a human following administration to the human of an anti-CD200 antibody and (ii) the concentration of $CD200^+$ leukocytes of the same histological type as in (i) in a biological sample obtained from the human prior to administration of the antibody; (b): (iii) the concentration of $CD200R^+$ leukocytes in a biological sample obtained from a human following administration to the human of an anti-CD200 antibody and (iv) the concentration of $CD200R^+$ leukocytes of the same histological type as in (iii) in a biological sample obtained from the human prior to administration of the antibody; (c): (v) the level of expression of CD200R by a plurality of leukocytes in a biological sample obtained from the human following administration to the human of an anti-CD200 antibody and (vi) the level of expression of CD200R by a plurality of leukocytes of the same histological type as in (v) in a biological sample obtained from the human prior to administration of the antibody; (d): (vii) the level of expression of CD200 by a plurality of leukocytes in a biological sample obtained from the human following administration to the human of an anti-CD200 antibody and (viii) the level of expression of CD200 by a plurality of leukocytes of the same histological type as in (vii) in a biological sample obtained from the human prior to administration of the antibody; (e): (ix) the concentration of regulatory T cells in a biological sample from a human following administration to the human of an anti-CD200 antibody and (x) the concentration of regulatory T cells of the same histological type as in (ix) in a biological sample from the human prior to administration of the anti-CD200 antibody; (f): (xi) the concentration of activated T cells in a biological sample from a human following administration of an anti-CD200 antibody to the human and (xii) the concentration of activated T cells of the same histological type as in (xi) in a biological sample from the human prior to administration of the anti-CD200 antibody; (g): (xiii) the ratio of percent activated T cells to percent regulatory T cells in a biological sample from a human following administration of an anti-CD200 antibody and (xiv) the corresponding ratio of percent activated T cells to percent regulatory T cells (each of the same histological type as in (xiii)) in a biological sample from the human prior to administration of the anti-CD200 antibody; (h): (xv) the concentration of $CD8^+$ lymphocytes in a biological sample from a human following administration of an anti-CD200 antibody to the human and (xvi) the concentration of $CD8^+$ lymphocytes of the same histological type as in (xv) in a biological sample from the human prior to administration of the antibody; (i): (xvii) the concentration of CD200+ T cells in a biological sample obtained from a human following administration to the human of an anti-CD200 antibody and (xviii) the concentration of $CD200^+$ T cells of the same histological type as in (xvii) in a biological sample obtained from the human prior to administration of the antibody; (j): (xix) the concentration of $CD200R^+$ T cells in a biological sample obtained from a human following administration to the human of an anti-CD200 antibody and (xx) the concentration of $CD200R^+$ T cells of the same histological type as in (xix) in a biological sample obtained from the human prior to administration of the antibody; (k): (xxi) the concentration of one or more subsets of $CD200^+$ leukocytes in a biological sample obtained from a human following administration to the human of an anti-CD200 antibody and (xxii) the concentration of one or more subsets of $CD200^+$ leukocytes of the same histological type as in (xxi) in a biological sample obtained from the human prior to administration of the antibody; (l): (xxiii) the concentration of one or more subsets of $CD200^+$ bone marrow cells in a biological sample obtained from a human following administration to the human of an anti-CD200 antibody and (xxiv) the concentration of the one or more subsets of $CD200^+$ bone marrow cells of the same histological type as in (xxiii) in a biological sample obtained from the human prior to administration of the antibody; and/or (m): (xxv) the level of expression of CD200 by a plurality of bone marrow cells in a biological sample obtained from the human following administration to the human of an anti-CD200 antibody and (xxvi) the level of expression of CD200 by a plurality of bone marrow cells of the same histological type as in (xxv) in a biological sample obtained from the human prior to administration of the antibody, wherein: (a) a reduction in the post-treatment CD200$^+$ leukocyte concentration as compared to the pre-treatment CD200$^+$ leukocyte concentration indicates that the antibody has produced a desired immunomodulatory effect in the human; (b) an increase in the post-treatment CD200R$^+$ leukocyte concentration as compared to the pre-treatment CD200R$^+$ leukocyte concentration indicates that the antibody has produced a desired immunomodulatory effect in the human; (c) an increase in post-treatment CD200R expression level by the plurality of leukocytes as compared to the pre-treatment CD200R expression level indicates that the antibody has produced a desired immunomodulatory effect in the human; (d) a reduction in post-treatment CD200$^+$ expression level by the plurality of leukocytes as compared to the pre-treatment CD200$^+$ expression level indicates that the antibody has produced a desired immunomodulatory effect in the human; (e) a reduction in the post-treatment concentration of regulatory T cells as compared to the pre-treatment concentration of regulatory T cells indicates that the antibody has produced a desired immunomodulatory effect in the human; (f) an increase in the post-treatment concentration of activated T cells as compared to the pre-treatment activated T cell concentration indicates that the antibody has produced a desired immunomodulatory effect in the human; (g) an increase in the post-treatment ratio of percent activated T cells to percent regulatory T cells as compared to the pre-treatment ratio indicates that the antibody has produced an immunomodulatory effect in the human or a post-treatment ratio of percent activated T cells to percent regulatory T cells of at least 2:1 indicates that the antibody has produced a desired immunomodulatory effect in the human; (h) an increase in the post-treatment concentration of CD8$^+$ lymphocytes as compared to pre-treatment concentration of CD8$^+$ lymphocytes indicates that the antibody has produced a desired immunomodulatory effect in the human; (i) a decrease in the post-treatment concentration of CD200$^+$ T cells as compared to the pre-treatment concentration of CD200$^+$ T cells indicates that the antibody has produced a desired immunomodulatory effect in the human; (j) an increase in the post-treatment concentration of CD200R$^+$ T cells as compared to the pre-treatment concentration of CD200R$^+$ T cells indicates that the antibody has produced a desired immunomodulatory effect in the human; (k) a decrease in the post-treatment concentration of one or more subsets of CD200$^+$ leukocytes as compared to the pre-treatment concentration of the CD200$^+$ leukocytes indicates that the anti-CD200 antibody has produced a desired immunomodulatory effect in the human; (l) a decrease in the post-treatment concentration of one or more subsets of CD200$^+$ bone marrow cells as compared to the pre-treatment concentration of the CD200+ bone marrow cells indicates that the anti-CD200 antibody has produced a desired immunomodulatory effect in the human; or (m) a decrease in the post-treatment CD200 expression by the plurality of bone marrow cells as compared to the pre-treatment CD200 expression level by the plurality indicates that the anti-CD200 antibody has produced a desired immunomodulatory effect in the human. In some embodiments, two or more (e.g., three, four, five, six, seven, eight, or nine or more) of any combination of the conditions are measured. In some embodiments all of the conditions are measured.

In yet another aspect, the disclosure features a computer readable medium comprising a medical profile of a human, the profile comprising information on one or more anti-CD200 antibody-associated immunomodulatory biomarkers, the biomarkers selected from the group consisting of: (a): (i) the concentration of CD200+ leukocytes (e.g., CD200$^+$ T cells) in a biological sample obtained from a human following administration to the human of an anti-CD200 antibody and (ii) the concentration of CD200$^+$ leukocytes (e.g., CD200$^+$ T cells) of the same histological type as in (i) in a biological sample obtained from the human prior to administration of the antibody; (b): (iii) the concentration of CD200R$^+$ leukocytes (e.g., CD200R$^+$ T cells) in a biological sample obtained from a human following administration to the human of an anti-CD200 antibody and (iv) the concentration of CD200R$^+$ leukocytes (e.g., CD200R$^+$ T cells) of the same histological type as in (iii) in a biological sample obtained from the human prior to administration of the antibody; (c): (v) the level of expression of CD200R by a plurality of leukocytes in a biological sample obtained from the human following administration to the human of an anti-CD200 antibody and (vi) the level of expression of CD200R by a plurality of leukocytes of the same histological type as in (v) in a biological sample obtained from the human prior to administration of the antibody; (d): (vii) the level of expression of CD200 by a plurality of leukocytes in a biological sample obtained from the human following administration to the human of an anti-CD200 antibody and (viii) the level of expression of CD200 by a plurality of leukocytes of the same histological type as in (vii) in a biological sample obtained from the human prior to administration of the antibody; (c): (ix) the concentration of regulatory T cells in a biological sample from a human following administration to the human of an anti-CD200 antibody and (x) the concentration of regulatory T cells of the same histological type as in (ix) in a biological sample from the human prior to administration of the anti-CD200 antibody; (f): (xi) the concentration of activated T cells in a biological sample from a human following administration of an anti-CD200 antibody to the human and (xii) the concentration of activated T cells of the same histological type as in (xi) in a biological sample from the human prior to administration of the anti-CD200 antibody; (g): (xiii) the ratio of percent activated T cells to percent regulatory T cells in a biological sample from a human following administration of an anti-CD200 antibody and (xiv) the corresponding ratio of percent activated T cells to percent regulatory T cells (each of the same histological type as in (xiii)) in a biological sample from the human prior to administration of the anti-CD200 antibody; and (h): (xv) the concentration of CD8$^+$ lymphocytes (e.g., T cells) in a biological sample from a human following administration of an anti-CD200 antibody to the human and (xvi) the concentration of CD8$^+$ lymphocytes of the same histological type as in (xv) in a biological sample from the human prior to administration of the antibody. The medical profile can also include, e.g., (xvii) the level of expression of CD200 by a plurality of leukocytes (e.g., bone marrow cells or splenocytes) in a biological sample obtained from a patient following administration of an anti-CD200 antibody and/or (xviii) the level of CD200 expression by a plurality of leukocytes (e.g., bone marrow cells or splenocytes) of the same histological type as in (xvii) in a biological sample obtained from the patient prior to administration of the anti-CD200 antibody. The medical profile can also include, e.g., (xix) the concentration of one or more CD200$^+$ bone marrow cell subsets in a biological sample obtained from a patient following administration of an anti-CD200 antibody and/or (xx) the concentration of one or more CD200$^+$ bone marrow cell subsets of the same histological type in (xix) in a biological sample obtained from the patient prior to administration of the anti-CD200 antibody. In some embodiments, the medical profile can include such information of two or more (e.g., three, four, five, 10, 15, 20, 30, 40, 50, 60, 70, 80, 90, or 100 or more) patients. In some embodiments, the medical profile is stored on a computer-readable medium such as a computer harddrive, flashdrive, DVD, or CD.

In another aspect, the disclosure provides a computer-based method for determining whether an anti-CD200 antibody has produced a desired immunomodulatory effect in a human. The method includes receiving data including a medical profile of a human, the profile comprising information on at least one of the anti-CD200 antibody-associated immunomodulatory biomarkers described herein including: (a): (i) the concentration of $CD200^+$ leukocytes (e.g., $CD200^+$ T cells) in a biological sample obtained from a human following administration to the human of an anti-CD200 antibody and (ii) the concentration of $CD200^+$ leukocytes (e.g., $CD200^+$ T cells) of the same histological type as in (i) in a biological sample obtained from the human prior to administration of the antibody; (b): (iii) the concentration of $CD200R^+$ leukocytes (e.g., $CD200R^+$ T cells) in a biological sample obtained from a human following administration to the human of an anti-CD200 antibody and (iv) the concentration of $CD200R^+$ leukocytes (e.g., $CD200R^+$ T cells) of the same histological type as in (iii) in a biological sample obtained from the human prior to administration of the antibody; (c): (v) the level of expression of CD200R by a plurality of leukocytes in a biological sample obtained from the human following administration to the human of an anti-CD200 antibody and (vi) the level of expression of CD200R by a plurality of leukocytes of the same histological type as in (v) in a biological sample obtained from the human prior to administration of the antibody; (d): (vii) the level of expression of CD200 by a plurality of leukocytes in a biological sample obtained from the human following administration to the human of an anti-CD200 antibody and (viii) the level of expression of CD200 by a plurality of leukocytes of the same histological type as in (vii) in a biological sample obtained from the human prior to administration of the antibody; (e): (ix) the concentration of regulatory T cells in a biological sample from a human following administration to the human of an anti-CD200 antibody and (x) the concentration of regulatory T cells of the same histological type as in (ix) in a biological sample from the human prior to administration of the anti-CD200 antibody; (f): (xi) the concentration of activated T cells in a biological sample from a human following administration of an anti-CD200 antibody to the human and (xii) the concentration of activated T cells of the same histological type as in (xi) in a biological sample from the human prior to administration of the anti-CD200 antibody; (g): (xiii) the ratio of percent activated T cells to percent regulatory T cells in a biological sample from a human following administration of an anti-CD200 antibody and (xiv) the corresponding ratio of percent activated T cells to percent regulatory T cells (each of the same histological type as in (xiii)) in a biological sample from the human prior to administration of the anti-CD200 antibody; and (h): (xv) the concentration of $CD8^+$ lymphocytes (e.g., T cells) in a biological sample from a human following administration of an anti-CD200 antibody to the human and (xvi) the concentration of $CD8^+$ lymphocytes of the same histological type as in (xv) in a biological sample from the human prior to administration of the antibody; and processing at least the portion of the data containing the information to determine whether the antibody has produced a desired immunomodulatory effect in the human, wherein: a reduction in the post-treatment $CD200^+$ leukocyte (e.g., $CD200^+$ T cells) concentration as compared to the pre-treatment CD200+ leukocyte (e.g., $CD200^+$ T cell) concentration indicates that the antibody has produced a desired immunomodulatory effect in the human; an increase in the post-treatment $CD200R^+$ leukocyte (e.g., $CD200R^+$ T cell) concentration as compared to the pre-treatment $CD200R^+$ leukocyte concentration indicates that the antibody has produced a desired immunomodulatory effect in the human; a reduction in post-treatment $CD200^+$ expression level by the plurality of leukocytes as compared to the pre-treatment CD200 expression level indicates that the antibody has produced a desired immunomodulatory effect in the human; an increase in post-treatment CD200R expression level by the plurality of leukocytes as compared to the pre-treatment CD200R expression level indicates that the antibody has produced a desired immunomodulatory effect in the human; a reduction in the post-treatment concentration of regulatory T cells as compared to the pre-treatment concentration of regulatory T cells indicates that the antibody has produced an immunodulatory effect in the human; an increase in the post-treatment concentration of activated T cells as compared to the pre-treatment activated T cell concentration indicates that the antibody has produced a desired immunomodulatory effect in the human; an increase in the post-treatment concentration of $CD8^+$ lymphocytes (e.g., T cells) as compared to pre-treatment concentration of $CD8^+$ lymphocytes indicates that the antibody has produced a desired immunomodulatory effect in the human; and an increase in the post-treatment ratio of percent activated T cells to percent regulatory T cells as compared to the pre-treatment ratio indicates that the antibody has produced a desired immunomodulatory effect in the human; and/or a post-treatment ratio of percent activated T cells to percent regulatory T cells of at least 2:1 (e.g., at least 3:1, 4:1, 5:1, 6:1, or even 7:1 or more) indicates that the antibody has produced a desired immunomodulatory effect in the human.

In another aspect, the disclosure features a computer-based method for determining whether an anti-CD200 antibody has produced a desired immunomodulatory effect in a human, which method includes: providing information on one or both of (a): (i) the concentration of $CD200^+$ leukocytes (e.g., $CD200^+$ T cells) in a biological sample obtained from a human following administration to the human of an anti-CD200 antibody and (ii) the concentration of $CD200^+$ leukocytes (e.g., $CD200^+$ T cells) of the same histological type as in (i) in a biological sample obtained from the human prior to administration of the antibody; (b): (iii) the concentration of $CD200R^+$ leukocytes (e.g., $CD200R^+$ T cells) in a biological sample obtained from a human following administration to the human of an anti-CD200 antibody and (iv) the concentration of $CD200R^+$ leukocytes (e.g., $CD200R^+$ T cells) of the same histological type as in (iii) in a biological sample obtained from the human prior to administration of the antibody; (c): (v) the level of expression of CD200R by a plurality of leukocytes in a biological sample obtained from the human following administration to the human of an anti-CD200 antibody and (vi) the level of expression of CD200R by a plurality of leukocytes of the same histological type as in (v) in a biological sample obtained from the human prior to administration of the antibody; (d): (vii) the level of expression of CD200 by a plurality of leukocytes in a biological sample obtained from the human following administration to the human of an anti-CD200 antibody and (viii) the level of expression of CD200 by a plurality of leukocytes of the same histological type as in (vii) in a biological sample obtained from the human prior to administration of the antibody; (e): (ix) the concentration of regulatory T cells in a biological sample from a human following administration to the human of an anti-CD200 antibody and (x) the concentration of regulatory T cells of the same histological type as in (ix) in a biological sample from the human prior to administration of the anti-CD200 antibody; (f): (xi) the concentration of activated T cells in a biological sample from a human following administration of an anti-CD200 antibody to the human and (xii) the concentration of activated T cells of the same histological type as in (xi) in a biological sample from the human prior to administration of the anti-CD200 antibody; (g): (xiii) the ratio of percent activated T cells to percent regulatory T cells in a biological sample from a human following administration of an anti-CD200 antibody and (xiv) the corresponding ratio of percent activated T cells to percent regulatory T cells (each of the same histological type as in (xiii)) in a biological sample from the human prior to administration of the anti-CD200 antibody; and (h): (xv) the concentration of $CD8^+$ lymphocytes (e.g., T cells) in a biological sample from a human following administration of an anti-CD200 antibody to the human and (xvi) the concentration of $CD8^+$ lymphocytes of the same histological type as in (xv) in a biological sample from the human prior to administration of the antibody; inputting the information into a computer; and calculating a parameter indicating whether the antibody has produced a desired immunomodulatory effect in the human using the computer and the input information, wherein: a reduction in the post-treatment $CD200^+$ leukocyte (e.g., $CD200^+$ T cells) concentration as compared to the pre-treatment $CD200^+$ leukocyte (e.g., $CD200^+$ T cell) concentration indicates that the antibody has produced a desired immunomodulatory effect in the human; an increase in the post-treatment $CD200R^+$ leukocyte (e.g., $CD200R^+$ T cell) concentration as compared to the pre-treatment $CD200R^+$ leukocyte concentration indicates that the antibody has produced a desired immunomodulatory effect in the human; a reduction in post-treatment $CD200R^+$ expression level by the plurality of leukocytes as compared to the pre-treatment $CD200^+$ expression level indicates that the antibody has produced a desired immunomodulatory effect in the human; an increase in post-treatment CD200R expression level by the plurality of leukocytes as compared to the pre-treatment CD200R expression level indicates that the antibody has produced a desired immunomodulatory effect in the human; a reduction in the post-treatment concentration of regulatory T cells as compared to the pre-treatment concentration of regulatory T cells indicates that the antibody has produced an immunodulatory effect in the human; an increase in the post-treatment concentration of activated T cells as compared to the pre-treatment activated T cell concentration indicates that the antibody has produced a desired immunomodulatory effect in the human; an increase in the post-treatment ratio of percent activated T cells to percent regulatory T cells as compared to the pre-treatment ratio indicates that the antibody has produced a desired immunomodulatory effect in the human; an increase in the post-treatment concentration of $CD8^+$ lymphocytes (e.g., T cells) as compared to pre-treatment concentration of $CD8^+$ lymphocytes indicates that the antibody has produced a desired immunomodulatory effect in the human; and/or a post-treatment ratio of percent activated T cells to percent regulatory T cells of at least 2:1 (e.g., at least 3:1, 4:1, 5:1, 6:1, or even 7:1 or more) indicates that the antibody has produced a desired immunomodulatory effect in the human. The method can also include outputting the parameter.

In some embodiments, the information can include: (xvii) the level of expression of CD200 by a plurality of leukocytes (e.g., bone marrow cells or splenocytes) in a biological sample obtained from a patient following administration of an anti-CD200 antibody and/or (xviii) the level of CD200 expression by a plurality of leukocytes (e.g., bone marrow cells or splenocytes) of the same histological type as in (xvii) in a biological sample obtained from the patient prior to administration of the anti-CD200 antibody, wherein a post-treatment decrease in the level of CD200 expression by the plurality, as compared to the pre-treatment level of expression by the corresponding plurality, indicates that the anti-CD200 antibody has produced a desired immunomodulatory effect in the human.

In some embodiments, the information can include: (xix) the concentration of one or more $CD200^+$ bone marrow cell subsets in a biological sample obtained from a patient following administration of an anti-CD200 antibody and/or (xx) the concentration of one or more $CD200^+$ bone marrow cell subsets of the same histological type in (xix) in a biological sample obtained from the patient prior to administration of the anti-CD200 antibody, wherein a post-treatment decrease in the concentration of the one or more $CD200^+$ bone marrow subsets, as compared to the pre-treatment concentration of the corresponding $CD200^+$ bone marrow subsets, indicates that the anti-CD200 antibody has produced a desired immunomodulatory effect in the human.

In some embodiments of any of the methods described herein, the human has, is suspected of having, or is likely to develop, a cancer. The cancer can be, e.g., CLL (e.g., B-CLL). The cancer can be, e.g., a solid tumor such as, but not limited to, a colon cancer, a breast cancer, a lung cancer, a renal cancer, a pancreatic cancer, a thyroid cancer, a skin cancer, a cancer of the nervous system, a cervical cancer, an ovarian cancer, a testicular cancer, a head and neck cancer, a bone cancer, a cancer of the eye, a stomach cancer, or a liver cancer. The cancer of the nervous system can be a neuroblastoma.

In some embodiments of any of the methods described herein, the human has, is suspected of having, or is at risk for developing an inflammatory condition and/or a bone disorder. Inflammatory disorders and bone disorders are well-known in the art of medicine. Examples of each of these disorders are provided herein.

In some embodiments, any of the methods described herein can include administering to the human a therapeutically-effective amount of the anti-CD200 antibody if the antibody has been determined to produce a desired immunomodulatory effect in the human.

In some embodiments, any of the above methods can include administering to the subject the anti-CD200 antibody, e.g., in an amount and with a frequency effective to maintain the immunomodulatory effect in the human.

The inventors have also discovered that upon administration of an anti-CD200 antibody to a patient with a cancer comprising a plurality of CD200-expressing cancer cells, CD200 expression by the cancer cells is reduced. Cancer cells have evolved a number of ways to evade detection by the human immune system, which can identify malignant cells and kill the cells—a process known as immunosurveillance—before a potentially life-threatening cancer develops in the human. See, e.g., Geertsen et al. (1999) *Int J Mol Med* 3(1):49-57; Kerebijn et al. (1999) *Crit. Rev Oncol Hematol* 31(1):31-53; and Pardoll (2003) *Annu Rev Immunol* 21:807-39. One potential mechanism by which cancer cells escape immunosurveillance is via expression or overexpression of the immunosuppressive CD200 protein. In fact, CD200 protein has been shown to be expressed or overexpressed on a variety of human cancer cells including, e.g., B cell chronic lymphocytic leukemia cells, prostate cancer cells, breast cancer cells, colon cancer cells, and brain cancer cells. See, e.g., Kawasaki et al. (2007) *Biochem Biophys Res Commun* 364 (4):778-782; Kretz-Rommel et al. (2007), supra; and Siva et al. (2008) *Cancer Immunol Immunother* 57(7):987-96. Thus, while the disclosure is not bound by any particular theory or mechanism of action, the inventors believe that the anti-CD200 antibody-dependent downregulation of CD200 on the cancer cells relieves an inhibition of immunosurveillance and allows the immune system to more effectively identify and fight the cancer. Accordingly, it is believed to be beneficial to administer to the human an anti-CD200 antibody in an amount and with a frequency sufficient to sustain the reduced expression of CD200 by the cancer cells in the human. Exemplary anti-CD200 antibody dosing schedules in accordance with the disclosure are provided herein. Two non-exhaustive, non-limiting examples of such a dosing schedule are administration of the anti-CD200 antibody in a higher amount (e.g., greater than 200 mg/m$^2$) and/or at a lower amount (e.g., less than or equal to 200 mg/m$^2$), but with an increased frequency (e.g., at least once every 12 days). Additional examples are provided herein.

Furthermore, as elaborated on in the working examples set forth herein, the inventors further report a discovery based on the observed pharmacodynamic properties of the anti-CD200 antibody samalizumab administered to a patient on a once per month dosing schedule. Specifically, under the once per month dosing schedule at a dose of between (and inclusive of) 50 mg/m$^2$ to 200 mg/m$^2$, the immunomodulatory effect of the antibody in the patients was transient, with affected cell populations recovering (or nearly recovering) to pre-treatment levels at around day 14. Administration of the second dose of samalizumab, however, once again produced the immunomodulatory effect on the specific cell populations (e.g., CD200$^+$ cancer cells, CD200$^+$ T cells, etc.). Administration of a higher dose (e.g., 300 mg/m$^2$ to 500 mg/m$^2$) resulted in a more sustained immunomodulatory effect in the human. Thus, the inventors concluded that administration of the antibody at a higher amount and/or with an increased frequency to thereby sustain the immunomodulatory effect in patients will be more effective to treat a disease (e.g., a cancer, a bone disorder, or an inflammatory disorder) in a human.

Accordingly, in yet another aspect, the disclosure features a method for treating a human with cancer, which method includes administering to the human an anti-CD200 antibody in an amount and/or with a frequency effective to treat the cancer if the anti-CD200 antibody is determined to have produced an anti-CD200 antibody-associated immunomodulatory effect in the human. The determining can include, e.g., any of the methods described herein for determining whether an anti-CD200 antibody has produced a desired immunomodulatory effect in a human.

In another aspect, the disclosure features a method for treating a patient afflicted with cancer, the method comprising: administering to a patient in need thereof an anti-CD200 antibody in an amount and with a frequency effective to maintain an anti-CD200 antibody-associated immunomodulatory effect in the human to thereby treat the patient's cancer. The immunomodulatory effect can be indicated by, e.g., a change in one or more of any of the anti-CD200 antibody-associated immunomodulatory biomarkers described herein including the concentration of one or more CD200$^+$ bone marrow cell subsets and the level of CD200 expression by splenocytes or bone marrow cells (see below). In some embodiments, the immunomodulatory biomarkers do not include the concentration of one or more CD200$^+$ bone marrow cell subsets and/or the level of CD200 expression by bone marrow cells.

In some embodiments of any of the methods described herein, the antibody can be administered to the patient in an amount and with a frequency effective to maintain in the patient one or more of the following conditions (e.g., as determined by an analysis (e.g., a measurement, detection, or quantitation) of a biological sample from the patient): (i) a reduced concentration of regulatory T cells, relative to the concentration of regulatory T cells of the same histological type in the patient prior to the first administration of the antibody; (ii) an increased concentration of CD8$^+$ lymphocytes (e.g., T cells), relative to the concentration of CD8$^+$ lymphocytes of the same histological type in the patient prior to the first administration of the antibody; (iii) an increased concentration of activated T cells, relative to the concentration of activated T cells of the same histological type in the patient prior to the first administration of the antibody; (iv) a reduced concentration of CD200$^+$ lymphocytes (e.g., T cells), relative to the concentration of CD200$^+$ lymphocytes of the same histological type in the patient prior to the first administration of the antibody; (v) an increase in the concentration of CD200R$^+$ lymphocytes (e.g., T cells), relative to the concentration of CD200R$^+$ lymphocytes of the same histological type in the patient prior to the first administration of the antibody; (vi) an increase in the ratio of percent activated T cells to percent regulatory T cells, relative to the corresponding ratio of a ratio in the patient prior to the first administration of the antibody; (vii) a ratio of percent activated T cells to percent regulatory T cells (T regs) of at least 2:1 (e.g., at least 3:1, at least 4:1, at least 5:1, at least 6:1, or at least 7:1), relative to the ratio of activated T cells to T regs in the patient prior to the first administration of the antibody; (viii) a reduction in the level of CD200 expression by the plurality of leukocytes as compared to the level of CD200 expression by a plurality of leukocytes of the same histological type in the patient prior to the first administration of the antibody; (ix) an increase in the level of CD200R expression by a plurality of leukocytes as compared to the CD200R expression level by a plurality of leukocytes of the same histological type in the patient prior to the first administration of the antibody; and (x), in embodiments where the cancer comprises a plurality of cells that express (or overexpress) CD200, a reduction in the level of CD200 expression by a plurality of the CD200$^+$ cancer cells, relative to the level of CD200 expression by a corresponding plurality of CD200$^+$ cancer cells prior to the first administration of the anti-CD200 antibody. In embodiments where an anti-CD200 antibody has been administered to the patient two or more times, it is understood that evaluation of one or more of the above parameters can be (but need not necessarily be) relative (or as compared to) the corresponding value of the parameter prior to the first dose of the anti-CD200 antibody, the most recent administration of the anti-CD200 antibody, or between doses of the anti-CD200 antibody administered to the patient. For example, in embodiments where a patient has been administered over time five (5) doses of an anti-CD200 antibody, a decrease in the concentration of CD200$^+$ lymphocytes (e.g., T cells), relative to the concentration of CD200$^+$ lymphocytes of the same histological type in the patient prior to the fifth administration of the antibody can indicate that a desired immunomodulatory effect has occurred in the patient as the result of administration of the antibody.

In some embodiments, the anti-CD200 antibody is administered to the patient in an amount and with a frequency to maintain all of the foregoing conditions in the patient for the course of the cancer treatment. In some embodiments, the antibody is administered to the patient for at least four weeks (e.g., at least five weeks, six weeks, seven weeks, eight weeks, two months, three months, four months, five months, six months, seven months, eight months, nine months, 10 months, 11 months, one year, 13 months, 14 months, 15 months, 16 months, one and a half years, two years, three years, or four years or more).

In some embodiments, the cancer treatment methods described herein can include administering an anti-CD200 antibody, e.g., a whole antibody, to a patient in need thereof at an individual dose of greater than or equal to 100 (e.g., greater than or equal to 150, 175, 200, 225, 250, 275, 300, 325, 350, 375, 400, 425, 450, 475, 500, 525, 550, 575, or 600) mg/m$^2$ with a frequency of at least about once every week (e.g., at least once every seven days, eight days, nine days, 10 days, 11 days, 12 days, 13 days, 14 days, 15 days, 16 days, 17 days, 18 days, 19 days, or 20 days), depending on the particular patient. In some embodiments, the anti-CD200 antibody can be administered to the patient at least once per week (e.g., at least once every two weeks or three weeks). In some embodiments, an individual dose of the anti-CD200 antibody can be between (and inclusive of) 100 to 600 (e.g., between (and inclusive of) 150 to 600, 200 to 600, 300 to 600, 100 to 500, 100 to 400, 100 to 300, 100 to 200, 200 to 500, 200 to 400, 200 to 300, 300 to 500, 400 to 500, or 300 to 500) mg/m$^2$ and can be, in some embodiments, administered to a patient, e.g., at least once every seven days. In some embodiments, a patient can receive one dose of an anti-CD200 antibody described herein once every day (e.g., every two days, or every three days). As described above, it is understood that depending on the individual patient parameters (e.g., height, weight, gender, severity of disease, age, co-morbidities, and additional medications), one or both of the frequency and the amount of the anti-CD200 antibody can be modified to maintain the immunomodulatory effect in the human. Methods for determining the appropriate dosing strategy for maintaining one or more of the immunomodulatory effect conditions in the patient are described herein (infra).

In another aspect, the disclosure provides a method for treating cancer, which includes administering to a patient afflicted with a cancer an anti-CD200 antibody in an amount and with a frequency effective to maintain an increased concentration of activated T cells in the patient, as compared to the concentration of activated T cells in the patient prior to administration of the antibody, to thereby treat the cancer. The method can also include after administering the anti-CD200 antibody to the human, determining whether the concentration of activated T cells has been increased in the patient.

In another aspect, the disclosure also features a method for treating cancer, wherein the method includes administering to a patient afflicted with cancer an anti-CD200 antibody in an amount and with a frequency effective to maintain in the patient a reduced concentration of regulatory T cells, as compared to the concentration of regulatory T cells in the patient prior to administration of the anti-CD200 antibody, to thereby treat the cancer.

In another aspect, the disclosure also features a method for treating cancer, the method comprising administering to a patient afflicted with a cancer an anti-CD200 antibody in an amount and with a frequency effective to maintain in the patient (e.g., as determined by an analysis of a biological sample obtained from the patient after administration of the antibody) a ratio of percent activated T cells to percent regulatory T cells (T regs) of at least 2:1 (e.g., at least 3:1, at least 4:1, at least 5:1, at least 6:1, or at least 7:1).

In some embodiments of any of the methods described herein, the regulatory T cells can be, e.g., CD3$^+$CD4$^+$CD25$^+$FoxP3$^+$ T cells or CD3$^+$CD4$^+$FoxP3$^+$ T cells. In some embodiments of any of the methods described herein, the activated T cells can be, e.g., CD3$^+$CD4$^+$CD25$^+$FoxP3$^{neg}$ T cells or CD3$^{+CD}$4$^+$FoxP3$^{neg}$ T cells.

In yet another aspect, the disclosure features a method for determining an anti-CD200 antibody dosing schedule for treating a patient determined by a medical practitioner to be one who will, or is likely to, benefit from an anti-CD200 antibody therapy (e.g., a patient suffering from a cancer, a bone disease, or an inflammatory disorder). The method comprises, e.g., establishing a peak level or maximum level of a desired immunomodulatory effect produced in a patient following administration of an anti-CD200 antibody and monitoring the patient (e.g., by way of analysis of a biological sample from the patient) for a change away from that peak level of effect, wherein the timing of that change in that peak level of effect (e.g., the duration of time that the peak level of effect is maintained in a patient at a given dose before an additional dose is required to maintain that peak level of effect) determines the dosing schedule for the patient in that a medical practitioner determines the amount of the anti-CD200 antibody and/or frequency of administration of the antibody that is necessary to maintain the peak level of immunomodulatory effect in the patient for the duration of treatment. In some embodiments, an additional dose (at a higher dose and/or sooner than originally predetermined) of the anti-CD200 antibody is administered to the patient if the level of immunomodulatory effect changes by at least 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % from the peak immunomodulatory effect observed for the patient. For example, a medical practitioner can observe that upon administration of the first dose of an anti-CD200 antibody, the concentration of CD200$^+$ leukocytes decreases to a post-treatment concentration X, the concentration X representing the peak level of immunomodulatory effect in the patient. When the practitioner observes that the post-treatment concentration of the CD200$^+$ leukocytes increases by at least 5% (supra) from X, the practitioner can elect to administer an additional dose of the anti-CD200 antibody (at a higher amount or at the same amount as the initial dose, but sooner than the practitioner had anticipated) to the patient to thereby restore and maintain the concentration of CD200$^+$ leukocytes at the concentration X or below.

Thus, in some embodiments, the methods for determining an anti-CD200 antibody dosing schedule can include monitoring the level of a desired anti-CD200 antibody-associated immunomodulatory effect in a patient who has been administered an anti-CD200 antibody to thereby determine for the patient a dosing schedule of the antibody, wherein the dosing schedule is sufficient to maintain the immunomodulatory effect in the patient for the duration of the treatment with the antibody. The occurrence of a change in the peak level of immunomodulatory effect in the patient can be the trigger for administering to the patient a higher dose of the anti-CD200 antibody and/or administering the anti-CD200 antibody to the patient more frequently to thereby maintain the peak level of immunomodulatory effect in the patient and thereby determine a dosing schedule for the antibody that achieves such maintenance.

In some embodiments, the methods can include administering to the patient an anti-CD200 antibody to thereby produce in the patient an anti-CD200 antibody-associated immunomodulatory effect (e.g., as indicated by a change (e.g., an increase or decrease) in one or more of the anti-CD200 antibody-associated biomarkers in a biological sample from the patient). In some embodiments, one or more (e.g., two, three, four, five, six, seven, eight, nine, or 10 or more) of the following changes in the biomarkers can be monitored: (i) a reduced concentration of regulatory T cells, relative to the concentration of regulatory T cells of the same histological type in the human prior to the first administration of the antibody; (ii) an increased concentration of CD8$^+$ leukocytes (e.g., T cells), relative to the concentration of CD8$^+$ leukocytes of the same histological type in the human prior to the first administration of the antibody; (iii) an increased concentration of activated T cells, relative to the concentration of activated T cells of the same histological type in the human prior to the first administration of the antibody; (iv) a reduced concentration of CD200$^+$ leukocytes (e.g., CD200$^+$ T cells), relative to the concentration of CD200$^+$ leukocytes of the same histological type in the human prior to the first administration of the antibody; (v) an increase in the concentration of CD200R$^+$ leukocytes (e.g., CD200R$^+$ T cells), relative to the concentration of CD200R$^+$ leukocytes of the same histological type in the human prior to the first administration of the antibody; and (vi) a ratio of percent activated T cells to percent regulatory T cells (T regs) of at least 2:1 (e.g., at least 3:1, at least 4:1, at least 5:1, at least 6:1, or at least 7:1), relative to the ratio of activated T cells to T regs in the human prior to the first administration of the antibody. Additional changes that can be monitored as described herein. For example, in some embodiments, a post-treatment decrease in the concentration of one or more CD200$^+$ bone marrow subsets, as compared to the pre-treatment concentration of the corresponding CD200$^+$ bone marrow subsets, indicates that the anti-CD200 antibody has produced a desired immunomodulatory effect in the human. In some embodiments, a post-treatment decrease in the level of CD200 expression by a plurality of splenocytes and/or bone marrow cells (e.g., bone marrow cell subsets), as compared to the pre-treatment level of expression by the corresponding plurality, indicates that the anti-CD200 antibody has produced a desired immunomodulatory effect in the human. It is understood that the monitoring can comprise, e.g., measuring the concentration of the appropriate selected cell type (e.g., CD200$^+$ or CD200R$^+$ leukocytes); quantifying the level of expression of one or more expression markers such as CD200; or determining the ratio of percent activated T cells to percent regulatory T cells. In some embodiments, even a partial reversal of the status of one or more of these anti-CD200 antibody-associated biomarkers indicates that a medical practitioner should increase the amount of the anti-CD200 antibody administered to the patient and/or increase the frequency of administration of the anti-CD200 antibody to the patient, to thereby maintain in the patient the anti-CD200 antibody-associated immunomodulatory effect.

In another aspect, the disclosure features a method for determining a dosing schedule for treating a patient suffering from a cancer using an anti-CD200 antibody, the method comprising: providing a patient suffering from a cancer comprising a plurality of cancer cells expressing CD200; administering to the patient an anti-CD200 antibody to thereby reduce the expression of CD200 by the cancer cells; and monitoring the CD200 expression level by the cancer cells to thereby determine for the patient a dosing schedule of the antibody, wherein the dosing schedule is sufficient to maintain a reduced CD200 expression level (e.g., as compared to the pretreatment level) by the cancer cells, e.g., for the duration of the treatment with the antibody. In some embodiments, the CD200 expression level by the cancer cells can be reduced by at least 10 (e.g., at least 15, 20, 25, 30, 35, 40, 45, 50, 55, 60, 65, 70, 75, 80, 85, or 90 or more) %.

In another aspect, the disclosure features a method for determining the dosing schedule for treating a patient suffering from a cancer using an anti-CD200 antibody, the method comprising: administering to a patient suffering from a cancer an anti-CD200 antibody to thereby reduce the concentration of CD200$^+$ leukocytes (e.g., CD200$^+$ T cells) as measured in a blood sample obtained from the patient as compared to the concentration of CD200$^+$ T cells in a control sample; and monitoring the concentration of CD200$^+$ leukocytes (e.g., CD200$^+$ T cells) in the patient to thereby determine for the patient a dosing schedule of the antibody, wherein the dosing schedule is sufficient to maintain a reduced concentration of the CD200$^+$ T cells in the patient for the duration of the treatment of cancer with the antibody. In some embodiments, the concentration of CD200$^+$ leukocytes (e.g., CD200$^+$ T cells) can be reduced by at least 10 (e.g., at least 15, 20, 25, 30, 35, 40, 45, 50, 55, 60, 65, 70, 75, 80, 85, or 90 or more) %. In some embodiments, the CD200$^+$ leukocytes (e.g., CD200$^+$ T cells) are selected from the group consisting of CD200$^+$/CD4$^+$ T cells, activated CD200$^+$/CD4$^+$ T cells, or CD200$^+$/CD8$^+$ T cells.

In another aspect, the disclosure features a method for determining the dosing schedule for treating a patient suffering from a cancer using an anti-CD200 antibody, the method comprising: administering to a patient suffering from a cancer an anti-CD200 antibody to thereby reduce the level of expression of CD200 by leukocytes in a blood sample obtained from the patient as compared to a control expression level of CD200 by leukocytes of the same histological type in a control sample; and monitoring the expression level of CD200 by leukocytes in the patient to thereby determine for the patient a dosing schedule of the antibody, wherein the dosing schedule is sufficient to maintain a reduced level of expression of CD200 by the leukocytes (reduced as compared to the control sample) in the patient for the duration of the treatment of cancer with the antibody. In some embodiments, the level of CD200 expression by the leukocytes can be reduced by at least 10 (e.g., at least 15, 20, 25, 30, 35, 40, 45, 50, 55, 60, 65, 70, 75, 80, 85, or 90 or more) %. In some embodiments, the CD200$^+$ leukocytes are selected from the group consisting of CD200$^+$/CD4+ T cells, activated CD200$^+$/CD4$^+$ T cells, or CD200$^+$/CD8$^+$ T cells.

In another aspect, the disclosure features a method for determining the dosing schedule for treating a patient suffering from a cancer using an anti-CD200 antibody, the method comprising: administering to a patient suffering from a cancer an anti-CD200 antibody to thereby increase the concentration of CD200R$^+$ leukocytes as measured in a blood sample obtained from the patient as compared to the concentration of CD200R$^+$ leukocytes in a control sample; and monitoring the concentration of CD200R$^+$ leukocytes in the patient to thereby determine for the patient a dosing schedule of the antibody, wherein the dosing schedule is sufficient to maintain an increased concentration of the CD200R$^+$ leukocytes (increased as compared to the control sample) in the patient for the duration of the treatment of cancer with the antibody. In some embodiments, the concentration of CD200R$^+$ leukocytes can be increased by at least 10 (e.g., at least 15, 20, 25, 30, 35, 40, 45, 50, 55, 60, 65, 70, 75, 80, 85, 90, 95, or 100 or more) %. In some embodiments, the CD200R$^+$ T cells are selected from the group consisting of CD200R$^+$/CD4$^+$ T cells and activated CD200R$^+$/CD4$^+$ T cells.

In yet another aspect, the disclosure features a method for determining the dosing schedule for treating a patient suffering from a cancer using an anti-CD200 antibody, the method comprising: administering to a patient suffering from a cancer an anti-CD200 antibody to thereby increase the level of expression of CD200R by leukocytes as measured in a blood sample obtained from the patient as compared to a control expression level of CD200R by leukocytes of the same histological type in a control sample; and monitoring the expression level of CD200R by leukocytes in the patient to thereby determine for the patient a dosing schedule of the antibody, wherein the dosing schedule is sufficient to maintain an increased level of expression of CD200R (e.g., as compared to the pre-treatment expression level) by the leukocytes in the patient for the duration of the treatment of cancer with the antibody. In some embodiments, the level of CD200R expression by the leukocytes can be increased by at least 10 (e.g., at least 15, 20, 25, 30, 35, 40, 45, 50, 55, 60, 65, 70, 75, 80, 85, 90, 95, or 100 or more) %. In some embodiments, the leukocytes are T cells such as CD4$^+$ T cells or activated CD4$^+$ T cells.

In yet another aspect, the disclosure features a method for treating a human suffering from a cancer comprising a plurality of cancer cells expressing CD200, the method comprising administering to a human in need thereof an anti-CD200 antibody in an amount and with a frequency sufficient to reduce the CD200 expression level (e.g., as compared to the pre-treatment expression level) by the cancer cells to thereby treat the human's cancer. The method can also include monitoring the human for a reduction in the CD200 expression level by the cancer cells.

In another aspect, the disclosure also features a method for treating a human suffering from a cancer, the method comprising administering to a human in need thereof an anti-CD200 antibody in an amount and with a frequency sufficient to reduce the concentration of CD200$^+$ leukocytes (e.g., T cells) in the blood of a cancer patient to thereby treat the human's cancer. The method can also include monitoring the human for a reduction in the CD200$^+$ leukocytes in the blood of the patient.

In another aspect, the disclosure features a method for treating a human suffering from a cancer, the method comprising administering to a human in need thereof an anti-CD200 antibody in an amount and with a frequency sufficient to result in an increase in the concentration of CD200R$^+$ leukocytes in the blood of a cancer patient to thereby treat the human's cancer. The method can include monitoring the human for a reduction in the CD200$^+$ leukocytes in the blood of the patient.

In another aspect, the disclosure features a method for treating a human suffering from a cancer, the method comprising administering to a human in need thereof an anti-CD200 antibody in an amount and with a frequency sufficient to reduce the expression level of CD200 by T cells in the blood of a cancer patient to thereby treat the human's cancer. The method can also include monitoring the human for a reduction in the expression level of CD200 by T cells in the blood of the patient.

In another aspect, the disclosure features a method for treating a human suffering from a cancer, the method comprising administering to a human in need thereof an anti-CD200 antibody in an amount and with a frequency sufficient to result in an increase in the expression level of CD200R by leukocytes in the blood of a cancer patient to thereby treat the human's cancer. The method can also include monitoring the human for a reduction in the expression level of CD200R by leukocytes in the blood of the patient.

In some embodiments of any of the above methods, the cancer can be one that comprises a plurality of cancer cells expressing CD200. In some embodiments of any of the methods described herein, the cancer is one that comprises a plurality of cancer cells that, relative to non-cancer cells of the same histological type, overexpresses CD200.

In some embodiments of any of the methods described herein, the subject (e.g., the human or the patient) is one who does not have chronic lymphocytic leukemia (CLL) such as B cell CLL.

In some embodiments of the methods described herein, a single dose of an anti-CD200 antibody is sufficient to produce a desired immunomodulatory effect in a human. In some embodiments, a single dose of an anti-CD200 antibody is sufficient to produce a clinically meaningful effect on a patient's cancer. In some embodiments of the methods for treatment described herein, two or more (e.g., three, four, five, six, seven, eight, nine, or 10 or more) doses of the anti-CD200 antibody are administered to a patient in need thereof, e.g., to treat the patient's cancer, inflammatory disorder, or bone disorder. In embodiments in which two or more doses of the antibody are administered to a human (e.g., a patient), each of the two or more doses can be administered at least 7 (e.g., 8, 9, 10, 11, 12, 13, 14, 15, 16, 17, 18, 19, 20, 21, 22, 23, 24, 25, 26, 27, 28, 29, or 30 or more) days apart. In some embodiments, the two or more doses are administered to the patient over the course of at least one (e.g., at least two, three, four, five, or six) month(s). For example, a medical practitioner may elect to administer at least four doses of an anti-CD200 antibody to a cancer patient, each of the doses to be administered once every two weeks (14 days) for two months. It is understood that the medical practitioner can elect to continue treatment under the same or a different dosing schedule.

In yet another aspect, the disclosure features a method for treating a patient afflicted with a disorder selected from the group consisting of a bone disorder and an inflammatory disorder, the method comprising: administering to a patient in need thereof an anti-CD200 antibody in an amount and with a frequency effective to maintain an anti-CD200 antibody-associated immunomodulatory effect in the human to thereby treat the patient's disorder. The immunomodulatory effect can be indicated by, e.g., any of the anti-CD200 antibody-associated immunomodulatory biomarkers described herein. That is, in some embodiments, the antibody can be administered to the patient in an amount and with a frequency effective to maintain in the patient one or more of the following conditions (e.g., as determined by an analysis (e.g., a measurement, detection, or quantitation) of a biological sample from the patient): (i) a reduced concentration of regulatory T cells, relative to the concentration of regulatory T cells of the same histological type in the patient prior to the first administration of the antibody; (ii) an increased concentration of CD8$^+$ lymphocytes (e.g., T cells), relative to the concentration of CD8 lymphocytes of the same histological type in the patient prior to the first administration of the antibody; (iii) an increased concentration of activated T cells, relative to the concentration of activated T cells of the same histological type in the patient prior to the first administration of the antibody; (iv) a reduced concentration of CD200$^+$ lymphocytes (e.g., T cells), relative to the concentration of CD200$^+$ lymphocytes of the same histological type in the patient prior to the first administration of the antibody; (v) an increase in the concentration of CD200R$^+$ lymphocytes (e.g., T cells), relative to the concentration of CD200R$^+$ lymphocytes of the same histological type in the patient prior to the first administration of the antibody; (vi) an increase in the ratio of percent activated T cells to percent regulatory T cells, relative to the corresponding ratio in the patient prior to the first administration of the antibody; (vii) a ratio of percent activated T cells to percent regulatory T cells (T regs) of at least 2:1 (e.g., at least 3:1, at least 4:1, at least 5:1, at least 6:1, or at least 7:1), relative to the ratio of activated T cells to T regs in the patient prior to the first administration of the antibody; (viii) a reduction in the level of CD200 expression by the plurality of leukocytes as compared to the level of CD200 expression by a plurality of leukocytes of the same histological type in the patient prior to the first administration of the antibody; and (ix) an increase in the level of CD200R expression by a plurality of leukocytes as compared to the CD200R expression level by a plurality of leukocytes of the same histological type in the patient prior to the first administration of the antibody. In some embodiments, a post-treatment decrease in the concentration of one or more $CD200^+$ bone marrow subsets, as compared to the pre-treatment concentration of the corresponding $CD200^+$ bone marrow subsets, indicates that the anti-CD200 antibody has produced a desired immunomodulatory effect in the human. In some embodiments, a post-treatment decrease in the level of CD200 expression by a plurality of splenocytes and/or bone marrow cells (e.g., bone marrow cell subsets), as compared to the pre-treatment level of expression by the corresponding plurality, indicates that the anti-CD200 antibody has produced a desired immunomodulatory effect in the human. In embodiments in which an anti-CD200 antibody has been administered to the patient two or more times, it is understood that evaluation of one or more of the above parameters can be (but need not necessarily be) relative (or as compared to) the corresponding value of the parameter prior to the first dose of the antibody, the most recent administration of the anti-CD200 antibody, or between two administered doses of the antibody. For example, in embodiments where a patient has been administered over time five (5) doses of an anti-CD200 antibody, a decrease in the concentration of $CD200^+$ lymphocytes (e.g., T cells), relative to the concentration of $CD200^+$ lymphocytes of the same histological type in the patient prior to the fifth administration of the antibody can indicate that a desired immunomodulatory effect has occurred in the patient as the result of administration of the antibody. For example, in embodiments where a patient has been administered over time five (5) doses of an anti-CD200 antibody, a decrease in the concentration of CD200+ lymphocytes (e.g., T cells), relative to the concentration of $CD200^+$ lymphocytes of the same histological type in the patient after the third administration of the antibody, but prior to the fourth administration of the antibody, can indicate that a desired immunomodulatory effect has occurred in the patient as the result of administration of the antibody.

In another aspect, the disclosure also features a method for treating a human suffering from a bone disorder or an inflammatory disorder, the method comprising administering to a human in need thereof an anti-CD200 antibody in an amount and with a frequency sufficient to reduce the concentration of $CD200^+$ T cells in the blood of the human to thereby treat the human's bone disorder or an inflammatory disorder. The method can also include monitoring for a reduction in the $CD200^+$ T cells in the blood of the human.

In another aspect, the disclosure features a method for treating a human suffering from a bone disorder or an inflammatory disorder, the method comprising administering to a human in need thereof an anti-CD200 antibody in an amount and with a frequency sufficient to result in an increase in the concentration of $CD200R^+$ leukocytes in the blood of the human to thereby treat the human's bone disorder or an inflammatory disorder. The method can include monitoring for a reduction in the $CD200^+$ leukocytes in the blood of the human.

In another aspect, the disclosure features a method for treating a human suffering from a bone disorder or an inflammatory disorder, the method comprising administering to a human in need thereof an anti-CD200 antibody in an amount and with a frequency sufficient to reduce the expression level of CD200 by T cells in the blood of the human to thereby treat the human's bone disorder or an inflammatory disorder. The method can also include monitoring for a reduction in the expression level of CD200 by T cells in the blood of the human.

In another aspect, the disclosure features a method for treating a human suffering from a bone disorder or an inflammatory disorder, the method comprising administering to a human in need thereof an anti-CD200 antibody in an amount and with a frequency sufficient to result in an increase in the expression level of CD200R by leukocytes in the blood of the human to thereby treat the human's bone disorder or an inflammatory disorder. The method can also include monitoring for a reduction in the expression level of CD200R by leukocytes in the blood of the human.

In another aspect, the disclosure also features a method for treating a human suffering from a bone disorder or an inflammatory disorder, the method comprising administering to a human in need thereof an anti-CD200 antibody in an amount and with a frequency sufficient to reduce the concentration of $CD200^+$ T cells in the blood of the human to thereby treat the human's bone disorder or an inflammatory disorder. The method can also include monitoring for a reduction in the $CD200^+$ T cells in the blood of the human.

In another aspect, the disclosure also features a method that results in reducing the concentration of $CD200^+$ leukocytes (e.g., T cells such as $CD4^+$ T cells) in the blood of a patient, the method comprising administering to a patient in need thereof an anti-CD200 antibody in an amount effective to reduce the concentration of CD200+ leukocytes in the blood of the patient. The patient can have, be suspected of having, or be at risk for developing a cancer, an inflammatory disorder, or a bone disorder.

In another aspect, the disclosure also features a method that results in an increase in the concentration of $CD200R^+$ leukocytes (e.g., T cells such as $CD4^+$ T cells) in the blood of a patient, the method comprising administering to a patient in need thereof an anti-CD200 antibody in an amount effective to result in an increase in the concentration of $CD200R^+$ leukocytes (e.g., T cells such as $CD4^+$ T cells) in the blood of the patient. The patient can have, be suspected of having, or be at risk for developing a cancer, an inflammatory disorder, or a bone disorder.

In another aspect, the disclosure also features a method for reducing the expression of CD200 by leukocytes (e.g., T cells such as $CD4^+$ T cells) in the peripheral blood of a patient, the method comprising administering to a patient in need thereof an anti-CD200 antibody in an amount effective to reduce the expression of CD200 by leukocytes in the blood of the patient. The patient can have, be suspected of having, or be at risk for developing a cancer, an inflammatory disorder, or a bone disorder.

In another aspect, the disclosure also features a method that results in an increase in the expression of CD200R by leukocytes (e.g., T cells such as CD4+ T cells) in the blood of a patient, the method comprising administering to a patient in need thereof an anti-CD200 antibody in an amount effective to result in an increase in the expression of CD200R by leukocytes in the blood of the patient. The patient can have, be suspected of having, or be at risk for developing a cancer, an inflammatory disorder, or a bone disorder.

In yet another aspect, the disclosure features a method for increasing the concentration of activated T cells in a patient in need thereof (e.g., a cancer patient), the method comprising administering to the patient an anti-CD200 antibody in an amount and with a frequency effective to increase the concentration of activated T cells in the patient.

In another aspect, the disclosure features a method for decreasing the concentration of regulatory T cells in a patient in need thereof (e.g., a cancer patient), the method comprising administering an anti-CD200 antibody to the patient in an amount and with a frequency effective to reduce the concentration of regulatory T cells in the patient.

In another aspect, the disclosure features a method for increasing the ratio of percent activated T cells to percent regulatory T cells in a patient in need thereof (e.g., a cancer patient), the method comprising administering to the patient an anti-CD200 antibody in an amount and with a frequency effective to increase the ratio of percent activated T cells to percent regulatory T cells in the patient. In some embodiments, the ratio of percent activated T cells to percent regulatory T cells is increased to at least 2:1 (e.g., at least 3:1, 4:1, 5:1, 6:1, or even 7:1 or higher).

In some embodiments of any of the above methods, the cancer (or the patient is afflicted with a cancer that) comprises a plurality of cancer cells expressing CD200. In some embodiments, the cancer (or the patient is afflicted with a cancer that) comprises a plurality of cells that, relative to non-cancer cells of the same histological type as the cells from which cancer is derived, overexpress CD200.

In some embodiments, any of the above treatment methods can be practiced in conjunction with any of the methods described herein for determining whether an anti-CD200 antibody has produced a desired immunomodulatory effect in a human.

The inventors have also discovered an inverse correlation between the peripheral tumor load (e.g., B CLL tumor cell load) and the concentration of T cells present in cancer patients. That is, the greater the concentration of non-cancer T cells present in a cancer patient, the lower the tumor burden in the patient. While the discovery is not limited by any particular theory or mechanism of action, the inventors believe that a cancer patient may receive an enhanced benefit from an anti-CD200 antibody therapy if the cancer patient has normal or elevated levels of normal T cells in his or her body at the time of therapy. In other words, the inventors have determined that an anti-CD200 antibody therapy will likely have more efficacy and/or a stronger immunomodulatory effect in patients with an intact immune system (or not immunocompromised), e.g., an immune system that is capable of mounting an immune response against a cancer present in the patient. As described below, all four of the cancer patients who had not received prior chemotherapy before samalizumab treatment had clinically stable or improved disease after samalizumab treatment. In fact, patient 102-502, who had not received an immunosuppressive or chemotherapeutic therapy prior to administration of the anti-CD200 antibody, exhibited a marked reduction in tumor burden, which correlated with changes in a number of the biomarkers described herein, including, a marked reduction in the concentration of $CD45^+$ B CLL cells, an increase in $CD8^+$ T cells, a decrease in regulatory T cells, an increase in activated T cells, and an increase in the ratio of percent activated T cells to percent regulatory T cells.

Accordingly, in some embodiments of any of the methods described herein (e.g., the methods for treatment, e.g., methods for treating cancer described herein), the subject (e.g., the patient or the human) is one that has not received an immunosuppressive therapy and/or a chemotherapeutic therapy prior to administration of the anti-CD200 antibody. Examples of chemotherapeutic and immunosuppressive therapies are described herein and known in the art. In some embodiments, the subject or patient or human has not received an immunosuppressive or chemotherapeutic therapy less than two months (e.g., less than eight weeks, seven weeks, six weeks, five weeks, a month, 30 days, 25 days, 20 days, 15 days, or 10 days) prior to administration of the first dose of the anti-CD200 antibody.

In some embodiments of any of the methods described herein, the subject is one that has an immune system that is competent to mount an immune response against the subject's cancer. That is, the subject (e.g., the patient) is not immunocompromised. In some embodiments, the subject has not received a chemotherapeutic agent or any other agent capable of suppressing the immune system of the patient less than two months before the first dose of an anti-CD200 antibody is administered to the patient. In some embodiments, the patient is one who is not infected with HIV as determined by, e.g., any of one of several commercially available tests for HIV infection. In some embodiments, the patient is one who does not have an active HIV infection.

In some embodiments, a patient's immune system can be competent to mount an immune response to a cancer only in the presence of the anti-CD200 antibody (that is, with the aid of the immunomodulatory effect produced by the antibody following administration to the subject). In some embodiments, the subject's immune system is competent to mount an immune response to the cancer even in the absence of the anti-CD200 antibody—the antibody enhancing the ability of the immune system to mount an immune response against the cancer. One method for determining whether the subject's immune system is competent to mount an immune response is to determine the concentration of $CD3^+$ cells in the subject's blood. Additional methods are known in the art and described herein.

In another aspect, the disclosure features a method for selecting a cancer patient for treatment with an anti-CD200 antibody, wherein the method comprises determining whether the patient is immunocompetent, and if the cancer patient is immunocompetent, administering an anti-CD200 antibody to the cancer patient. The method can include, e.g., measuring the concentration or absolute number of one or more subsets of immune cells in a biological sample obtained from the patient prior to administration of an anti-CD200 antibody. Exemplary cell types, subsets, and ranges of concentration and number of cell subsets indicative of immunocompetence are described herein. See section entitled "Methods for Treatment" (below). Methods for measuring the concentration or absolute number of one or more cell subsets in a biological sample from a patient are known in the art and exemplified herein in the working examples. In some embodiments, the method comprises: quantifying the concentration of $CD3^+$ cells present in a biological sample from a patient suffering from a cancer and administering to the patient the anti-CD200 antibody in an amount effective to treat the cancer in the patient if the concentration of $CD3^+$ cells in the biological sample is sufficient to aid the anti-CD200 therapy in the subject (e.g., if the concentration of $CD3^+$ cells is greater than 300 per microliter). In some embodiments, the antibody is administered to the patient if the concentration of $CD3^+/CD4^+$ cells in the biological sample is greater than or equal to 200 cells per microliter. In some embodiments, the antibody is administered to the patient if the concentration of $CD3^+/CD4^+$ cells in the biological sample is greater than or equal to 400 cells per microliter. In some embodiments, the antibody is administered to the patient if the concentration of $CD3^+/CD8^+$ cells in the biological sample is greater than or equal to 150 cells per microliter. In some embodiments, the antibody is administered to the patient if the concentration of $CD3^+/CD8^+$ cells in the biological sample is greater than or equal to 500 cells per microliter.

In some embodiments of any of the methods described herein, the anti-CD200 antibody is an IgG1, IgG2, IgG3, IgG4, IgM, IgA1, IgA2, IgA, IgD, or IgE antibody. In some embodiments, the anti-CD200 antibody is a murine antibody, a chimeric antibody, a humanized antibody, a single chain antibody, or a human antibody.

In some embodiments of any of the methods described herein, the anti-CD200 antibody comprises a variant constant region that has decreased (reduced) or no effector function. In some embodiments, the variant constant region has less than 90 (e.g., less than 85, 80, 75, 70, 65, 60, 55, 50, 45, 40, 35, 30, 25, 20, 15, or 10) % of the effector function activity of the corresponding non-variant form of the constant region. In some embodiments, a variant constant region has between about 0 to 30 (e.g., between about 5 to 30, 10 to 30, 10 to 20, 0 to 20, 0 to 15, 0 to 10, 0 to 25, or 0 to 5) % of the effector function activity of the corresponding non-variant form of the constant region. For example, an antibody described herein can contain an IgG1 variant constant region that exhibits, e.g., less than 20% (or in another example, between 0 to 20%) of the effector function activity of the corresponding non-variant IgG1 constant region. The variant anti-CD200 antibody constant region, as compared to the corresponding non-variant constant region, can have one or more of: reduced or no antibody-dependent cell-mediated cytotoxicity (ADCC) activity; reduced or no complement dependent cytotoxicity (CDC); and decreased binding to one or more Fc receptors. In some embodiments, the anti-CD200 antibody comprises a variant constant region that has been engineered to comprise at least one amino acid substitution, insertion, or deletion resulting in the reduced or no effector function. In some embodiments, the anti-CD200 antibody comprises a variant constant region comprising one or more of the following characteristics: (i) altered glycosylation and (ii) an Ala-Ala mutation. The altered glycosylation comprises one or more of the following: (i) a change in one or more sugar components; (ii) presence of one or more additional sugar components; and (iii) absence of one or more sugar components. In some embodiments, the anti-CD200 antibody can comprise, e.g., a hybrid IgG2/IgG4 constant region that has reduced or no effector function.

In some embodiments, the variant constant region having reduced or no effector function comprises a substitution at position 265 (relative to Kabat numbering, infra), e.g., an aspartate 265 to alanine substitution. See, e.g., Baudino et al. (2008) *J Immunol* 181:6664-6669. In some embodiments, the variant constant region having reduced or no effector function comprises one, two, or three of the following substitutions: L234F, L235E, or P331S, which have been shown to reduce substantially ADCC and CDC activity of variant constant regions in which they are present. See, e.g., Organesyan et al. (2008) *Acta Cryst D*64:700-704. Additional modifications to a constant region, to thereby result in a variant constant region with reduced or no effector function, are known in the art and recited herein.

In some embodiments of any of the methods described herein, the anti-CD200 antibody inhibits the interaction between CD200 and CD200R.

In some embodiments of any of the methods described herein, the anti-CD200 antibody contains the following paired set of CDRs: a heavy chain CDR1 (HCDR1) comprising the amino acid sequence: GFTFSGFAMS (SEQ ID NO:4); a heavy chain CDR2 (HCDR2) comprising the amino acid sequence: SISSGGTTYYLDSVKG (SEQ ID NO:5); a heavy chain CDR3 (HCDR3) comprising the amino acid sequence: GNYYSGTSYDY (SEQ ID NO:6); a light chain CDR1 (LCDR1) comprising the amino acid sequence: RAS-ESVDSYGNSFMH (SEQ ID NO:7); a light chain CDR2 (LCDR2) comprising the amino acid sequence: RASNLES (SEQ ID NO:8); and a light chain CDR3 (LCDR3) comprising the amino acid sequence: QQSNEDPRT (SEQ ID NO:9).

In some embodiments of any of the methods described herein, the anti-CD200 antibody contains the following paired set of CDRs: a HCDR1 comprising the amino acid sequence: GFNIKDYYMH (SEQ ID NO:10); a HCDR2 comprising the amino acid sequence: WIDPENGDTKYAP-KFQG (SEQ ID NO:11); a HCDR3 comprising the amino acid sequence: KNYYVSNYNFFDV (SEQ ID NO:12); a LCDR1 comprising the amino acid sequence: SASSS-VRYMY (SEQ ID NO:13); a LCDR2 comprising the amino acid sequence: DTSKLAS (SEQ ID NO:14); and a LCDR3 comprising the amino acid sequence: FQGSGYPLT (SEQ ID NO:15).

In some embodiments of any of the methods described herein, the anti-CD200 antibody contains the following paired set of CDRs: a HCDR1 comprising the amino acid sequence: GFNIKDYYIH (SEQ ID NO:16); a HCDR2 comprising the amino acid sequence: WIDPEIGATKYVPKFQG (SEQ ID NO:17); a HCDR3 comprising the amino acid sequence: LYGNYDRYYAMDY (SEQ ID NO:18); a LCDR1 comprising the amino acid sequence: KASQNVR-TAVA (SEQ ID NO:19); a LCDR2 comprising the amino acid sequence: LASNRHT (SEQ ID NO:20); and a LCDR3 comprising the amino acid sequence: LQHWNYPLT (SEQ ID NO:21).

In some embodiments of any of the methods described herein, the anti-CD200 antibody contains the following paired set of CDRs: a HCDR1 comprising the amino acid sequence: GYSFTDYIIL (SEQ ID NO:22); a HCDR2 comprising the amino acid sequence: HIDPYYGSSNYNLKFKG (SEQ ID NO:23); a HCDR3 comprising the amino acid sequence: SKRDYFDY (SEQ ID NO:24); a LCDR1 comprising the amino acid sequence: KASQDINSYLS (SEQ ID NO:25); a LCDR2 comprising the amino acid sequence: RANRLVD (SEQ ID NO:26); and a LCDR3 comprising the amino acid sequence: LQYDEFPYT (SEQ ID NO:27).

In some embodiments of any of the methods described herein, the anti-CD200 antibody contains the following paired set of CDRs: a HCDR1 comprising the amino acid sequence: GYTFTEYTMH (SEQ ID NO:28); a HCDR2 comprising the amino acid sequence: GVNPNNGGALYN-QKFKG (SEQ ID NO:29); a HCDR3 comprising the amino acid sequence: RSNYRYDDAMDY (SEQ ID NO:30); a LCDR1 comprising the amino acid sequence: KSSQSLL-DIDEKTYLN (SEQ ID NO:31); a LCDR2 comprising the amino acid sequence: LVSKLDS (SEQ ID NO:32); and a LCDR3 comprising the amino acid sequence: WQGTHF-PQT (SEQ ID NO:33).

In some embodiments of any of the methods described herein, the anti-CD200 antibody contains the following paired set of CDRs: a HCDR1 comprising the amino acid sequence: AFNIKDHYMH (SEQ ID NO:34); a HCDR2 comprising the amino acid sequence: WIDPESGDTEYAP-KFQG (SEQ ID NO:35); a HCDR3 comprising the amino acid sequence: FNGYQALDQ (SEQ ID NO:36); a LCDR1 comprising the amino acid sequence: TASSSVSSSYLH (SEQ ID NO:37); a LCDR2 comprising the amino acid sequence: STSNLAS (SEQ ID NO:38); and a LCDR3 comprising the amino acid sequence: RQYHRSPPIFT (SEQ ID NO:39).

The inventors have also discovered several biomarkers evidencing the occurrence in a human of a desired immunomodulatory effect by an anti-CD200 antibody administered to animals with an autoimmune disorder. For example, the inventors have observed that following administration of an anti-CD200 antibody to an animal, the concentration of several leukocyte (e.g., splenocyte) and bone marrow cell subsets is reduced in the animals. The inventors have also discovered that the concentration of, e.g., F4/80$^+$ lymphocytes in spleen are increased following administration of the anti-CD200 antibody to the animal. While the disclosure is not bound by any particular theory or mechanism of action, the inventors believe that monitoring a patient treated with an anti-CD200 antibody for a change (e.g., an increase or decrease) in one or more of these biomarkers is useful for, among other things, determining whether the anti-CD200 antibody is capable of producing a desired immunomodulatory effect in the human to which the antibody is administered. Moreover, one or more of the biomarkers are also useful for identifying a dose—a threshold dose (or a therapeutic dosing schedule)—of an anti-CD200 antibody, such as samalizumab, that by virtue of its immunomodulatory effect in the human is sufficient to achieve a clinically-meaningful effect on the disease (i.e., sufficient to treat a disease such as cancer or an autoimmune disorder). As described in the working examples, an anti-CD200 antibody was capable of reducing the concentration of autoimmune antibodies in a mouse model of autoimmune disease.

Accordingly, the disclosure features a method for determining whether an anti-CD200 antibody has produced a desired immunomodulatory effect in a human. The method includes measuring the concentration of one or more subsets of CD200$^+$ lymphocytes in a biological sample obtained from a human administered an anti-CD200 antibody, wherein a reduction in the concentration of one or more subsets of CD200$^+$ lymphocytes in a biological sample as compared to the concentration of the same subsets of CD200+ lymphocytes in a control sample indicates that the anti-CD200 antibody has produced a desired immunomodulatory effect in the human. The lymphocytes can be, e.g., splenocytes or bone marrow cell subsets.

In some embodiments of any of the methods described herein, the CD200$^+$ lymphocyte subsets can be, e.g., CD3$^+$/CD200$^+$ lymphocytes, CD45R$^+$/CD200$^+$ lymphocytes, CD5$^+$/CD200$^+$ lymphocytes, CD19$^+$/CD200$^+$ lymphocytes, CD138$^+$/CD200$^+$ lymphocytes, or CD200R$^+$/CD200$^+$ lymphocytes. In some embodiments of any of the methods described herein, at least a 5%, 10%, 20%, 30%, 40%, 50%, 60%, 70%, or 80% or more reduction of the concentration of the one or more subsets of CD200$^+$ lymphocytes indicates that a desired immunomodulatory effect has been produced in the human.

In some embodiments, a reduction in the concentration of one or more subsets of CD200$^+$ lymphocytes in the biological sample as compared to the concentration of the same subsets of CD200$^+$ lymphocytes in the control sample indicates that the antibody is therapeutically effective in the human.

In some embodiments of any of the methods described herein, the biological sample is a blood sample. In some embodiments, the biological sample comprises, or consists of, spleen tissue or bone marrow tissue.

In another aspect, the disclosure features a method for determining whether an anti-CD200 antibody has produced a desired immunomodulatory effect in a human, which method includes measuring the concentration of one or more subsets of CD200$^+$ bone marrow cells in a biological sample obtained from a human administered an anti-CD200 antibody, wherein a reduction in the concentration of one or more subsets of CD200$^+$ bone marrow cells in a biological sample as compared to the concentration of the same subsets of CD200$^+$ bone marrow cells in a control sample indicates that the anti-CD200 antibody has produced a desired immunomodulatory effect in the human. The subsets of CD200$^+$ bone marrow cells can be, e.g., Igk$^+$/CD200$^+$ bone marrow cells, CD138$^+$/CD200$^+$ bone marrow cells, c-kit$^+$/CD200$^+$ bone marrow cells, or c-kit$^+$/CD200$^+$/Lin$^{-/low}$ bone marrow cells.

In some embodiments of any of the methods described herein, at least a 5%, 10%, 20%, 30%, 40%, 50%, 60%, 70%, or 80% or more reduction of the concentration of the one or more subsets of CD200$^+$ bone marrow cells indicates that a desired immunomodulatory effect has been produced in the human.

In some embodiments of any of the methods described herein, a reduction in the concentration of one or more subsets of CD200$^+$ bone marrow cells in the biological sample as compared to the concentration of the same subsets of CD200$^+$ bone marrow cells in the control sample indicates that the antibody is therapeutically effective in the human.

In some embodiments of any of the above methods, the control sample is a biological sample of the same type obtained from the human prior to administering the anti-CD200 antibody.

In yet another aspect, the disclosure features a method for determining whether an anti-CD200 antibody has produced a desired immunomodulatory effect in a human, which method includes quantifying the level of CD200 expression by a plurality of leukocytes in a biological sample obtained from a human administered an anti-CD200 antibody, wherein a reduction in CD200 expression by the plurality as compared to a control expression level indicates that the anti-CD200 antibody has produced a desired immunomodulatory effect in the human. The leukocytes can be, e.g., one or more bone marrow cell subsets or splenocytes.

In some embodiments of any of the methods described herein, the CD200$^+$ leukocytes can be, e.g., CD3$^+$/CD200$^+$ leukocytes, CD45R$^+$/CD200$^+$ leukocytes, CD5$^+$/CD200$^+$ leukocytes, CD19$^+$/CD200$^+$ leukocytes, CD138$^+$/CD200$^+$ leukocytes, or CD200R$^+$/CD200+ leukocytes.

In some embodiments of any of the methods described herein, at least a 5%, 10%, 20%, 30%, 40%, 50%, 60%, 70%, or 80% or more reduction of the level of CD200 expression by the plurality indicates that a desired immunomodulatory effect has been produced in the human.

In some embodiments of any of the methods described herein, a reduction in the level of CD200 expression by the plurality as compared to the control expression level indicates that the antibody is therapeutically effective in the human.

In another aspect, the disclosure features a method for determining whether an anti-CD200 antibody has produced a desired immunomodulatory effect in a human. The method includes quantifying the level of CD200 expression by a plurality of bone marrow cells in a biological sample obtained from a human administered an anti-CD200 antibody, wherein a reduction in CD200 expression by the plurality as compared to a control expression level indicates that the anti-CD200 antibody has produced a desired immunomodulatory effect in the human.

In some embodiments of any of the methods described herein, the CD200$^+$ bone marrow cells are, e.g., Igk$^+$/CD200$^+$ bone marrow cells, CD138$^+$/CD200$^+$ bone marrow cells, c-kit$^+$/CD200$^+$ bone marrow cells, or c-kit$^+$/CD200$^+$/Lin$^{-/low}$ bone marrow cells.

In some embodiments of any of the methods described herein, at least a 5%, 10%, 20%, 30%, 40%, 50%, 60%, 70%, or 80% or more reduction of the level of CD200 expression by the plurality indicates that a desired immunomodulatory effect has been produced in the human.

In some embodiments of any of the methods described herein, a reduction in the level of CD200 expression by the plurality as compared to the control expression level indicates that the antibody is therapeutically effective in the human.

In some embodiments of any of the methods described herein, the control sample is a biological sample of the same type obtained from the human prior to administering the anti-CD200 antibody.

In yet another aspect, the disclosure features a method for determining whether an anti-CD200 antibody has produced a desired immunomodulatory effect in a human, the method comprising: (i) measuring the concentration of $CD200^+$ leukocytes in a biological sample obtained from a human prior to administration to the human of an anti-CD200 antibody to thereby obtain a pre-treatment $CD200^+$ leukocyte concentration; (ii) administering to the human the antibody; and (iii) measuring the concentration of CD200+ leukocytes in a biological sample obtained from the human following administration of the antibody to thereby obtain a post-treatment CD200+ leukocyte concentration, wherein a reduction in the post-treatment $CD200^+$ leukocyte concentration as compared to the pre-treatment $CD200^+$ leukocyte concentration indicates that the antibody has produced a desired immunomodulatory effect in the human.

In another aspect, the disclosure features a method for determining whether an anti-CD200 antibody has produced a desired immunomodulatory effect in a human, the method comprising: (i) measuring the concentration of $CD200^+$ bone marrow cells in a biological sample obtained from a human prior to administration to the human of an anti-CD200 antibody to thereby obtain a pre-treatment $CD200^+$ bone marrow cell concentration; (ii) administering to the human the antibody; and (iii) measuring the concentration of CD200+ bone marrow cells in a biological sample obtained from the human following administration of the antibody to thereby obtain a post-treatment $CD200^+$ bone marrow cell concentration, wherein a reduction in the post-treatment $CD200^+$ bone marrow cell concentration as compared to the pre-treatment CD200+ bone marrow cell concentration indicates that the antibody has produced a desired immunomodulatory effect in the human.

In another aspect, the disclosure features a method for determining whether an anti-CD200 antibody has produced a desired immunomodulatory effect in a human, the method comprising: (i) quantifying the level of CD200 expression by a plurality of leukocytes in a biological sample obtained from a human prior to administration to the human of an anti-CD200 antibody to thereby obtain a pre-treatment CD200 expression level; (ii) administering to the human the antibody; and (iii) quantifying the level of CD200 expression by a plurality of leukocytes in a biological sample obtained from the human following administration of the antibody to thereby obtain a post-treatment CD200 expression level, wherein a reduction in the post-treatment CD200 expression level as compared to the pre-treatment CD200 expression level indicates that the antibody has produced a desired immunomodulatory effect in the human.

In another aspect, the disclosure features a method for determining whether an anti-CD200 antibody has produced a desired immunomodulatory effect in a human, the method comprising: (i) quantifying the level of CD200 expression by a plurality of bone marrow cells in a biological sample obtained from a human prior to administration to the human of an anti-CD200 antibody to thereby obtain a pre-treatment CD200 expression level; (ii) administering to the human the antibody; and (iii) quantifying the level of CD200 expression by a plurality of bone marrow cells in a biological sample obtained from the human following administration of the antibody to thereby obtain a post-treatment CD200 expression level, wherein a reduction in the post-treatment CD200 expression level as compared to the pre-treatment CD200 expression level indicates that the antibody has produced a desired immunomodulatory effect in the human.

In yet another aspect, the disclosure features a computer readable medium comprising a medical profile of a human, the profile comprising information on at least one of (a): (i) the concentration of $CD200^+$ leukocytes in a biological sample obtained from a human following administration to the human of an anti-CD200 antibody and (ii) the concentration of CD200+ leukocytes of the same histological type as in (i) in a biological sample obtained from the human prior to administration of the antibody; (b): (iii) the concentration of $CD200^+$ bone marrow cells in a biological sample obtained from a human following administration to the human of an anti-CD200 antibody and (iv) the concentration of $CD200^+$ bone marrow cells of the same histological type as in (iii) in a biological sample obtained from the human prior to administration of the antibody; (c): (v) the level of expression of CD200 by a plurality of leukocytes in a biological sample obtained from the human following administration to the human of an anti-CD200 antibody and (vi) the level of expression of CD200 by a plurality of leukocytes of the same histological type as in (v) in a biological sample obtained from the human prior to administration of the antibody; and (d): (vii) the level of expression of CD200 by a plurality of bone marrow cells in a biological sample obtained from the human following administration to the human of an anti-CD200 antibody and (viii) the level of expression of CD200 by a plurality of bone marrow cells of the same histological type as in (vii) in a biological sample obtained from the human prior to administration of the antibody.

In another aspect, the disclosure features a computer-based method for determining whether an anti-CD200 antibody has produced a desired immunomodulatory effect in a human, the method comprising: (A) receiving data including a medical profile of a human, the profile comprising information on at least one of: (a): (i) the concentration of $CD200^+$ leukocytes in a biological sample obtained from a human following administration to the human of an anti-CD200 antibody and (ii) the concentration of CD200+ leukocytes of the same histological type as in (i) in a biological sample obtained from the human prior to administration of the antibody; (b): (iii) the concentration of $CD200^+$ bone marrow cells in a biological sample obtained from a human following administration to the human of an anti-CD200 antibody and (iv) the concentration of $CD200^+$ bone marrow cells of the same histological type as in (iii) in a biological sample obtained from the human prior to administration of the antibody; (c): (v) the level of expression of CD200 by a plurality of leukocytes in a biological sample obtained from the human following administration to the human of an anti-CD200 antibody and (vi) the level of expression of CD200 by a plurality of leukocytes of the same histological type as in (v) in a biological sample obtained from the human prior to administration of the antibody; and (d): (vii) the level of expression of CD200 by a plurality of bone marrow cells in a biological sample obtained from the human following administration to the human of an anti-CD200 antibody and (viii) the level of expression of CD200 by a plurality of bone marrow cells of the same histological type as in (vii) in a biological sample obtained from the human prior to administration of the antibody; and (B) processing at least the portion of the data containing the information to determine whether the antibody has produced a desired immunomodulatory effect in the human. (1) A reduction in the post-treatment $CD200^+$ leukocyte concentration as compared to the pre-treatment $CD200^+$ leukocyte concentration indicates that the antibody has produced a desired immunomodulatory effect in the human; (2) a reduction in the post-treatment CD200$^+$ bone marrow cell concentration as compared to the pre-treatment CD200$^+$ bone marrow cell concentration indicates that the antibody has produced a desired immunomodulatory effect in the human; (3) a reduction in post-treatment CD200 expression level by leukocytes as compared to the pre-treatment CD200 expression level by leukocytes indicates that the antibody has produced a desired immunomodulatory effect in the human; or (4) a reduction in post-treatment CD200 expression level by bone marrow cells as compared to the pre-treatment CD200 expression level by bone marrow cells indicates that the antibody has produced a desired immunomodulatory effect in the human.

In another aspect, the disclosure features a computer-based method for determining whether an anti-CD200 antibody has produced a desired immunomodulatory effect in a human, the method comprising: (1) providing information for at least one of: (a): (i) the concentration of CD200$^+$ leukocytes in a biological sample obtained from a human following administration to the human of an anti-CD200 antibody and (ii) the concentration of CD200$^+$ leukocytes of the same histological type as in (i) in a biological sample obtained from the human prior to administration of the antibody; (b): (iii) the concentration of CD200$^+$ bone marrow cells in a biological sample obtained from a human following administration to the human of an anti-CD200 antibody and (iv) the concentration of CD200$^+$ bone marrow cells of the same histological type as in (iii) in a biological sample obtained from the human prior to administration of the antibody; (c): (v) the level of expression of CD200 by a plurality of leukocytes in a biological sample obtained from the human following administration to the human of an anti-CD200 antibody and (vi) the level of expression of CD200 by a plurality of leukocytes of the same histological type as in (v) in a biological sample obtained from the human prior to administration of the antibody; and (d): (vii) the level of expression of CD200 by a plurality of bone marrow cells in a biological sample obtained from the human following administration to the human of an anti-CD200 antibody and (viii) the level of expression of CD200 by a plurality of bone marrow cells of the same histological type as in (vii) in a biological sample obtained from the human prior to administration of the antibody; (II) inputting the information into a computer; and (III) calculating a parameter indicating whether the antibody has produced a desired immunomodulatory effect in the human using the computer and the input information. (1) A reduction in the post-treatment CD200$^+$ leukocyte concentration as compared to the pre-treatment CD200+ leukocyte concentration indicates that the antibody has produced a desired immunomodulatory effect in the human; (2) a reduction in the post-treatment CD200$^+$ bone marrow cell concentration as compared to the pre-treatment CD200$^+$ bone marrow cell concentration indicates that the antibody has produced a desired immunomodulatory effect in the human; (3) a reduction in post-treatment CD200 expression level by leukocytes as compared to the pre-treatment CD200 expression level by leukocytes indicates that the antibody has produced a desired immunomodulatory effect in the human; or (4) a reduction in post-treatment CD200 expression level by bone marrow cells as compared to the pre-treatment CD200 expression level by bone marrow cells indicates that the antibody has produced a desired immunomodulatory effect in the human. The method can include outputting the parameter.

In some embodiments of any of the methods described herein, the human has, is suspected of having, or is likely to develop, a cancer. The cancer can be, e.g., chronic lymphocytic leukemia (e.g., B cell chronic lymphocytic leukemia). The cancer can be a solid tumor, e.g., a colon cancer, a breast cancer, a lung cancer, a renal cancer, a pancreatic cancer, a thyroid cancer, a skin cancer, a cancer of the nervous system, a cervical cancer, an ovarian cancer, a testicular cancer, a head and neck cancer, a cancer of the eye, a stomach cancer, or a liver cancer. The cancer of the nervous system can be, e.g., a neuroblastoma.

In some embodiments of any of the methods described herein, the human has, is suspected of having, or is at risk for developing, an inflammatory disorder or a bone disorder. The inflammatory disorder can be, e.g., an autoimmune disorder such as, e.g., a hemolytic disorder. The autoimmune disorder can be an autoimmune hemolytic anemia. The autoimmune disorder can be, e.g., chronic obstructive pulmonary disease, diabetes mellitus type 1, Goodpasture's syndrome, Grave's disease, Guillain-Barré syndrome, IgA nephropathy, scleroderma, Sjögren's syndrome, systemic lupus erthyematosus, lupus nephritis, glomerulonephritis, Wegener's granulomatosis, pemphigus vulgaris, rheumatoid arthritis, Chagas disease, cold agglutinin disease, anti-phospholipid syndrome, warm autoimmune hemolytic anemia, paroxysmal cold hemoglobinuria, Hashimoto's disease, idiopathic thrombocytopenic purpura, myasthenia gravis, pulmonary biliary cirrhosis, or Miller Fisher syndrome.

In some embodiments of any of the methods described herein, the one or more subsets of CD200$^+$ leukocytes are selected from the group consisting of CD3$^+$/CD200$^+$ lymphocytes, CD45R$^+$/CD200$^+$ lymphocytes, CD5$^+$/CD200R$^+$ lymphocytes, CD19$^+$/CD200$^+$ lymphocytes, CD138$^+$/CD200$^+$ lymphocytes, and CD200R$^+$/CD200$^+$ lymphocytes.

In some embodiments of any of the methods described herein, the one or more subsets of CD200$^+$ bone marrow cells are selected from the group consisting of Igk$^+$/CD200$^+$ bone marrow cells, CD138$^+$/CD200$^+$ bone marrow cells, c-kit$^+$/CD200$^+$ bone marrow cells, and c-kit$^+$/CD200$^+$/Lin$^-$ bone marrow cells.

In some embodiments, the methods include administering to the human a therapeutically-effective amount of the anti-CD200 antibody if the antibody has been determined to produce a desired immunomodulatory effect in the human.

In yet another aspect, the disclosure features a method for determining an anti-CD200 antibody dosing schedule for a patient, the method comprising: administering to a patient an anti-CD200 antibody to thereby reduce the concentration of one or more subsets of CD200$^+$ leukocytes in a biological sample obtained from the patient as compared to the concentration of the same subsets of CD200$^+$ leukocytes in a control sample, wherein the patient is afflicted with a disorder selected from the group consisting of a cancer, an inflammatory disorder, or a bone disorder; and monitoring the concentration of the one or more subsets of CD200$^+$ leukocytes in the patient to thereby determine for the patient a dosing schedule of the antibody, wherein the dosing schedule is sufficient to maintain a reduced concentration of the one or more subsets of CD200$^+$ leukocytes in the patient for the duration of the treatment of the disorder with the antibody. In some embodiments, the concentration of the one or more subsets of CD200+ leukocytes is reduced by at least 10%, 20%, 30%, 40%, 50%, 60%, 70%, 80%, or 90% or more.

In some embodiments of any of the methods described herein, the one or more subsets of CD200$^+$ leukocytes are selected from the group consisting of CD3$^+$/CD200+ lymphocytes, CD45R$^+$/CD200$^+$ lymphocytes, CD5$^+$/CD200$^+$ lymphocytes, CD19$^+$/CD200$^+$ lymphocytes, CD138$^+$/CD200$^+$ lymphocytes, CD200R$^+$/CD200$^+$ lymphocytes, CD200$^+$/CD4$^+$ T cells, activated CD200$^+$/CD4$^+$ T cells, and CD200⁺/CD8⁺ T cells. In some embodiments, the biological sample comprises spleen tissue from the patient.

In yet another aspect, the disclosure features a method for determining an anti-CD200 antibody dosing schedule for a patient. The method includes administering to a patient an anti-CD200 antibody to thereby reduce the level of expression of CD200 by one or more subsets of leukocytes in a biological sample obtained from the patient as compared to a control expression level of CD200 by leukocytes of the same histological type in a control sample, wherein the patient is afflicted with a disorder selected from the group consisting of a cancer, an inflammatory disorder, or a bone disorder; and monitoring the expression level of CD200 by the one or more subsets of leukocytes in the patient to thereby determine for the patient a dosing schedule of the antibody, wherein the dosing schedule is sufficient to maintain a reduced level of expression of CD200 by the one or more subsets of leukocytes in the patient for the duration of the treatment of cancer with the antibody.

In some embodiments of any of the methods described herein, the expression level of CD200 by the one or more subsets of leukocytes is reduced by at least 10%, 20%, 30%, 40%, 50%, 60%, 70%, or 80% or more.

In another aspect, the disclosure features a method for determining an anti-CD200 antibody dosing schedule for a patient. The method includes administering to a patient an anti-CD200 antibody to thereby reduce the concentration of one or more subsets of CD200⁺ bone marrow cells in a biological sample obtained from the patient as compared to the concentration of the same subsets of CD200⁺ bone marrow cells in a control sample, wherein the patient is afflicted with a disorder selected from the group consisting of a cancer, an inflammatory disorder, or a bone disorder; and monitoring the concentration of the one or more subsets of CD200⁺ bone marrow cells in the patient to thereby determine for the patient a dosing schedule of the antibody, wherein the dosing schedule is sufficient to maintain a reduced concentration of the one or more subsets of CD200⁺ bone marrow cells in the patient for the duration of the treatment of the disorder with the antibody.

In some embodiments, the concentration of the one or more subsets of CD200⁺ bone marrow cells is reduced by at least 10%, 20%, 30%, 40%, 50%, 60%, 70%, 80%, or 90% or more.

In some embodiments, the one or more subsets of CD200⁺ bone marrow cells are selected from the group consisting of Igk⁺/CD200⁺ bone marrow cells, CD138⁺/CD200⁺ bone marrow cells, c-kit⁺/CD200⁺ bone marrow cells, and c-kit⁺/CD200⁺/Lin⁻$^{/low}$ bone marrow cells.

In yet another aspect, the disclosure features a method for determining an anti-CD200 antibody dosing schedule for a patient, the method comprising: administering to a patient an anti-CD200 antibody to thereby reduce the level of expression of CD200 by one or more subsets of bone marrow cells in a biological sample obtained from the patient as compared to a control expression level of CD200 by bone marrow cells of the same histological type in a control sample, wherein the patient is afflicted with a disorder selected from the group consisting of a cancer, an inflammatory disorder, or a bone disorder; and monitoring the expression level of CD200 by the one or more subsets of bone marrow cells in the patient to thereby determine for the patient a dosing schedule of the antibody, wherein the dosing schedule is sufficient to maintain a reduced level of expression of CD200 by the one or more subsets of bone marrow cells in the patient for the duration of the treatment of cancer with the antibody.

In yet another aspect, the disclosure features a method for treating a human suffering from a disorder, the method comprising administering to a human in need thereof an anti-CD200 antibody in an amount and with a frequency sufficient to reduce the concentration of CD200⁺ leukocytes or CD200+ bone marrow cells in a cancer patient to thereby treat the human, wherein the human is afflicted with a disorder selected from the group consisting of a cancer, an inflammatory disorder, and a bone disorder. The method can include monitoring the human for a reduction in the CD200⁺ leukocytes or CD200⁺ bone marrow cells in the patient. In some embodiments, the concentration of CD200⁺ leukocytes in the blood of the patient is reduced. In some embodiments, the concentration of CD200⁺ leukocytes in the spleen of the patient is reduced. The method can include monitoring the human for a reduction in the expression level of CD200 by leukocytes or bone marrow cells in the patient.

In some embodiments of any of the methods described herein, the anti-CD200 antibody is an IgG1, IgG2, IgG3, IgG4, IgM, IgA1, IgA2, IgA, IgD, or IgE antibody. The antibody can be, e.g., a murine antibody, a chimeric antibody, a humanized antibody, a single chain antibody, or a human antibody. In some embodiments, the anti-CD200 antibody is a variant antibody that has decreased or no effector function as described herein.

In any of the methods, the anti-CD200 antibody can be any one of the anti-CD200 antibodies described herein such as, but in no way limited to, samalizumab.

"Polypeptide," "peptide," and "protein" are used interchangeably and mean any peptide-linked chain of amino acids, regardless of length or post-translational modification. The CD200 proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The CD200 proteins described herein also include "antigenic peptide fragments" of the proteins, which are shorter than full-length CD200 proteins, but retain at least 10% (e.g., at least 10%, at least 15%, at least 20%, at least 25%, at least 30%, at least 35%, at least 40%, at least 45%, at least 50%, at least 55%, at least 60%, at least 70%, at least 80%, at least 90%, at least 95%, at least 98%, at least 99%, at least 99.5%, or 100% or more) of the ability of the full-length protein to induce an antigenic response in a mammal (see below under "Methods for Producing an Antibody"). Antigenic peptide fragments of a CD200 protein include terminal as well internal deletion variants of the protein. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Antigenic peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200 or more) amino acid residues in length (e.g., at least 6 contiguous amino acid residues in any one of SEQ ID NOs:1 to 3). In some embodiments, an antigenic peptide fragment of a human CD200 protein is less than 225 (e.g., less than 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, or 7) amino acid residues in length (e.g., less than 225 contiguous amino acid residues in any one of SEQ ID NOs:1 to 3). In some embodiments, an antigenic peptide fragment of a full-length CD200 protein is at least 6, but less than 225, amino acid residues in length.

In some embodiments, the human CD200 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to the human CD200 protein having the amino acid sequence depicted in SEQ ID NO:1 or SEQ ID NO:2 (see below). In some embodiments, the human CD200 protein has the amino acid sequence depicted in SEQ ID NO:1 or SEQ ID NO:2.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNAS-TAR) software. Appropriate parameters for measuring alignment, including any algorithms needed to achieve maximal alignment over the full-length of the sequences being compared can be determined by known methods.

Amino acid sequences for exemplary human CD200 proteins as well as antigenic peptide fragments thereof are known in the art and are set forth below.

As used herein, the term "antibody" refers to a whole or intact antibody molecule (e.g., IgM, IgG (including IgG1, IgG2, IgG3, and IgG4), IgA, IgD, or IgE) or any antigen-binding fragment thereof. The term antibody includes, e.g., a chimerized or chimeric antibody, a humanized antibody, a deimmunized antibody, and a fully human antibody. Antigen-binding fragments of an antibody include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies (see, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety) are also included in the definition of antibody and are compatible for use in the methods described herein. Bispecific antibodies (including DVD-Ig antibodies; see below) are also embraced by the term "antibody." Bispecific antibodies are monoclonal, preferably human or humanized, antibodies that have binding specificities for at least two different antigens.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for determining whether an anti-CD200 antibody has produced in immunomodulatory effect in a human, will be apparent from the following description, the examples, and from the claims.

DETAILED DESCRIPTION

The present disclosure relates to anti-CD200 antibodies (e.g., variant anti-CD200 antibodies having decreased or no effector function) and to biomarkers for use in determining whether a human has been administered a dose of one or more of the antibodies that produces a desired immunomodulatory effect in the human. Also featured are diagnostic and therapeutic methods that utilize the antibodies and biomarkers.

While in no way intended to be limiting, exemplary anti-CD200 antibodies and CD200-binding fragments thereof, conjugates, pharmaceutical compositions and formulations, biomarkers, and methods employing any of the foregoing are elaborated on below and are exemplified in the working Examples.

Compositions

Figure 3:
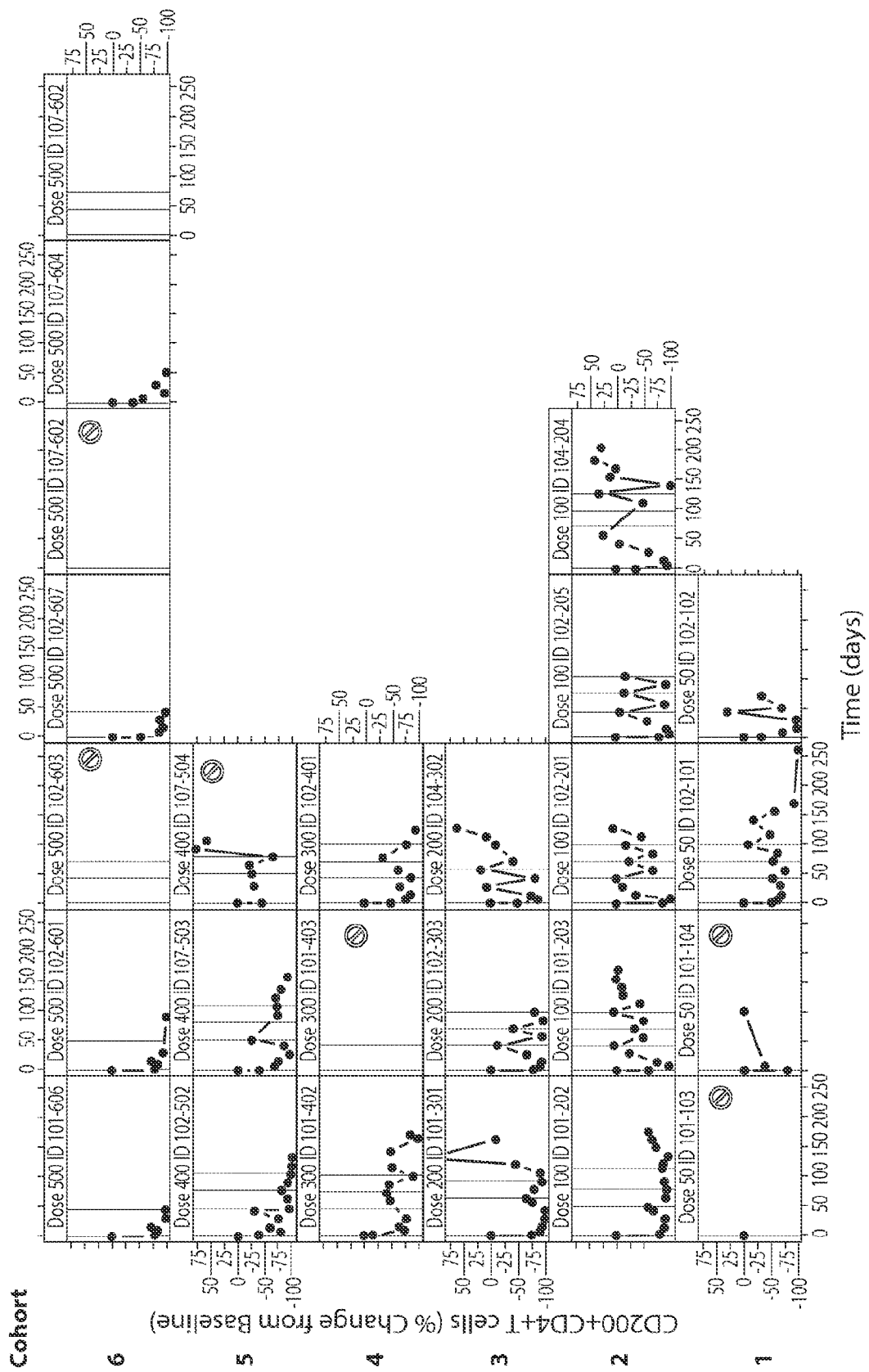
FIG. 3 are a series of line graphs depicting the nature of the reduction in CD200$^+$/CD4$^+$ T cells in different patients, respectively, following the administration of samalizumab to the patients. For each row of line graphs, the Y-axis represents the percent change in the CD200$^+$/CD4+ T cell population, from baseline, as measured in a biological sample from the patient. The numeric units identified on the Y-axis are, in descending order from the top of each graph: 75, 50, 25, 0, −25, −50, −75, and −100. The X-axis for each individual line graph represents the time in days following initial administration of samalizumab. The vertical bars represent the days on which samalizumab was administered. Each row of line graphs corresponds to a particular cohort numbered 1 to 6. As elaborated on below in the working Examples, patients in cohort 6 received 500 mg/m² of samalizumab each dose. Patients in cohort 5 received 400 mg/m² of samalizumab each dose. Each dose of samalizumab administered to patients in cohort 4 was 300 mg/m². Each dose of samalizumab administered to patients in cohort 3 was 200 mg/m². Patients in cohort 2 received 100 mg/m² of samalizumab and patients in cohort 1 received 50 mg/m² of samalizumab for each dose. Each individual line graph corresponds to one patient within each cohort. Unevaluable patients are designated by a once-crossed circle. Only four doses (cycles) are shown in the figure. Data from the single patient from cohort 7 not included.

The disclosure features antibodies that bind to a human CD200 polypeptide (sometimes the antibodies are referred to herein as "anti-CD200 antibodies"). Also featured are antigen-binding (CD200-binding) fragments of the antibodies. In some embodiments, an anti-CD200 antibody described herein binds to an epitope in the human CD200 protein. For example, the anti-CD200 antibody can bind to an epitope in the human CD200 protein comprising, or consisting of, the following amino acid sequence:
MERLVIRMPFSHLSTYSLVWVMAAVV-LCTAQVQVVTQDEREQLYTPASLKC SLQNAQEALIVTWQKKKAVSPENMVTF-SENHGVVIQPAYKDKINITQLGLQN STITFWNITLE-DEGCYMCLFNTFGFGKISGTA-CLTVYVQPIVSLHYKFSEDHLN ITCSATARPAPMVFWKVPRSGIEN-STVTLSHPNGTTSVTSILHIKDPKNQVGKE VICQV-LHLGTVTDFKQTVNKGYWFSV-PLLLSIVSLVILLVLISILLYWKRHRNQ DREP (SEQ ID NO:1; Genbank Accession No. NP_005935.2). SEQ ID NO:1 depicts the amino acid sequence for a full-length, precursor human CD200 isoform A protein. In some embodiments, an anti-CD200 antibody described herein binds to an epitope in the human CD200 protein comprising, or consisting of, the following amino acid sequence:
MERLTLTRTIGGPLLTATLLGKTTIN-DYQVIRMPFSHLSTYSLVWVMAAVVLC TAQVQV-VTQDEREQLYTPASLKCS-LQNAQEALIVTWQKKKAVSPENMVTFS ENHGVVIQPAYKDKINITQLGLQNSTIT-FWNITLEDEGCYMCLFNTFGFGKISG TACLTVYVQPIVSLHYKFSEDHLNITC-SATARPAPMVFWKVPRSGIENSTVTL SHPNGTTS-VTSILHIKDPKNQVGKEVICQV-LHLGTVTDFKQTVNKGYWFSVPL LLSIVSLVILLVLISILLYWKRHRNQDREP (SEQ ID NO:2; Genbank Accession No. NP_001004196.2). SEQ ID NO:2 depicts the amino acid sequence of a full-length CD200 isoform B protein. In some embodiments, the anti-CD200 antibody binds to an epitope present in a human CD200 protein having the following amino acid sequence:
VIRMPFSHLSTYSLVWVMAAVV-LCTAQVQVVTQDEREQLYTTASLKCSLQN AQEALIVTWQKKKAVSPENMVTFSENH-GVVIQPAYKDKINITQLGLQNSTITF WNITLEDEG-CYMCLFNTFGFGKISGTACLTVYVQPIV-SLHYKFSEDHLNITCS ATARPAPMVFWKVPRSGIENSTVTLSHP-NGTTSVTSILHIKDPKNQVGKEVIC QVLHLGTVTD-FKQTVNKGYWFSVPLLLSIVSLVILLV-LISILLYWKRHRNQDR GELSQGVQKMT
(SEQ ID NO:3; Genbank Accession No. CAA28943.1; FIG. 3 of McCaughan et al. (1987) *Immunogenetics* 25:329-335). SEQ ID NO:3 is an exemplary sequence for a full-length human CD200 protein.

In some embodiments, an anti-CD200 antibody described herein binds to an epitope within the extracellular portion of a CD200 protein. For example, in some embodiments, the anti-CD200 antibody can bind to CD200 protein at an epitope within or overlapping with: (i) amino acids 1 to 233 of the amino acid sequence depicted in SEQ ID NO:1; (ii) amino acids 1 to 258 of the amino acid sequence depicted in SEQ ID NO:2; or amino acids 1 to 229 of the amino acid sequence depicted in SEQ ID NO:3.

In some embodiments, the anti-CD200 antibody binds to an epitope in the human CD200 protein lacking the leader sequence. For example, an anti-CD200 antibody described herein can bind to a CD200 protein at an epitope within or overlapping with amino acids 31 to 233 of the amino acid sequence depicted in SEQ ID NO:1, which corresponds to the extracellular portion of the mature form of human CD200 isoform A less the amino terminal leader sequence. In some embodiments, an anti-CD200 antibody described herein can bind to a CD200 protein at an epitope within or overlapping with amino acids 56 to 258 of the amino acid sequence depicted in SEQ ID NO:2, which corresponds to the extracellular portion of the mature form of human CD200 isoform B less the amino terminal leader sequence. In some embodiments, an anti-CD200 antibody described herein can bind to a CD200 protein at an epitope within or overlapping with amino acids 27 to 229 of the amino acid sequence depicted in SEQ ID NO:3, which corresponds to the extracellular portion of the mature form of human CD200 less the amino terminal leader sequence.

An "epitope" refers to the site on a protein (e.g., a human CD200 protein) that is bound by an antibody. "Overlapping epitopes" include at least one (e.g., two, three, four, five, or six) common amino acid residue(s).

In some embodiments, the anti-CD200 antibody specifically binds to a human CD200 protein (e.g., the human CD200 protein having the amino acid sequence depicted in SEQ ID NO:1, SEQ ID NO:2, SEQ ID NO:3, or the extracellular domains of the mature forms of the CD200 proteins). The terms "specific binding" or "specifically binds" refer to two molecules forming a complex (e.g., a complex between an anti-CD200 antibody and a CD200 protein) that is relatively stable under physiologic conditions. Typically, binding is considered specific when the association constant ($K_a$) is higher than $10^6$ M$^{-1}$. Thus, an anti-CD200 antibody can specifically bind to a CD200 protein with a $K_a$ of at least (or greater than) $10^6$ (e.g., at least or greater than $10^7$, $10^8$, $10^9$, $10^{10}$, $10^{11}$ $10^{12}$, $10^{13}$, $10^{14}$, or $10^{15}$ or higher) M$^{-1}$. Examples of antibodies that specifically bind to a human CD200 protein are described in, e.g., U.S. Pat. Nos. 7,408,041; 7,427,665; 7,435,412; and 7,598,353, the disclosures of each of which are incorporated herein by reference in their entirety.

The amino acid sequence for several exemplary anti-CD200 antibodies are described in, e.g., U.S. Pat. No. 7,408,041. For example, the anti-CD200 antibody can comprise the amino acid sequence of the heavy and light chain variable regions of one of the Fab antibodies—d1B10, d1A5, d1B5, c2aB7, c1A10, or c2aA10—depicted in FIG. 23 of U.S. Pat. No. 7,408,041, the sequences depicted in FIG. 23 being incorporated herein by reference in their entirety. In some embodiments, an anti-CD200 antibody described herein contains a paired set of heavy chain CDRs and light chain CDRs of one of the Fab antibodies depicted in FIG. 23 of U.S. Pat. No. 7,408,041. For example, an anti-CD200 antibody described herein contains the paired set of CDRs from the d1B10 Fab antibody: a heavy chain CDR1 (HCDR1) comprising the following sequence: GFTFSGFAMS (SEQ ID NO:4); a heavy chain CDR2 (HCDR2) comprising the following sequence: SISSGGTTYYLDSVKG (SEQ ID NO:5); a heavy chain CDR3 (HCDR3) comprising the following sequence: GNYYSGTSYDY (SEQ ID NO:6); a light chain CDR1 (LCDR1) comprising the following sequence: RASESVDSYGNSFMH (SEQ ID NO:7); a light chain CDR2 (LCDR2) comprising the following sequence: RASNLES (SEQ ID NO:8); and a light chain CDR3 (LCDR3) comprising the following sequence: QQSNEDPRT (SEQ ID NO:9).

In another example, an anti-CD200 antibody described herein can contain the paired set of CDRs from the d1A5 Fab antibody: (i) a HCDR1 comprising the following sequence: GFNIKDYYMH (SEQ ID NO:10); a HCDR2 comprising the following sequence: WIDPENGDTKYAPKFQG (SEQ ID NO:11); a HCDR3 comprising the following sequence: KNYYVSNYNFFDV (SEQ ID NO:12); a LCDR1 comprising the following sequence: SASSSVRYMY (SEQ ID NO:13); a LCDR2 comprising the following sequence: DTSKLAS (SEQ ID NO:14); and a LCDR3 comprising the following sequence: FQGSGYPLT (SEQ ID NO:15).

In another example, an anti-CD200 antibody described herein can comprise the paired set of CDRs from the d1B5 Fab antibody: a HCDR1 comprising the following amino acid sequence: GFNIKDYYIH (SEQ ID NO:16); a HCDR2 comprising the following amino acid sequence: WIDPEIGATKYVPKFQG (SEQ ID NO:17); a HCDR3 comprising the following amino acid sequence: LYGNYDRYYAMDY (SEQ ID NO:18); a LCDR1 comprising the following amino acid sequence: KASQNVRTAVA (SEQ ID NO:19); a LCDR2 comprising the following amino acid sequence: LASNRHT (SEQ ID NO:20); and a LCDR3 comprising the following amino acid sequence: LQHWNYPLT (SEQ ID NO:21).

In another example, an anti-CD200 antibody described herein can contain the paired set of CDRs from the c2aB7 Fab antibody: a HCDR1 comprising the amino acid sequence: GYSFTDYIIL (SEQ ID NO:22); a HCDR2 comprising the amino acid sequence: HIDPYYGSSNYNLKFKG (SEQ ID NO:23); a HCDR3 comprising the amino acid sequence: SKRDYFDY (SEQ ID NO:24); a LCDR1 comprising the amino acid sequence: KASQDINSYLS (SEQ ID NO:25); a LCDR2 comprising the amino acid sequence: RANRLVD (SEQ ID NO:26); and a LCDR3 comprising the amino acid sequence: LQYDEFPYT (SEQ ID NO:27).

In yet another example, an anti-CD200 antibody described herein can contain a paired set of CDRs from the c1A10 Fab antibody: a HCDR1 comprising the amino acid sequence: GYTFTEYTMH (SEQ ID NO:28); a HCDR2 comprising the amino acid sequence: GVNPNNGGALYNQKFKG (SEQ ID NO:29); a HCDR3 comprising the amino acid sequence: RSNYRYDDAMDY (SEQ ID NO:30); a LCDR1 comprising the amino acid sequence: KSSQSLLDIDEKTYLN (SEQ ID NO:31); a LCDR2 comprising the amino acid sequence: LVSKLDS (SEQ ID NO:32); and a LCDR3 comprising the amino acid sequence: WQGTHFPQT (SEQ ID NO:33).

And in yet another example, an anti-CD200 antibody described herein can contain a paired set of CDRs from the c2aA10 Fab antibody: a HCDR1 comprising the amino acid sequence: AFNIKDHYMH (SEQ ID NO:34); a HCDR2 comprising the amino acid sequence: WIDPESGDTEYAPKFQG (SEQ ID NO:35); a HCDR3 comprising the amino acid sequence: FNGYQALDQ (SEQ ID NO:36); a LCDR1 comprising the amino acid sequence: TASSSVSSSYLH (SEQ ID NO:37); a LCDR2 comprising the amino acid sequence: STSNLAS (SEQ ID NO:38); and a LCDR3 comprising the amino acid sequence: RQYHRSPPIFT (SEQ ID NO:39).

Additional exemplary sets of CDRs of anti-CD200 antibodies are described in, e.g., U.S. Pat. No. 7,427,665. In some embodiments, the anti-CD200 antibody is samalizumab.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA) assays. See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," $2^{nd}$ Edition, Oxford University Press, NY, Oxford; Johne et al. (1993) *J Immunol Meth* 160:191-198; Jonsson et al. (1993) *Ann Biol Clin* 51:19-26; and Jonsson et al. (1991) *Biotechniques* 11:620-627.

In some embodiments, the anti-CD200 antibody can crossblock binding of another antibody that binds to an epitope within, or overlapping with, a human CD200 protein. In some embodiments, the anti-CD200 antibody can crossblock binding of an antibody that binds to an epitope within, or overlapping with, a peptide fragment of a human CD200 protein. The peptide fragment can be a fragment of a human CD200 protein having the amino acid sequence depicted in, e.g., any one of SEQ ID NOs:1 to 3. As used herein, the term "crossblocking antibody" refers to an antibody that lowers the amount of binding of anti-CD200 antibody to an epitope on a CD200 protein relative to the amount of binding of the anti-CD200 antibody to the epitope in the absence of the antibody. Suitable methods for determining whether a first antibody crossblocks binding of a second antibody to an epitope are known in the art.

Methods for identifying the epitope to which a particular antibody (e.g., an anti-CD200 antibody) binds are also known in the art. For example, the binding epitope of an anti-CD200 antibody can be identified by measuring the binding of the antibody to several (e.g., three, four, five, six, seven, eight, nine, 10, 15, 20, or 30 or more) overlapping peptide fragments of a CD200 protein (e.g., several overlapping fragments of a protein having the amino acid sequence depicted in, e.g., any one of SEQ ID NOs:1 to 3). Each of the different overlapping peptides is then bound to a unique address on a solid support, e.g., separate wells of a multi-well assay plate. Next, the anti-CD200 antibody is interrogated by contacting it to each of the peptides in the assay plate for an amount of time and under conditions that allow for the antibody to bind to its epitope. Unbound anti-CD200 antibody is removed by washing each of the wells. Next, a detectably-labeled secondary antibody that binds to the anti-CD200 antibody, if present in a well of the plate, is contacted to each of the wells, and unbound secondary antibody is removed by washing steps. The presence or amount of the detectable signal produced by the detectably-labeled secondary antibody in a well is an indication that the anti-CD200 antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) *J Immunol Methods* 160:191-8).

In some embodiments, an anti-CD200 antibody, or a CD200-binding fragment thereof, described herein binds to a human CD200 polypeptide expressed on the surface of a cell. Methods for determining whether an antibody binds to a protein expressed on the surface of a cell are known in the art and described in, e.g., Petermann et al. (2007) *J Clin Invest* 117(12):3922-9; Rijkers et al. (2008) *Mol Immunol* 45(4):1126-35; and Kretz-Rommel (2007) *J Immunol* 178(9):5595-605.

In some embodiments, an anti-CD200 antibody or CD200-binding fragment thereof described herein inhibits the interaction between CD200 protein and the CD200 receptor. Methods for determining whether an agent (such as an antibody) inhibits the interaction between CD200 and CD200R are known in the art and described in, e.g., Hatherley and Barclay (2004) *Eur J Immunol* 34(6):1688-94.

In some embodiments, the anti-CD200 antibody or CD200-binding fragment thereof inhibits the formation of osteoclasts in vitro and/or in vivo. Suitable methods for determining whether an antibody inhibits the formation of osteoclasts are known in the art and described in, e.g., PCT Publication No. WO 08/089,022 and Cui et al. (2007) *Proc Natl Acad Sci USA* 104(36):14436-14441. For example, murine bone marrow cells can be cultured in the presence of, e.g., RANKL and M-CSF in the presence or absence of an anti-CD200 antibody. A decrease in the percentage of osteoclasts formed from the bone marrow cells in the presence of the antibody as compared to the percentage of osteoclasts formed in the absence of the antibody indicates that the antibody inhibits osteoclast formation in vitro.

Since CD200 is expressed on normal cells such as endothelial cells, albeit at lower levels than on cancer cells, it could be in some embodiments advantageous to administer a variant anti-CD200 antibody (or CD200-binding fragment thereof) with a constant region modified so that it does not mediate, or has decreased ability to mediate, ADCC or CDC. Such a modification would be useful to limit damage to normal cells. CD200 expression is also upregulated on some activated normal cells (e.g., activated T cells), rendering such cells vulnerable to killing by an anti-CD200 antibody with effector function. It may be advantageous to use an anti-CD200 antibody lacking effector function to avoid killing of these cells by ADCC or CDC. The effector function of an anti-CD200 antibody can be eliminated by replacing an immunoglobulin constant region that has effector function (e.g., the IgG1 constant domain) for a constant region that does not have effector function (e.g., an IgG2/IgG4 fusion constant region). Additional methods for eliminating effector function are described below.

Effector Functions

The interaction of antibodies and antibody-antigen complexes with cells of the immune system affects a variety of responses, referred to herein as effector functions. Exemplary effector functions include Fc receptor binding, phagocytosis, down-regulation of cell surface receptors (e.g. B cell receptor; BCR), etc. Other effector functions include ADCC, whereby antibodies bind Fc receptors on natural killer (NK) cells or macrophages leading to cell death, and CDC, which is cell death induced via activation of the complement cascade (reviewed in Daeron (1997) *Annu Rev Immunol* 15:203-234; Ward and Ghetie (1995) *Therapeutic Immunol* 2:77-94; and Ravetch and Kinet (1991) *Annu Rev Immunol* 9:457-492). Such effector functions generally require the Fc region to be combined with a binding domain (e.g., an antibody variable domain) and can be assessed using various assays as herein disclosed.

Several antibody effector functions, including ADCC, are mediated by Fc receptors (FcRs), which bind the Fc region of an antibody. In ADCC, NK cells or macrophages bind to the Fc region of the antibody complex and promote lysis of the target cell. The cross-linking of FcRs on NK cells triggers perforin/granzyme-mediated cytotoxicity, whereas in macrophages this cross-linking promotes the release of mediators such as nitric oxide (NO), TNF-α, and reactive oxygen species. For CD200-positive target cells, an anti-CD200 antibody binds to the target cell and the Fc region directs effector function to the target cell. The affinity of an antibody for a particular FcR, and hence the effector activity mediated by the antibody, may be modulated by altering the amino acid sequence and/or post-translational modifications of the Fc and/or constant region of the antibody.

FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Because each FcγR subclass is encoded by two or three genes, and alternative RNA splicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. These different FcR subtypes are expressed on different cell types (reviewed in Ravetch and Kinet (1991) *Annu Rev Immunol* 9:457-492). For example, in humans, FcγRIIIB is found only on neutrophils, whereas FcγRIIIA is found on macrophages, monocytes, natural killer (NK) cells, and a subpopulation of T-cells. Notably, FcγRIIIA is the only FcR present on NK cells, one of the cell types implicated in ADCC.

FcγRI, FcγRII and FcγRIII are immunoglobulin superfamily (IgSF) receptors; FcγRI has three IgSF domains in its extracellular domain, while FcγRII and FcγRIII have only two IgSF domains in their extracellular domains. Another type of Fc receptor is the neonatal Fc receptor (FcRn). FcRn is structurally similar to major histocompatibility complex (MHC) and consists of an α-chain noncovalently bound to β2-microglobulin.

The binding site on human and murine antibodies for FcγR have been previously mapped to the so-called "lower hinge region" consisting of residues 233-239 (EU index numbering as in Kabat et al. (1991) Sequences of Proteins of Immunological Interest, 5th Ed. Public Health Service, National Institutes of Health, Bethesda, Md.). Woof et al. (1986) *Molec Immunol* 23:319-330; Duncan et al. (1988) *Nature* 332:563; Canfield and Morrison (1991) *J Exp Med* 173:1483-1491; Chappel et al. (1991) *Proc Natl Acad Sci USA* 88:9036-9040. Of residues 233-239, P238 and S239 have been cited as possibly being involved in binding.

Other previously cited areas possibly involved in binding to FcγR are: G316-K338 (human IgG) for human FcγRI (by sequence comparison only; no substitution mutants were evaluated) (Woof et al. (1986) *Molec Immunol* 23:319-330); K274-R301 (human IgG1) for human FcγRIII (based on peptides) (Sarmay et al. (1984) *Molec Immunol* 21:43-51); Y407-R416 (human IgG) for human FcγRIII (based on peptides) (Gergely et al. (1984) *Biochem Soc Trans* 12:739-743 (1984)); as well as N297 and E318 (murine IgG2b) for murine FcγRII (Lund et al. (1992) *Molec Immunol* 29:53-59).

Human effector cells are leukocytes which express one or more FcRs and perform effector functions. In certain embodiments, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. Effector cells may be isolated from a native source thereof, e.g. from blood or PBMCs.

In CDC, the antibody-antigen complex binds complement, resulting in the activation of the complement cascade and generation of the membrane attack complex. Activation of the classical complement pathway is initiated by the binding of the first component of the complement system (C1q) to antibodies (of the appropriate subclass) which are bound to their cognate antigen; thus the activation of the complement cascade is regulated in part by the binding affinity of the immunoglobulin to C1q protein. C1q and two serine proteases, C1r and C1s, form the complex C1, the first component of the CDC pathway. C1q is a hexavalent molecule with a molecular weight of approximately 460,000 and a structure in which six collagenous "stalks" are connected to six globular head regions. Burton and Woof (1992) *Advances in Immunol* 51:1-84. To activate the complement cascade, it is necessary for C1q to bind to at least two molecules of IgG1, IgG2, or IgG3, but only one molecule of IgM, attached to the antigenic target (Ward and Ghetie (1995) *Therapeutic Immunology* 2:77-94). To assess complement activation, a CDC assay, e.g. as described in Gazzano-Santoro et al. (1996) *J Immunol Methods* 202:163, can be performed.

It has been proposed that various residues of the IgG molecule are involved in binding to C1q including the Glu318, Lys320 and Lys322 residues on the CH2 domain, amino acid residue 331 located on a turn in close proximity to the same beta strand, the Lys235 and Gly237 residues located in the lower hinge region, and residues 231 to 238 located in the N-terminal region of the CH2 domain. See, e.g., Xu et al. (1993) *J Immunol* 150:152 A; PCT publication no. WO 94/29351; Tao et al. (1993) *J Exp Med* 178:661-667; Brekke et al. (1994) *Eur J Immunol* 24:2542-47; Burton et al. (1980) *Nature* 288:338-344; and U.S. Pat. Nos. 5,648,260 and 5,624,821. It has further been proposed that the ability of IgG to bind C1q and activate the complement cascade also depends on the presence, absence or modification of the carbohydrate moiety positioned between the two CH2 domains (which is normally anchored at Asn297). See, e.g., Ward and Ghetie (1995) *Therapeutic Immunology* 2:77-94. In certain embodiments, one or more of these residues may be modified, substituted, or removed or one or more amino acid residues may be inserted so as to enhance or decrease CDC activity of the anti-CD200 antibodies provided herein.

Methods for Decreasing or Eliminating Effector Function

Effector functions involving the constant region of the target-specific antibody may be modulated by altering properties of the constant or Fc region. Altered effector functions include, for example, a modulation in one or more of the following activities: ADCC, CDC, apoptosis, binding to one or more Fc-receptors, and pro-inflammatory responses. Modulation refers to an increase, decrease, or elimination of an effector function activity exhibited by a subject antibody as compared to the activity of a second antibody. In certain embodiments, the second antibody is an antibody possessing a naturally-occurring effector function that has not been modified. In particular embodiments, modulation includes situations in which an activity is abolished or completely absent. Further, in some instances, a non-variant antibody may exhibit effector function activity similar or equivalent to the activity of the chC2aB7-hG1 or the hB7V3V2-hG1 antibodies disclosed herein.

A variant constant region with altered FcR binding affinity and/or ADCC activity and/or altered CDC activity is a polypeptide which has either enhanced or diminished FcR binding activity and/or ADCC activity and/or CDC activity compared to the native or parent polypeptide or to a polypeptide comprising a native sequence or constant region. A polypeptide variant which displays increased binding to an FcR binds at least one FcR with greater affinity than the parent polypeptide. A polypeptide variant which displays decreased binding to an FcR binds at least one FcR with lower affinity than a parent polypeptide. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, a variant anti-CD200 antibody that displays altered ADCC and/or CDC activity may exhibit either increased or reduced ADCC and/or CDC activity compared to the native or parent polypeptide. For example, in some embodiments, the anti-CD200 antibody comprising a variant constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the native form of the constant region. An anti-CD200 antibody comprising a variant constant region displaying reduced ADCC and/or CDC may exhibit reduced or no ADCC and/or CDC activity as shown herein by example.

A native sequence Fc or constant region comprises an amino acid sequence identical to the amino acid sequence of a Fc or constant chain region found in nature. A variant or altered Fc or constant region comprises an amino acid sequence which differs from that of a native sequence heavy chain region by virtue of at least one amino acid modification, insertion, or deletion, for example. In certain embodiments, the variant or altered constant region has at least one amino acid substitution, insertion, and/or deletion, compared to a native sequence constant region or to the constant region of a parent polypeptide, e.g. from about one to about one hundred amino acid substitutions, insertions, and/or deletions in a native sequence constant region or in the constant region of the parent polypeptide. In some embodiments, the variant or altered constant region herein will possess at least about 70% homology (similarity) or identity with a native sequence constant region and/or with a constant region of a parent polypeptide, and in some instances at least about 75% and in other instances at least about 80% homology or identity therewith, and in other embodiments at least about 85%, 90% or 95% homology or identity therewith. The variant or altered constant region may also contain one or more amino acid deletions or insertions. Additionally, the variant constant region may contain one or more amino acid substitutions, deletions, or insertions that results in altered post-translational modifications, including, for example, an altered glycosylation pattern.

Antibodies or antigen-binding fragments thereof with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced.

Accordingly, certain aspects and methods of the present disclosure relate to anti-CD200 antibodies with altered effector functions that comprise one or more amino acid substitutions, insertions, and/or deletions. In some embodiments, such a variant anti-CD200 antibody exhibits reduced or no effector function. In some embodiments, a variant antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):44'-452). For example (and in accordance with Kabat numbering), the IgG1 and IgG4 constant regions contain $G_{249}G_{250}$ residues whereas the IgG2 constant region does not contain residue 249, but does contain $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$.

In addition to using a G2/G4 construct as described above, anti-CD200 antibodies with reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. Thus, in some embodiments, anti-CD200 antibodies with mutations within the constant region including the Ala-Ala mutation may be used to reduce or abolish effector function. According to these embodiments, the constant region of an anti-CD200 antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-CD200 antibody comprises an IgG4 framework, wherein the Ala-Ala mutation would describe a mutation(s) from phenylalanine to alanine at position 234 and/or a mutation from leucine to alanine at position 235. In another embodiment, the anti-CD200 antibody comprises an IgG1 framework, wherein the Ala-Ala mutation would describe a mutation(s) from leucine to alanine at position 234 and/or a mutation from leucine to alanine at position 235. An anti-CD200 antibody may alternatively or additionally carry other mutations, including the point mutation K322A in the CH2 domain (Hezareh et al. (2001) *J Virol* 75:12161-8). An antibody with said mutation(s) in the constant region may furthermore be a blocking or non-blocking antibody.

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, anti-CD200 antibodies may be modified to either enhance or inhibit complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821. Homodimeric antibodies with enhanced anti-tumor activity may also be prepared using heterobifunctional cross-linkers as described in Wolff et al. (1993) *Cancer Research* 53:2560-2565. Alternatively, an antibody can be engineered which has dual Fc regions and may thereby have enhanced complement lysis and ADCC capabilities. See, e.g., Stevenson et al. (1989) *Anti-Cancer Drug Design* 3:219-230.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; Newkirk et al. (1996) *Clin Exp Immunol* 106(2):259-64. Differences in effector function may be related to the IgG's ability to bind to the Fcγ receptors (FcγRs) on the effector cells. Shields et al. have shown that IgG, with variants in amino acid sequence that have improved binding to FcγR, can exhibit up to 100% enhanced ADCC using human effector cells. (2001) *J Biol Chem* 276(9):6591-604. While these variants include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30): 26733-40. An IgG that lacked a fucosylated carbohydrate linked to $Asn^{297}$ exhibited normal receptor binding to the FcγRI receptor. In contrast, binding to the FcγγRIIIA receptor was improved 50-fold and accompanied by enhanced ADCC, especially at lower antibody concentrations.

Shinkawa et al. demonstrated that an antibody to the human IL-5 receptor produced in a rat hybridoma showed more than 50% higher ADCC when compared to the antibody produced in Chinese hamster ovary cells (CHO) (Shinkawa et al. (2003) *Biol Chem* 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana et al. who changed the glycosylation pattern of chCE7, a chimeric IgG1 anti-neuroblastoma antibody. (1999) *Nat Biotechnol* 17(2): 176-80). Using tetracycline, they regulated the activity of a glycosyltransferase enzyme (GnTIII) which bisects oligosaccharides that have been implicated in ADCC activity. The ADCC activity of the parent antibody was barely above background level. Measurement of ADCC activity of the chCE7 produced at different tetracycline levels showed an optimal range of GnTIII expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation and showed that antibodies produced in this cell line were incapable of complement-mediated cytolysis. (1994) *J Exp Med* 180: 1087-1096. Thus, as known alterations that affect effector function include modifications in the glycosylation pattern or a change in the number of glycosylated residues, the present disclosure relates to a CD200 antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for altering the effector function of antibodies. For example, antibody-producing cells can be hypermutagenic, thereby generating antibodies with randomly altered polypeptide residues throughout an entire antibody molecule. See, e.g., PCT publication no. WO 05/011735. Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s).

It is further understood that effector function may vary according to the binding affinity of the antibody. For example, antibodies with high affinity may be more efficient in activating the complement system compared to antibodies with relatively lower affinity (Marzocchi-Machado et al. (1999) *Immunol Invest* 28:89-101). Accordingly, an antibody may be altered such that the binding affinity for its antigen is reduced (e.g., by changing the variable regions of the antibody by methods such as substitution, addition, or deletion of one or more amino acid residues). An anti-CD200 antibody with reduced binding affinity may exhibit reduced effector functions, including, for example, reduced ADCC and/or CDC.

Pharmaceutical Compositions and Formulations

The compositions containing an anti-CD200 antibody can be formulated as a pharmaceutical composition, e.g., for administration to a human to treat cancer. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt. See, e.g., Berge et al. (1977) *J Pharm Sci* 66:1-19.

The compositions can be formulated according to standard methods. Pharmaceutical formulation is a well-established art, and is further described in, e.g., Gennaro (2000) "Remington: The Science and Practice of Pharmacy," 20th Edition, Lippincott, Williams & Wilkins (ISBN: 0683306472); Ansel et al. (1999) "Pharmaceutical Dosage Forms and Drug Delivery Systems," 7th Edition, Lippincott Williams & Wilkins Publishers (ISBN: 0683305727); and Kibbe (2000) "Handbook of Pharmaceutical Excipients American Pharmaceutical Association," 3rd Edition (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an anti-CD200 antibody intended for systemic or local delivery can be in the form of injectable or infusible solutions.

Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody described herein in the required amount in an appropriate solvent with one or a combination of ingredients enumerated above, as required, followed by filtered sterilization. Generally, dispersions are prepared by incorporating an anti-CD200 antibody described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the antibody described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

In certain embodiments, the anti-CD200 antibody can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. (See, e.g., J. R. Robinson (1978) "Sustained and Controlled Release Drug Delivery Systems," Marcel Dekker, Inc., New York.)

In some embodiments, an antibody described herein can be formulated in a composition suitable for intrapulmonary administration (e.g., for administration via nebulizer) to a mammal such as a human. Methods for preparing such compositions are well known in the art and described in, e.g., U.S. Patent Application Publication No. 20080202513; U.S. Pat. Nos. 7,112,341 and 6,019,968; and PCT Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 20070235029, PCT Publication No. WO 00/69887; and U.S. Pat. No. 5,997,848.

In some embodiments, an anti-CD200 antibody described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

In some embodiments, an anti-CD200 antibody described herein can be formulated with one or more additional active agents useful for treating cancer or ameliorating a symptom thereof. For example, an anti-CD200 antibody can be formulated with a genotoxic agent or a chemotherapeutic agent, or one or more kinase inhibitors. The genotoxic or chemotherapeutic agent can be, but is not limited to: carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gemcitabine, cisplatin (CDDP), adriamycin (ADR), or an analog of any of the aforementioned. Kinase inhibitors include, e.g., one or more of: trastuzumab, gefitinib, erlotinib, imatinib mesylate, or sunitinib malate. Additional agents are known in the art and described herein.

When the anti-CD200 antibody is to be used in combination with a second active agent, or when two or more different anti-CD200 antibodies are to be used, the agents can be formulated separately or together. For example, the respective pharmaceutical compositions can be mixed, e.g., just prior to administration, and administered together or can be administered separately, e.g., at the same or different times (see below).

As described above, a composition can be formulated such that it includes a therapeutically effective amount of an anti-CD200 antibody or the composition can be formulated to include a sub-therapeutic amount of the antibody and a sub-therapeutic amount of one or more additional active agents such that the components in total are therapeutically effective for treating a cancer. In some embodiments, a composition can be formulated to include two or more anti-CD200 antibodies, each at sub-therapeutic doses, such that the antibodies in combination are at a concentration that is therapeutically effective for treating a cancer in a human. Methods for determining a therapeutically effective dose of an anti-CD200 antibody are known in the art and described herein.

Methods for Producing an Anti-CD200 Antibody

Suitable methods for producing an anti-CD200 antibody, or CD200-binding fragments thereof, in accordance with the disclosure are known in the art (see, e.g., U.S. Pat. Nos. 7,427,665; 7,435,412; and 7,408,041, the disclosures of each of which are incorporated herein by reference in their entirety) and described herein. For example, monoclonal anti-CD200 antibodies may be generated using human CD200-expressing cells, a human CD200 polypeptide, or an antigenic fragment of a human CD200 polypeptide as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to CD200 or a fragment thereof.

Moreover, antibodies derived from recombinant libraries ("phage antibodies") may be selected using CD200-expressing cells, or polypeptides derived therefrom, as bait to isolate the antibodies or polypeptides on the basis of target specificity. The production and isolation of non-human and chimeric anti-CD200 antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to a polycistronic (e.g., bicistronic) DNA sequence encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPM1 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. No. 5,427,908; U.S. Pat. No. 5,508,717; Smith (1985) *Science* 225:1315-1317; Parmley and Smith (1988) *Gene* 73:305-318; De La Cruz et al. (1988) *J Biol Chem* 263:4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al. (1999) *Cancer Metastasis Rev* 18(4):421-5; and Taylor et al. (1992) *Nucleic Acids Res* 20: 6287-6295; Tomizuka et al. (2000) *Proc Natl Acad Sci USA* 97(2): 722-727, the contents of each of which are incorporated herein by reference in their entirety.

The cell culture supernatants are screened for the desired antibodies, preferentially by immunofluorescent staining of CD200-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAF-cellulose and/or (immuno-) affinity chromatography, e.g., affinity chromatography with one or more surface polypeptides derived from a CD200-expressing cell line or synthetic CD200 fragment peptides, or with Protein-A or -G.

Another embodiment provides a process for the preparation of a bacterial cell line secreting antibodies directed against a human CD200 protein in a suitable mammal. For example a rabbit is immunized with pooled samples from CD200-expressing tissue or cells or CD200 polypeptide or fragments thereof. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a human CD200 protein. In that process, a suitable mammal, for example a Balb/c mouse, is immunized with one or more polypeptides or antigenic fragments of CD200 or with one or more polypeptides or antigenic fragments derived from a CD200-expressing cell, the CD200-expressing cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a protein fragment of human CD200 are fused with cells of the myeloma cell line PAI or the myeloma cell line Sp2/0-Ag 14. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally a peptide fragment of human CD200 several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application (e.g., methods for treating or preventing a cancer in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. See, e.g., Jakobovits et al. (1993) *Proc Natl Acad Sci USA* 90:2551; Jakobovits et al. (1993) *Nature* 362:255-258; Bruggemann et al. (1993) *Year in Immunol* 7:33; and Duchosal et al. (1992) *Nature* 355:258. Transgenic mouse strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a human CD200 protein, fragments thereof, or cells expressing CD200 protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J Mol Biol* 227: 381; Marks et al. (1991) *J Mol Biol* 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983) *Hybridoma* 2:361-367, the contents of each of which are incorporated herein by reference in their entirety.

For the generation of human antibodies, also see Mendez et al. (1998) *Nature Genetics* 15:146-156, and Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 20030229905 A1, 20040010810 A1, 20040093622 A1, 20060040363 A1, 20050054055 A1, 20050076395 A1, and 20050287630 A1.

See also International Patent Application Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Application-Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int Immunol* 5: 647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *International Immunology* 6: 579-591; Tuaillon et al. (1995) *J. Immunol.* 154: 6453-65; Fishwild et al. (1996) *Nature Biotechnology* 14: 845; and Tuaillon et al. (2000) *Eur Immunol* 10: 2998-3005, the disclosures of each of which are hereby incorporated by reference in their entirety.

In certain embodiments, de-immunized anti-CD200 antibodies or antigen-binding fragments thereof are provided. De-immunized antibodies or antigen-binding fragments thereof are those modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-CD200 antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, a recombinant DNA comprising an insert coding for a heavy chain variable domain and/or for a light chain variable domain of an anti-CD200 antibody or a CD200 protein-expressing cell line is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-CD200 antibodies, or the CD200-expressing cell line, can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-CD200 antibody or a CD200-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 antibody or antigen-binding fragment (e.g., Fab, Fv, single-chain scFv, Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as E. coli gpt (Mulligan and Berg (1981) Proc Natl Acad Sci USA, 78:2072-2076) or Tn5 neo (Southern and Berg (1982) J Mol Appl Genet. 1:327-341). The selectable marker gene can be either linked to the DNA gene sequences to be expressed, or introduced into the same cell by co-transfection (Wigler et al. (1979) Cell 16:777-785). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147-7151), polyoma virus (Deans et al. (1984) Proc Natl Acad Sci USA 81:1292-1296), or SV40 virus (Lusky and Botchan (1981) Nature 293:79-81).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) Mol Cell Biol 3:280-289; Cepko et al. (1984) Cell 37:1053-1062; and Kaufman (1985) Proc Natl Acad Sci USA 82:689-693.

As is evident from the disclosure, the anti-CD200 antibodies can be used in therapies (e.g., therapies for treating a cancer), including combination therapies, as well as in the monitoring of disease progression.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the CD200 antigen on a cell (such as, e.g., an immune cell), the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) Nature 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) Methods Enzymol 121:210-228; PCT Publication No. WO 96/27011; Brennan et al. (1985) Science 229:81-83; Shalaby et al. J Exp Med (1992) 175:217-225; Kostelny et al. (1992) J Immunol 148 (51:1547-1553; Hollinger et al. (1993) Proc Natl Acad Sci USA 90:6444-6448; Gruber et al. (1994) J Immunol 152:5368-5474; and Tutt et al. (1991) J Immunol 147:60-69. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368-5374. Alternatively, the antibodies can be "linear antibodies" as described in, e.g., Zapata et al. (1995) Protein Eng 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) Nat Biotechnol 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024,188 and WO 07/024,715, the disclosures of each of which are incorporated herein by reference in their entirety.

In some embodiments, anti-CD200 antibodies can be modified, e.g., with a moiety that improves the stabilization and/or retention of the antibodies themselves in circulation, e.g., in blood, serum, or other tissues. For example, an anti-CD200 antibody described herein can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody in a subject's body (e.g., blood or tissue) by at least 1.5 (e.g., at least 2, 5, 10, 15, 20, 25, 30, 40, or 50 or more) fold.

Biological Samples and Sample Collection

Suitable biological samples for use in the methods described herein include any biological fluid, population of cells, or tissue or fraction thereof, which includes one or more white blood cells and/or one or more red blood cells. A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a biological fluid such as urine, whole blood or a fraction thereof (e.g., plasma), saliva, semen, sputum, cerebral spinal fluid, tears, or mucus. A biological sample can be further fractionated, if desired, to a fraction containing particular cell types. For example, a whole blood sample can be fractionated into serum or into fractions containing particular types of blood cells such as red blood cells or white blood cells (leukocytes). If desired, a biological sample can be a combination of different biological samples from a subject such as a combination of a tissue and fluid sample.

The biological samples can be obtained from a subject, e.g., a subject having, suspected of having, or at risk of developing, a cancer (e.g., B-CLL), an inflammatory condition, or a bone disorder (e.g., a CD200-associated bone disorder). Any suitable methods for obtaining the biological samples can be employed, although exemplary methods include, e.g., phlebotomy, swab (e.g., buccal swab), lavage, or fine needle aspirate biopsy procedure. Non-limiting examples of tissues susceptible to fine needle aspiration include lymph node, lung, thyroid, breast, and liver. Biological samples can also be obtained from bone marrow. Samples can also be collected, e.g., by microdissection (e.g., laser capture microdissection (LCM) or laser microdissection (LMD)), bladder wash, smear (PAP smear), or ductal lavage.

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes in the cells (e.g., changes in osmolarity or pH) or denaturation of cell surface proteins (e.g., GPI-linked proteins) or GPI moieties on the surface of the cells. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in molecular biology*, Humana Press; Masters (2000) "Animal cell culture: a practical approach," volume 232 of *Practical approach series*, Oxford University Press; and Jones (1996) "Human cell culture protocols," volume 2 of *Methods in molecular medicine*, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

Biomarkers and Applications

The inventors have identified and provided herein several biomarkers consistent with the production in a human of a desired immunomodulatory effect by an anti-CD200 antibody administered to the human. A "desired immunomodulatory effect," an "anti-CD200 antibody-associated immunomodulatory effect," and grammatically similar terms, as used herein, refer to a measurable, desirable immunological effect in a human attributable to the biological activity of an anti-CD200 antibody administered to the human. For example, the inventors have observed that following administration of an anti-CD200 antibody to a human, the concentration of circulating CD200$^+$ lymphocytes (e.g., subsets of CD200+ T cells including, e.g., CD200$^+$/CD4$^+$ T cells and/or activated CD200$^+$/CD4$^+$ T cells) is reduced in the human as measured by a reduction in the concentration of such cells in the blood. Also observed was that upon administration of an anti-CD200 antibody, the expression level of CD200R by at least one leukocyte subset (e.g., CD4$^+$ T cells) is increased. While not being bound by any particular theory or mechanism of action, the inventors believe that monitoring a patient treated with an anti-CD200 antibody for a change (e.g., an increase or decrease) in one or more of these biomarkers is useful for, among other things, determining whether the anti-CD200 antibody is capable of producing a biological effect in the human to whom the antibody is administered. Moreover, monitoring changes in one or more of the biomarkers is also useful for identifying a dose—a threshold dose (or a dosing schedule)—of an anti-CD200 antibody, such as samalizumab, that by virtue of its immunomodulatory effect in the human, is sufficient to achieve a clinically-meaningful effect in the disease (i.e., sufficient to treat a disease such as cancer). Several B-CLL patients administered samalizumab exhibited clinically stable or improved disease as determined by serial assessments of peripheral blood counts and CT scans. A desired immunomodulatory effect of the antibody was observed in all of these patients as reflected in a change (e.g., an increase or decrease) in one or more of the biomarkers described herein.

Thus, in accordance with the present disclosure, to determine whether an anti-CD200 antibody (e.g., a variant anti-CD200 antibody that has reduced or no effector function) has produced a desired immunomodulatory effect (e.g., an anti-CD200 antibody-associated immunomodulatory effect) in the human (and thereby the human has been administered a dose of the antibody sufficient to affect the treatment of the patient via, among other things, its immunomodulatory activity), a practitioner can measure the concentration of CD200$^+$ leukocytes (e.g., T cells) in a blood sample from a human administered an anti-CD200 antibody. A reduction in the concentration of CD200$^+$ leukocytes (e.g., T cells) in the blood sample as compared to the concentration of CD200+ leukocytes (e.g., T cells) in a control blood sample indicates that the anti-CD200 antibody has produced a desired immunomodulatory effect in the human. In some embodiments, the practitioner need not measure first hand the concentration of CD200+ leukocytes (e.g., T cells) in the blood sample. For example, a practitioner (e.g., a medical professional or a diagnostic scientist or technician) provided with information regarding: (i) the concentration of CD200+ leukocytes (e.g., T cells) in a blood sample from the human administered the antibody and (ii) a control CD200+ leukocyte concentration can determine whether the antibody has produced a desired immunomodulatory effect in the human using the information, e.g., comparing the concentration of CD200+ leukocytes (e.g., T cells) in the blood sample with the concentration of such cells in the control sample, wherein reduction in the concentration of CD200+ leukocytes (e.g., T cells) in the blood sample as compared to a control concentration of CD200+ leukocytes (e.g., T cells) indicates that the anti-CD200 antibody has produced a desired immunomodulatory effect in the human.

Methods for measuring the concentration of CD200+ cells (e.g., CD200+ T cells) are well known in the art and include, among other methods, flow cytometry. See, e.g., Chen et al. (2009) *Mol Immunol* 46(10):1951-1963. A suitable method for detecting and/or measuring the concentration of CD200+ T cells is also set forth in the working examples. In some embodiments, a practitioner can interrogate a biological sample obtained from a post-treatment patient (a patient to which an anti-CD200 antibody has already been administered) for the concentration of cells of a particular subset of CD200+ leukocytes (e.g., T cells). For example, a practitioner can determine the concentration of CD200+/CD4+ T cells and/or the concentration of activated CD200+/CD4+ T cells present in a biological sample from a post-treatment patient. In some embodiments, a practitioner can determine the concentration of CD200+/CD8+ cells. In each case, a reduction in the concentration of CD200+ T cells of a given subset, as compared to control concentration of CD200+ T cells of the same histological type, indicates that the anti-CD200 antibody has produced in the human a desired immunomodulatory effect.

As described above, determining whether an anti-CD200 antibody (e.g., a variant anti-CD200 antibody with decreased or no effector function) has produced a desired immunomodulatory effect in a human can be performed by comparing the concentration of CD200 T cells in a biological sample obtained from a patient following administration of the anti-CD200 antibody (the post-treatment CD200+ T cell concentration) to the concentration of CD200+ cells in a control sample. In some embodiments, control sample is obtained from the patient prior to administering to the patient the anti-CD200 antibody. In some embodiments, the control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered an anti-CD200 antibody (e.g., a control concentration of CD200+ cells of the same histological type can be an average of the concentration of the cells in one or more control samples obtained from patients who have not been administered an anti-CD200 antibody. In some embodiments, the control sample can be or can be based on, e.g., a collection of samples obtained from one or more (e.g., two, three, four, five, six, seven, eight, nine, 10, 15, 20, 25, 30, 35, or 40 or more) individuals suffering from the same cancer or different types of cancers, but who have not been administered an anti-CD200 antibody. For example, to determine whether an anti-CD200 antibody has produced a desired immunomodulatory effect in a human administered the antibody, a practitioner can compare the post-treatment CD200+ T cell concentration to the typical concentration, or average concentration, of CD200+ T cells of the same histological type present in humans who have not been administered an anti-CD200 antibody or at least do not have a detectable level of an anti-CD200 antibody in a biological sample obtained from the humans.

In some embodiments, a post-treatment CD200+ T cell concentration that is at least 5% less than the control concentration indicates that a desired immunomodulatory effect has occurred in the human administered the anti-CD200 antibody. In some embodiments, a post-treatment CD200+ T cell concentration that is at least 10 (e.g., 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, or more than 80) % less than the control concentration indicates that a desired immunomodulatory effect has occurred in the human administered the anti-CD200 antibody.

In some embodiments, determining whether an anti-CD200 antibody (e.g., a variant anti-CD200 antibody having reduced or no effector function) has produced a desired immunomodulatory effect in a human can be performed by querying whether the post-treatment CD200+ T cell concentration falls within a predetermined range indicative of the occurrence of a desired immunomodulatory effect by an anti-CD200 antibody in a human. In some embodiments, determining whether an anti-CD200 antibody has produced a desired immunomodulatory effect in a human can include querying if the post-treatment CD200+ T cell concentration for a given histological type of CD200+ T cell falls above or below a predetermined cut-off value. A cut-off value is typically the concentration of CD200+ T cells of a given histological type above or below which is considered indicative of a certain phenotype—namely the occurrence of a desired immunomodulatory effect in a human produced by an anti-CD200 antibody.

In some embodiments, to determine whether an anti-CD200 antibody (e.g., a variant anti-CD200 antibody that has reduced or no effector function) has produced a desired immunomodulatory effect in the human (and thereby the human has been administered a dose of the antibody sufficient to affect the treatment of the patient via, among other things, its immunomodulatory activity), a practitioner can quantify the expression of CD200 by T cells (e.g., CD4+ T cells, CD8+ T cells, or activated CD4+ T cells) in a blood sample from a human administered an anti-CD200 antibody. A reduction in the expression level of CD200 by T cells in the blood sample as compared to the expression level of CD200 by T cells of the same histological type in a control blood sample indicates that the anti-CD200 antibody has produced a desired immunomodulatory effect in the human. As described above, the practitioner need not measure first hand the expression level of CD200 by the T cells in the blood sample. For example, a practitioner provided with information regarding: (i) the expression level of CD200 by T cells in a blood sample from the human administered the antibody and (ii) the expression level of CD200 by T cells in a control blood sample can determine whether the antibody has produced a desired immunomodulatory effect in the human using the information, e.g., comparing the expression level of CD200 by T cells in the blood sample with the expression level of CD200 by such cells in the control sample, wherein reduction in the level of CD200 expression by the T cells in the blood sample as compared to expression level of CD200 by T cells of the same histological type in the control sample indicates that the anti-CD200 antibody has produced a desired immunomodulatory effect in the human. Suitable methods for quantifying the expression level of CD200 by cells (e.g., leukocytes such as T cells) are known in the art and described herein.

The inventors also observed that upon administration of an anti-CD200 antibody, the expression level of CD200R by a variety of leukocyte subsets is increased. While not being bound by any particular theory or mechanism of action, the inventors believe that an increase in CD200R expression by leukocytes is potentially a compensatory response by these cells to the reduction of cellular CD200 expression induced by the anti-CD200 antibody. Thus, CD200R expression by leukocytes serves as an indirect biomarker to monitor (or detect) the immunomodulatory effect of an anti-CD200 antibody on CD200 expression by leukocytes in the human to which the anti-CD200 antibody is administered. In some embodiments, to determine whether an anti-CD200 antibody has produced a desired immunomodulatory effect in the human (and thereby the human has been administered a dose of the antibody sufficient to affect the treatment of the patient via, among other things, its immunomodulatory activity), a practitioner can measure the expression level of CD200R by a plurality of leukocytes (e.g., a plurality of leukocytes of a given histological type) in a biological sample (e.g., a blood sample) obtained from a human following administration of the anti-CD200 antibody (the post-treatment CD200R expression level), wherein an increase in post-treatment CD200R expression level as compared to the CD200R expression level by leukocytes of the same histological type in a control sample indicates that the anti-CD200 antibody has produced in the human a desired immunomodulatory effect. In some embodiments, the practitioner need not measure first hand the expression level of CD200R by leukocytes in the biological sample. For example, a practitioner (e.g., a medical professional or a diagnostic scientist or technician) provided with information regarding: (i) the expression level of CD200R by a plurality of leukocytes in a blood sample from the human administered the antibody and (ii) a control expression level (e.g., the expression level of CD200R by leukocytes of the same histological type in a control sample) can determine whether the antibody has produced a desired immunomodulatory effect in the human using the information, e.g., comparing the CD200R expression level by the leukocytes in the biological sample with the control expression level, wherein an increase in the CD200R expression level by the leukocytes, as compared to the control expression level, indicates that the anti-CD200 antibody has produced a desired immunomodulatory effect in the human.

Methods for quantifying the expression level of CD200 and/or CD200R by a cell or a population of cells are well known in the art and include, among other methods, Western blotting, dot blotting, and flow cytometry, which are useful for quantifying expression of protein, or reverse transcriptase polymerase chain reaction (RT-PCR) and Northern blotting analysis for quantifying expression of mRNA. See, e.g., Walker et al. (2009) *Exp Neurol* 215(1):5-19; Rijkers et al. (2008) *Mol Immunol* 45(4):1126-1135; and Voehringer et al. (2004) *J Biol Chem* 279(52):54117-54123. See generally Sambrook et al. (1989) "Molecular Cloning: A Laboratory Manual, $2^{nd}$ Edition," Cold Spring Harbor Laboratory Press, Cold Spring Harbor, N.Y. and Ausubel et al. (1992) "Current Protocols in Molecular Biology," Greene Publishing Associates. A suitable method for detecting and/or quantifying the expression of CD200 or CD200R by leukocytes is also set forth in the working examples. In some embodiments, a practitioner can interrogate a biological sample (e.g., a blood sample) obtained from a post-treatment patient (a patient to which an anti-CD200 antibody has been administered) for the CD200 and/or CD200R expression level (e.g., the average expression level) by a plurality of leukocytes of a given histological type. For example, a practitioner can determine the expression level or average expression level of CD200R by a plurality of $CD4^+$ T cells, $CD8^+$ T cells, activated $CD4^+$ T cells, NK T cells, or $CD21^+/CD25^+/Fox3P^+$ T cells. In one instance, an increase in CD200R expression by a given subset of leukocytes, as compared to control expression level (e.g., the average level of expression of leukocytes of the same histological type in a biological sample obtained from the patient prior to administration of the antibody), indicates that the anti-CD200 antibody has produced in the human a desired immunomodulatory effect.

In some embodiments, a post-treatment CD200R expression level that is at least 1.5-fold greater than the control expression level (that is, the level of expression of CD200R by leukocytes of the same histological type in a control sample) indicates that a desired immunomodulatory effect has occurred in the human administered the anti-CD200 antibody. In some embodiments, a post-treatment CD200R expression level that is at least 2 (e.g., at least 2.5, 3, 3.5, 4, 4.5, 5, 5.5, 6, 6.5, 7, 7.5, 8, 8.5, 9, or 10 or more)-fold greater than the control expression level indicates that a desired immunomodulatory effect has occurred in the human administered the anti-CD200 antibody. In some embodiments, a post-treatment CD200R expression level that is at least 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, or 250 or more) % greater than the control expression level indicates that a desired immunomodulatory effect has occurred in the human administered the anti-CD200 antibody.

In some embodiments, a post-treatment CD200 expression level that is at least 5 (e.g., 6, 7, 8, 9, 10, 11, 12, 13, 14, 15, 16, 17, 18, 19, 20, 25, 30, 35, 40, 45, 50, 55, 60, 65, 70, 75, 80, 85, or 90 or more) % lower than the control expression level indicates that a desired immunomodulatory effect has occurred in the human administered the anti-CD200 antibody.

In some embodiments, the control sample is a biological sample obtained from the subject human prior to administering to the subject human the anti-CD200 antibody. (That is, e.g., the control CD200R expression level can be the expression level of CD200R by leukocytes of the same histological type in a biological sample obtained from the subject human prior to administering to the subject human the anti-CD200 antibody). In some embodiments, the control CD200 or CD200R expression level can be based on, e.g., the average expression level of CD200 or CD200R by leukocytes of the same histological type obtained from one or more (e.g., two, three, four, five, six, seven, eight, nine, 10, 15, 20, 25, 30, 35, or 40 or more) healthy individuals that have not been administered an anti-CD200 antibody. The control CD200 or CD200R expression level can be based on, e.g., the average expression level of CD200 or CD200R by leukocytes of the same histological type obtained from one or more (e.g., two, three, four, five, six, seven, eight, nine, 10, 15, 20, 25, 30, 35, or 40 or more) individuals suffering from the same cancer or different types of cancers, but who have not been administered an anti-CD200 antibody. For example, to determine whether an anti-CD200 antibody has produced a desired immunomodulatory effect in a human administered the antibody, a practitioner can compare the post-treatment CD200R expression level to the typical expression level, or average expression level, of CD200R by leukocytes of the same histological type in a biological sample obtained from humans who have not been administered an anti-CD200 antibody or at least do not have a detectable level of an anti-CD200 antibody in the biological sample.

In some embodiments, determining whether an anti-CD200 antibody (e.g., a variant anti-CD200 antibody having decreased or no effector function) has produced a desired immunomodulatory effect in a human can be performed by querying whether the post-treatment CD200 or CD200R expression level falls within a predetermined range indicative of the occurrence of an immunomodulatory effect by an anti-CD200 antibody in a human. In some embodiments, determining whether an anti-CD200 antibody has produced a desired immunomodulatory effect in a human can include querying if the post-treatment CD200 or CD200R expression level by a given histological type of leukocytes falls above or below a predetermined cut-off value. In this case, the cut-off value is typically the level of expression (e.g., mRNA or protein expression) by leukocytes of a given histological type above or below which is considered indicative of a certain phenotype—namely the occurrence of a desired immunomodulatory effect in a human produced by an anti-CD200 antibody.

In some embodiments, to determine whether an anti-CD200 antibody (e.g., a variant anti-CD200 antibody that has reduced or no effector function) has produced a desired immunomodulatory effect in the human (and thereby the human has been administered a dose of the antibody sufficient to affect the treatment of the patient via, among other things, its immunomodulatory activity), a practitioner can measure the concentration of $CD200R^+$ leukocytes in a blood sample from a human administered an anti-CD200 antibody. An increase in the concentration of $CD200R^+$ leukocytes in the blood sample as compared to the concentration of $CD200R^+$ leukocytes of the same histological type in a control blood sample indicates that the anti-CD200 antibody has produced a desired immunomodulatory effect in the human. A practitioner (e.g., a medical professional or a diagnostic scientist or technician) provided with information regarding: (i) the concentration of $CD200R^+$ leukocytes in a blood sample from the human administered the antibody and (ii) a control $CD200R^+$ leukocyte concentration can determine whether the antibody has produced a desired immunomodulatory effect in the human using the information, e.g., comparing the concentration of $CD200R^+$ leukocytes in the blood sample with the concentration of such cells in the control sample, wherein an increase in the concentration of $CD200R^+$ leukocytes in the blood sample as compared to a control concentration of $CD200R^+$ leukocytes indicates that the anti-CD200 antibody has produced a desired immunomodulatory effect in the human.

In some embodiments of any of the methods described herein, the same practitioner may administer the antibody to the human prior to determining whether a desired immunomodulatory effect has occurred in the human, whereas in some embodiments, the practitioner who administers the antibody to the patient is different from the practitioner who determines whether a desired immunomodulatory effect has occurred in the human. In some embodiments, the practitioner may obtain a biological sample (e.g., the blood sample) from the human prior to administration of the antibody. In some embodiments, the practitioner may obtain a biological sample (e.g., a blood sample) from the human following the administration of the antibody to the human. In some embodiments, the post-treatment sample can be obtained from the human less than 48 (e.g., less than 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, nine, eight, seven, six, five, four, three, two, or even less than one) hour following administration of the anti-CD200 antibody to the human. In some embodiments, the post-treatment sample can be obtained from the human less than 20 (e.g., less than 19, 18, 17, 16, 15, 14, 13, 12, 11, 10, nine, eight, seven, six, five, four, three, two, or one) day(s) after administering to the human the anti-CD200 antibody.

In some embodiments, the biological sample is obtained from the human no more than 20 (e.g., no more than 19, 18, 17, 16, 15, 14, 13, 12, 11, 10, nine, eight, seven, six, five, four, three, two, or one) day(s) after the antibody is administered to the human.

In some embodiments, determining whether an anti-CD200 antibody has produced a desired immunomodulatory effect in a human can include (i) measuring the concentration of $CD200^+$ T cells in a biological sample obtained from a human prior to administration to the human of an anti-CD200 antibody to thereby obtain a pre-treatment CD200+ T cell concentration; (ii) administering to the human the antibody; and (iii) measuring the concentration of $CD200^+$ T cells in a blood sample obtained from the human to thereby obtain a post-treatment $CD200^+$ T cell concentration, wherein a reduction in the post-treatment $CD200^+$ T cell concentration as compared to the pre-treatment $CD200^+$ T cell concentration indicates that the antibody has produced a desired immunomodulatory effect in the human. In some embodiments, determining whether an anti-CD200 antibody has produced a desired immunomodulatory effect in a human can include (i) measuring the concentration of $CD200R^+$ leukocytes in a biological sample obtained from a human prior to administration to the human of an anti-CD200 antibody to thereby obtain a pre-treatment $CD200R^+$ leukocyte concentration; (ii) administering to the human the antibody; and (iii) measuring the concentration of $CD200R^+$ leukocytes in a blood sample obtained from the human to thereby obtain a post-treatment $CD200R^+$ leukocyte concentration, wherein an increase in the post-treatment $CD200R^+$ leukocyte concentration as compared to the pre-treatment $CD200R^+$ leukocyte concentration indicates that the antibody has produced a desired immunomodulatory effect in the human. In some embodiments, determining whether an anti-CD200 antibody is biologically active in a human includes: (i) quantifying the level of CD200R expression by a plurality of leukocytes in a biological sample from a human prior to administration to the human of an anti-CD200 antibody to thereby obtain a pre-treatment CD200R expression level; (ii) administering to the human the anti-CD200 antibody; and (iii) quantifying the level of CD200R expression by a plurality of leukocytes in a biological sample from the human obtained after the administration of the antibody to thereby obtain a post-treatment CD200R expression level, wherein an increase in post-treatment CD200R expression level as compared to the pre-treatment CD200R expression level indicates that the antibody has produced a desired immunomodulatory effect in the human. In some embodiments, determining whether an anti-CD200 antibody is biologically active in a human includes: (i) quantifying the level of CD200 expression by a plurality of leukocytes in a biological sample from a human prior to administration to the human of an anti-CD200 antibody to thereby obtain a pre-treatment CD200 expression level; (ii) administering to the human the anti-CD200 antibody; and (iii) quantifying the level of CD200 expression by a plurality of leukocytes in a biological sample from the human obtained after the administration of the antibody to thereby obtain a post-treatment CD200 expression level, wherein a decrease in post-treatment CD200 expression level as compared to the pre-treatment CD200 expression level indicates that the antibody has produced a desired immunomodulatory effect in the human. In some embodiments, determining whether an anti-CD200 antibody is biologically active in a human includes: (i) measuring the concentration of activated T cells in a biological sample from a human prior to administration to the human of an anti-CD200 antibody to thereby determine a pre-treatment activated T cell concentration; (ii) administering to the human the anti-CD200 antibody; and (iii) measuring the concentration of activated T cells of same histological type as in (i) to thereby determine a post-treatment activated T cell concentration, wherein an increase in the post-treatment activated T cell concentration, as compared to the pre-treatment activated T cell concentration, indicates that the antibody has produced a desired immunomodulatory effect in the human. In some embodiments, determining whether an anti-CD200 antibody is biologically active in a human includes: (i) measuring the concentration of regulatory T cells in a biological sample from a human prior to administration to the human of an anti-CD200 antibody to thereby determine a pre-treatment regulatory T cell concentration; (ii) administering to the human the anti-CD200 antibody; and (iii) measuring the concentration of regulatory T cells of same histological type as in (i) to thereby determine a post-treatment regulatory T cell concentration, wherein a decrease in the post-treatment regulatory T cell concentration, as compared to the pre-treatment regulatory T cell concentration, indicates that the antibody has produced a desired immunomodulatory effect in the human. In some embodiments, determining whether an anti-CD200 antibody is biologically active in a human includes: (i) determining the ratio of percent activated T cells to percent regulatory T cells in a biological sample from a human prior to administration to the human of an anti-CD200 antibody to thereby determine a pre-treatment ratio; (ii) administering to the human the anti-CD200 antibody; and (iii) measuring the ratio of percent activated T cells to percent regulatory T cells of same histological type as in (i) to thereby determine a post-treatment ratio, wherein an increase in the post-treatment ratio, as compared to the pre-treatment ratio, indicates that the antibody has produced a desired immunomodulatory effect in the human. The ratio can be increased to, e.g., at least 2:1 (e.g., at least 3:1, 4:1, 5:1, 6:1, or even 7:1 or more).

In some embodiments, the above method steps can be performed by more than one practitioner. For example, one practitioner may analyze (e.g., measure the concentration of CD200+ T cells or quantify the expression level of CD200R by leukocytes in) the pre- and post-treatment samples obtained from the human. Another practitioner may receive information regarding the analysis of the samples by the first practitioner to thereby determine whether the anti-CD200 antibody has produced a desired immunomodulatory effect in the human. In some embodiments, yet another practitioner may obtain a pre-treatment biological sample from a patient and a fourth practitioner may obtain a post-treatment biological sample from the patient. In some embodiments, all steps are carried out by the same practitioner.

Further observed was that administration of an anti-CD200 antibody to a human results in one or more of: (a) an increase in the concentration of activated T cells; (b) a decrease in the concentration of regulatory T cells; and (c) an increase in the ratio of percent activated T cells to percent regulatory T cells, or a ratio of percent activated T cells to percent regulatory T cells of at least 2:1 (e.g., at least 3:1, 4:1, 5:1, 6:1, or even 7:1 or more). Thus, in accordance with the present disclosure, to determine whether an anti-CD200 antibody (e.g., a variant anti-CD200 antibody that has reduced or no effector function) has produced a desired immunomodulatory effect (e.g., an anti-CD200 antibody-associated immunomodulatory effect) in the human (and thereby the human has been administered a dose of the antibody sufficient to affect the treatment of the patient via, among other things, its immunomodulatory activity), a practitioner can measure the concentration of activated T cells in a biological sample from a human administered an anti-CD200 antibody. An increase in the concentration of activated T cells in the blood sample as compared to the concentration of activated T cells in a control blood sample indicates that the anti-CD200 antibody has produced a desired immunomodulatory effect in the human. In accordance with the disclosure, to determine whether an anti-CD200 antibody has produced a desired immunomodulatory effect in the human, a practitioner can measure the concentration of regulatory T cells in a biological sample obtained from the human, wherein a decrease in the concentration of regulatory T cells in the biological sample, as compared to the concentration of regulatory T cells in a control sample, indicates that a desired immunomodulatory effect has occurred in the human. As described above, the practitioner need not measure first hand the concentration of activated T cells in the blood sample.

Methods for measuring the concentration of activated T cells (e.g., activated $CD4^+$ T cells) or regulatory T cells are well known in the art and include, among other methods, flow cytometry. As described above, determining whether an anti-CD200 antibody (e.g., a variant anti-CD200 antibody with decreased or no effector function) has produced a desired immunomodulatory effect in a human can be performed by comparing the concentration of activated T cells and/or regulatory T cells in a biological sample obtained from a patient following administration of the anti-CD200 antibody (the post-treatment activated T cell concentration) to the concentration of activated T cells in a control sample. The control sample can be, e.g., a biological sample obtained from the subject human prior to administering to the subject human the anti-CD200 antibody. The control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered an anti-CD200 antibody (e.g., a control concentration of activated cells of the same histological type can be an average of the concentration of the cells in one or more control samples obtained from patients who have not been administered an anti-CD200 antibody). For example, to determine whether an anti-CD200 antibody has produced a desired immunomodulatory effect in a human administered the antibody, a practitioner can compare the post-treatment activated T cell concentration to the typical concentration, or average concentration, of activated T cells of the same histological type present in humans who have not been administered an anti-CD200 antibody or at least do not have a detectable level of an anti-CD200 antibody in a biological sample obtained from the humans.

In some embodiments, a post-treatment activated T cell concentration that is at least 5% greater than the control concentration indicates that a desired immunomodulatory effect has occurred in the human administered the anti-CD200 antibody. In some embodiments, a post-treatment activated T cell concentration that is at least 10 (e.g., 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, or more than 80) % greater than the control concentration indicates that a desired immunomodulatory effect has occurred in the human administered the anti-CD200 antibody. In some embodiments, determining whether an anti-CD200 antibody (e.g., a variant anti-CD200 antibody having reduced or no effector function) has produced a desired immunomodulatory effect in a human can be performed by querying whether the post-treatment activated T cell concentration falls within a predetermined range indicative of the occurrence of a desired immunomodulatory effect by an anti-CD200 antibody in a human or if the post-treatment activated T cell concentration for a given histological type of activated T cell falls above or below a predetermined cut-off value.

As described above, a comparison of the percent activated T cells to percent regulatory T cells can also be used to determine whether a desired immunomodulatory effect has occurred in a human administered an anti-CD200 antibody. For example, a practitioner can determine the ratio of the percent activated T cells to percent regulatory T cells in a biological sample obtained from a human administered an anti-CD200 antibody, wherein a ratio of at least 2:1 (e.g., at least 3:1, at least 4:1, at least 5:1, at least 6:1, or at least 7:1 or more) indicates that a desired immunomodulatory effect has occurred in the patient. In some embodiments, an increase in the ratio of the percent activated T cells to percent regulatory T cells in a biological sample obtained from a patient after administration of the anti-CD200 antibody, relative to the corresponding ratio determined in a biological sample obtained from the patient prior to administration of the antibody, indicates that the anti-CD200 antibody has produced a desired immunomodulatory effect in the human.

In some embodiments, the methods are performed using a computer. For example, the method can include receiving data including a medical profile of a human by way of, e.g., an internet communication or directly inputting the information into the computer. The profile contains information on at least one of: (a): (i) the concentration of $CD200^+$ T cells in a biological sample obtained from a human following administration to the human of an anti-CD200 antibody and (ii) the concentration of $CD200^+$ T cells of the same histological type as in (i) in a biological sample obtained from the human prior to administration of the antibody; (b): (iii) the concentration of $CD200R^+$ T cells in a biological sample obtained from a human following administration to the human of an anti-CD200 antibody and (iv) the concentration of $CD200R^+$ T cells of the same histological type as in (iii) in a biological sample obtained from the human prior to administration of the antibody; (c): (v) the level of expression of CD200R by a plurality of leukocytes in a biological sample obtained from the human following administration to the human of an anti-CD200 antibody and (vi) the level of expression of CD200R by a plurality of leukocytes of the same histological type as in (v) in a biological sample obtained from the human prior to administration of the antibody; and (d): (vii) the level of expression of CD200 by a plurality of leukocytes in a biological sample obtained from the human following administration to the human of an anti-CD200 antibody and (viii) the level of expression of CD200 by a plurality of leukocytes of the same histological type as in (vii) in a biological sample obtained from the human prior to administration of the antibody. Next, the computer processes at least the portion of the data containing the information to determine whether the antibody has produced a desired immunomodulatory effect in the human.

Computer-based methods can also include providing information on at least one of: (a): (i) the concentration of $CD200^+$ T cells in a biological sample obtained from a human following administration to the human of an anti-CD200 antibody and (ii) the concentration of CD200+ T cells of the same histological type as in (i) in a biological sample obtained from the human prior to administration of the antibody; (b): (iii) the concentration of $CD200R^+$ T cells in a biological sample obtained from a human following administration to the human of an anti-CD200 antibody and (iv) the concentration of $CD200R^+$ T cells of the same histological type as in (iii) in a biological sample obtained from the human prior to administration of the antibody; (c): (v) the level of expression of CD200R by a plurality of leukocytes in a biological sample obtained from the human following administration to the human of an anti-CD200 antibody and (vi) the level of expression of CD200R by a plurality of leukocytes of the same histological type as in (v) in a biological sample obtained from the human prior to administration of the antibody; d): (vii) the level of expression of CD200 by a plurality of leukocytes in a biological sample obtained from the human following administration to the human of an anti-CD200 antibody and (viii) the level of expression of CD200 by a plurality of leukocytes of the same histological type as in (vii) in a biological sample obtained from the human prior to administration of the antibody; (e): (ix) the concentration of regulatory T cells in a biological sample from a human following administration to the human of an anti-CD200 antibody and (x) the concentration of regulatory T cells of the same histological type as in (ix) in a biological sample from the human prior to administration of the anti-CD200 antibody; (f): (xi) the concentration of activated T cells in a biological sample from a human following administration of an anti-CD200 antibody to the human and (xii) the concentration of activated T cells of the same histological type as in (xi) in a biological sample from the human prior to administration of the anti-CD200 antibody; (g): (xiii) the ratio of percent activated T cells to percent regulatory T cells in a biological sample from a human following administration of an anti-CD200 antibody and (xiv) the corresponding ratio of percent activated T cells to percent regulatory T cells (each of the same histological type as in (xiii)) in a biological sample from the human prior to administration of the anti-CD200 antibody; and (h): (xv) the concentration of $CD8^+$ lymphocytes (e.g., T cells) in a biological sample from a human following administration of an anti-CD200 antibody to the human and (xvi) the concentration of $CD8^+$ lymphocytes of the same histological type as in (xv) in a biological sample from the human prior to administration of the antibody. The information is input into a computer and a parameter is calculated, the parameter indicating whether the antibody has produced a desired immunomodulatory effect in the human using the computer and the input information. The method can also include outputting the parameter and/or recording the parameter or result on a computer-readable medium or a physical file such as a patient record or chart.

As detailed in the working examples, the inventors have also discovered that following administration of an anti-CD200 antibody to an animal afflicted with an autoimmune disease, the concentration of $CD200^+$ leukocytes (e.g., subsets of $CD200^+$ leukocytes) and $CD200^+$ bone marrow cells (e.g., subsets of $CD200^+$ bone marrow cells) is reduced in the animal as measured by a reduction in the concentration of such cells in spleen tissue. A marked reduction in the concentration of autoimmune disorder-associated autoantibodies was observed in animals treated with the anti-CD200 antibody and in which the immunomodulatory effect occurred. Thus, while not being bound by any particular theory or mechanism of action, the inventors believe that monitoring a patient treated with an anti-CD200 antibody for the occurrence of one or more of these biomarkers is useful for, among other things, determining whether the anti-CD200 antibody is capable of producing a biological effect in the human to whom the antibody is administered. Moreover, monitoring for changes in one or more of the biomarkers is also useful for identifying a dose—a threshold dose—of an anti-CD200 antibody, such as samalizumab, that by virtue of its immunomodulatory effect in the human is sufficient to achieve a clinically-meaningful effect in the disease (i.e., sufficient to treat a disease such as an autoimmune disease). Since a similar immunomodulatory effect on $CD200^+$ cell populations was observed in cancer patients treated with an anti-CD200 antibody, the inventors believe that the anti-CD200 antibody-induced immunomodulatory effects on $CD200^+$ leukocytes and $CD200^+$ bone marrow cells is very likely to occur in humans as well.

Thus, in accordance with the present disclosure, to determine whether an anti-CD200 antibody (e.g., a variant anti-CD200 antibody that has reduced or no effector function) has produced a desired immunomodulatory effect in a human (and thereby the human has been administered a dose of the antibody sufficient to affect the treatment of the patient via, among other things, its immunomodulatory activity), a practitioner can measure the concentration of $CD200^+$ leukocytes (e.g., one or more $CD200^+$ bone marrow cell subsets and/or $CD200^+$ splenocytes) in a biological sample (e.g., a blood sample or a spleen sample) from a human administered an anti-CD200 antibody. A reduction in the concentration of $CD200^+$ leukocytes in the sample as compared to the concentration of CD200+ leukocytes in a control sample indicates that the anti-CD200 antibody has produced a desired immunomodulatory effect in the human. Similarly, to determine whether an anti-CD200 antibody (e.g., a variant anti-CD200 antibody that has reduced or no effector function) has produced a desired immunomodulatory effect in a human, a practitioner can also measure the concentration of CD200+ bone marrow cells in a biological sample from a human administered an anti-CD200 antibody. A reduction in the concentration of $CD200^+$ bone marrow cells in the sample as compared to the concentration of $CD200^+$ bone marrow cells (of the same histological type) in a control sample indicates that the anti-CD200 antibody has produced a desired immunomodulatory effect in the human.

As described above, determining whether an anti-CD200 antibody (e.g., a variant anti-CD200 antibody with decreased or no effector function) has produced a desired immunomodulatory effect in a human can be performed by comparing the concentration of $CD200^+$ leukocytes (e.g., $CD200^+$ splenocytes or $CD200^+$ bone marrow cells) in a biological sample obtained from a patient following administration of the anti-CD200 antibody (the post-treatment $CD200^+$ leukocyte or $CD200^+$ bone marrow cell concentration) to the concentration of $CD200^+$ cells in a control sample. In some embodiments, control sample is obtained from the subject human prior to administering to the subject human the anti-CD200 antibody. In some embodiments, the control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered an anti-CD200 antibody (e.g., a control concentration of $CD200^+$ cells of the same histological type can be an average of the concentration of the cells in one or more control samples obtained from patients who have not been administered an anti-CD200 antibody).

In some embodiments, a post-treatment $CD200^+$ leukocyte or $CD200^+$ bone marrow cell concentration that is at least 5% less than the control concentration indicates that a desired immunomodulatory effect has occurred in the human administered the anti-CD200 antibody. In some embodiments, a post-treatment $CD200^+$ leukocyte or $CD200^+$ bone marrow cell concentration that is at least 10 (e.g., 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, or more than 80) % less than the control concentration indicates that a desired immunomodulatory effect has occurred in the human administered the anti-CD200 antibody.

In some embodiments, determining whether an anti-CD200 antibody (e.g., a variant anti-CD200 antibody having reduced or no effector function) has produced a desired immunomodulatory effect in a human can be performed by querying whether the post-treatment $CD200^+$ leukocyte or $CD200^+$ bone marrow cell concentration falls within a predetermined range indicative of the occurrence of a desired immunomodulatory effect by an anti-CD200 antibody in a human. In some embodiments, determining whether an anti-CD200 antibody has produced a desired immunomodulatory effect in a human can include querying if the post-treatment $CD200^+$ leukocyte or $CD200^+$ bone marrow cell concentration for a given histological type of $CD200^+$ leukocytes or $CD200^+$ bone marrow cells falls above or below a predetermined cut-off value. A cut-off value is typically the concentration of $CD200^+$ leukocytes or $CD200^+$ bone marrow cells of a given histological type above or below which is considered indicative of a certain phenotype—namely the occurrence of a desired immunomodulatory effect in a human produced by an anti-CD200 antibody.

Methods for Treatment

The disclosure also features methods for treating a variety of disorders including, e.g., cancers, inflammatory conditions, and disorders associated with bone loss (also referred to herein as a "bone disorder"). For example, after it is determined that an anti-CD200 antibody has produced a desired immunomodulatory effect in a human suffering from a cancer (e.g., using any of the diagnostic methods described herein), a medical practitioner may elect to administer to the human the anti-CD200 antibody in an amount and with a frequency sufficient to maintain the occurrence of the immunomodulatory effect to thereby treat the patient's cancer. Similarly, after it has been determined that an anti-CD200 antibody has produced a desired immunomodulatory effect in a human suffering from an inflammatory condition, a medical practitioner may elect to administer to the human the anti-CD200 antibody in an amount and with a frequency sufficient to maintain the immunomodulatory effect in the patient to thereby treat the patient's inflammatory condition. Methods for therapeutically administering an anti-CD200 antibody to a human are well known in the art and described in, e.g., U.S. Pat. No. 7,408,041.

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., neuroblastoma), melanoma, thyroid cancer, ovarian cancer, testicular cancer, prostate cancer, cervical cancer, vaginal cancer, or bladder cancer. Hematological cancers (liquid tumors) include, e.g., leukemias (e.g., chronic lymphocytic leukemia such as B cell or T cell type chronic lymphocytic leukemia) and multiple myeloma. Bone cancers include, without limitation, osteosarcoma and osteocarcinomas.

As used herein, a human "at risk of developing a cancer" is a human that has a predisposition to develop a cancer, i.e., a genetic predisposition to develop cancer such as a mutation in a tumor suppressor gene (e.g., mutation in BRCA1, p53, RB, or APC) or has been exposed to conditions that can result in cancer. Thus, a human can also be one "at risk of developing a cancer" when the human has been exposed to mutagenic or carcinogenic levels of certain compounds (e.g., carcinogenic compounds in cigarette smoke such as acrolein, arsenic, benzene, benz{a}anthracene, benzo{a}pyrene, polonium-210 (radon), urethane, or vinyl chloride). Moreover, the human can be "at risk of developing a cancer" when the human has been exposed to, e.g., large doses of ultraviolet light or X-irradiation, or infected by a tumor-causing/associated virus such as a papillomavirus, Epstein-Barr virus, hepatitis B virus, or human T-cell leukemia-lymphoma virus. From the above it will be clear that humans "at risk of developing a cancer" are not all the humans within a species of interest.

A human "suspected of having a cancer" is one having one or more symptoms of a cancer. Symptoms of cancer are well-known to those of skill in the art and include, without limitation, breast lumps, pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, and difficulty swallowing. Symptoms of a primary cancer (e.g., a large primary cancer) can include, e.g., any one of colon metastases, lung metastases, bladder metastases, liver metastases, bone metastases, kidney metastases, and pancreas metastases.

An anti-CD200 antibody or an antigen-binding fragment thereof described herein can be co-administered to a human with cancer along with one or more additional therapeutic anti-cancer agents. Anti-cancer agents include, e.g., chemotherapeutic agents, ionizing radiation, immunotherapy agents, or hyperthermotherapy agents. Chemotherapeutic agents include, but are not limited to, aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, taxol, temozolomide, teniposide, testosterone, thioguanine, thiotepa, titanocene dichloride, topotecan, trastuzumab, tretinoin, vinblastine, vincristine, vindesine, and vinorelbine. In some embodiments, a pharmaceutical composition comprising an anti-CD200 antibody or CD200-binding fragment thereof can be co-formulated with one or more of any of the foregoing agents or any other anti-cancer agent described herein.

These chemotherapeutic anti-tumor compounds may be categorized by their mechanism of action into groups, including, for example, the following: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF)-inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

As described above, in some embodiments of the methods described herein (e.g., in some embodiments of the methods for treating cancer), the anti-CD200 antibody is not administered to the human in combination with a chemotherapeutic compound or any other compound that has or may have an immunosuppressive effect in the human. That is, in some embodiments, a patient is selected for treatment with a therapeutic anti-CD200 antibody if the patient has not already been administered (within a specified period of time prior to starting the anti-CD200 antibody therapy) a chemotherapeutic agent (such as any of those described herein) or any other agent that can (or did) result in an immunosuppression in the patient. In some embodiments, the human is one who has not received a chemotherapeutic treatment prior to administration of the first dose of the anti-CD200 antibody and/or continues to not receive a chemotherapeutic treatment as long as the patient is being administered the anti-CD200 antibody. "Prior to administration of the first dose of the anti-CD200 antibody" can include, e.g., within a time-period that is less than four months (e.g., less than 16 weeks, 15 weeks, 14 weeks, 13 weeks, three months, 12 weeks, 11 weeks, 10 weeks, 9 weeks, two months, eight weeks, seven weeks, six weeks, five weeks, one month, 30, 29, 28, 27, 26, 25, 24, 23, 22, 21, 20, 19, 18, 17, 16, 15, 14, 13, 12, 11, or less than 10 days) prior to administration of the first dose of the anti-CD200 antibody.

In some embodiments, the methods described herein can include determining whether the human has a cancer. In some embodiments, the methods described herein can include the step of determining whether one or more cancer cells of a human's cancer express CD200. In some embodiments, the methods can include determining whether one or more cancer cells of the human's cancer overexpress CD200, relative to a control sample. In some embodiments, the control sample is obtained from the same human and comprises normal cells of the same tissue type as the human's cancer. For example, a skilled artisan could measure the level of CD200 protein present on colon cancer cells from a patient as compared to normal colon cells from the patient. In some embodiments, the control sample can be the expression level (or average expression level) of cells obtained from one or more humans who do not have cancer. In some embodiments, the cancer comprises cells (e.g., a plurality or even a majority of cells) that express or overexpress CD200 (e.g., CD200 protein and/or CD200 mRNA). In some embodiments, at least (or greater than) 10 (e.g., 15, 20, 25, 30, 35, 40, 45, 50, 55, 60, 65, 70, 75, 80, 85, 90, or 95) % of the cancer cells of the human's cancer overexpress CD200. In some embodiments, all assayed cancer cells overexpress CD200 relative to normal cells. In some embodiments, a cancer cell (e.g., a plurality of cancer cells, at least 10% of cancer cells, or all assayed cancer cells) can express CD200 protein at levels at least about 1.4 (e.g., at least about 1.5, 1.6, 1.7, 1.8, 1.9, 2.0, 2.2, 2.5, 3.0, 3.5, 4.0, 4.5, or 5 or more)-fold higher than the expression levels found on normal cells of the same histological type or higher than the average expression of normal cells from one or more patients who do not have cancer.

In some embodiments, an anti-CD200 antibody is only administered to a human if the human's cancer comprises a plurality of cancer cells that express or overexpress CD200. Methods for detecting expression of CD200 are well known in the art and include, e.g., Western blot, immunohistochemistry, and flow cytometry techniques. Suitable methods for detecting CD200 expression are described in detail in, e.g., Kretz-Rommel et al. (2007) *J Immunol* 178:5595-5605 and Kretz-Rommel et al. (2008) *J Immunol* 180:699-705.

In some embodiments, an anti-CD200 antibody blocks immune suppression in cancer by targeting cancer cells that express CD200. Eradication, or inhibition, of these cancer cells can stimulate the immune system and allow further eradication of cancer cells.

In some embodiments, the combination of direct cancer cell killing and driving the immune response towards a Th1 profile provides enhanced efficacy in cancer treatment. Thus, in one embodiment, a cancer treatment is provided wherein an antibody or antibody fragment, which binds to CD200 and both a) blocks the interaction between CD200 and its receptor and b) directly kills the cancer cells expressing CD200, is administered to a cancer patient. The mechanism by which the cancer cells are killed can include, but are not limited to, ADCC or CDC; fusion with a toxin; fusion with a toxic radioactive agent; fusion with a toxic polypeptide such as granzyme B or perforin; fusion with a cytotoxic virus (e.g., cytotoxic reovirus such as Reolysin®); or fusion with a cytokine such as TNF-α or IFN-α. In an alternative embodiment, a cancer treatment involves administering an antibody that both a) blocks the interaction between CD200 and its receptor and b) enhances cytotoxic T cell or NK cell activity against the tumor. Such enhancement of the cytotoxic T cell or NK cell activity may, for example, be combined by fusing the antibody with cytokines such as, e.g., IL-2, IL-12, IL-18, IL-13, and IL-5. In addition, such enhancement may be achieved by administration of an anti-CD200 antibody in combination with inhibitors such as IMiDs, thalidomide, or thalidomide analogs.

In yet another embodiment, the cancer treatment involves administering an antibody that both a) blocks the interaction between CD200 and its receptor and b) attracts T cells to the tumor cells. T cell attraction can be achieved by fusing the Ab with chemokines such as MIG, IP-10, 1-TAC, CCL21, CCL5 or LIGHT. Also, treatment with chemotherapeutics can result in the desired upregulation of LIGHT. The combined action of blocking immune suppression and killing directly through antibody targeting of the tumor cells is a unique approach that provides increased efficacy.

An "inflammatory condition," as used herein, refers to a process in which one or more substances (e.g., substances not naturally occurring in the human), via the action of white blood cells (e.g., B cells, T cells, macrophages, monocytes, or dendritic cells) inappropriately trigger a pathological response, e.g., a pathological immune response. Accordingly, such immune cells involved in the inflammatory response are referred to as "inflammatory cells." The inappropriately triggered inflammatory response can be one where no foreign substance (e.g., an antigen, a virus, a bacterium, a fungus) is present in or on the human. The inappropriately triggered response can be one where a self-component (e.g., a self-antigen) is targeted (e.g., an autoimmune disorder such as multiple sclerosis) by the inflammatory cells. The inappropriately triggered response can also be a response that is inappropriate in magnitude or duration, e.g., anaphylaxis. Thus, the inappropriately targeted response can be due to the presence of a microbial infection (e.g., viral, bacterial, or fungal). Types of inflammatory condition (e.g., autoimmune disease) can include, but are not limited to, osteoarthritis; rheumatoid arthritis; spondyloarthropathies; respiratory distress syndrome (including adult respiratory distress syndrome; ARDS), POEMS syndrome; inflammatory bowel disease; Crohn's disease, graft-versus host disease (e.g., rejections of skin grafts, kidney grafts, heart grafts, lung grafts, liver grafts, or bone marrow grafts); multicentric Castleman's disease; systemic lupus erythematosus (SLE); multiple sclerosis; muscular dystrophy; insulin-dependent diabetes mellitus; dermatomyositis; polymyositis; inflammatory neuropathies such as Guillain Barré syndrome; vasculitis such as Wegener's granulomatosus; lupus nephritis (LN); glomerulonephritis; polyarteritis nodosa; polymyalgia rheumatica; temporal arteritis; Sjögren's syndrome; Behçet's disease; Churg-Strauss syndrome; or Takayasu's arteritis. Also included in inflammatory disorders are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory conditions can also include ulcerative colitis and asthma.

A human "at risk of developing an inflammatory condition" refers to a human with a family history of one or more inflammatory conditions (e.g., a genetic predisposition to one or more inflammatory disorders) or one exposed to one or more inflammation-inducing conditions. For example, a human can have been exposed to a viral or bacterial superantigen such as, but not limited to, Staphylococcal enterotoxins (SEs), a Streptococcus pyogenes exotoxin (SPE), a Staphylococcus aureus toxic shock-syndrome toxin (TSST-I), a Streptococcal mitogenic exotoxin (SME) and a Streptococcal superantigen (SSA). From the above it will be clear that humans "at risk of developing an inflammatory condition" are not all the humans within a species of interest.

A human "suspected of having an inflammatory condition" is one who presents with one or more symptoms of an inflammatory condition. Symptoms of inflammatory disorders are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain. From the above it will be clear that humans "suspected of having an inflammatory condition" are not all the humans within a species of interest.

An "autoimmune disorder," as used herein, refers to a disease state in which, via the action of white blood cells (e.g., B cells, T cells, macrophages, monocytes, or dendritic cells), a pathological immune response (e.g., pathological in duration and/or magnitude) has been generated in a host organism against a substance or a tissue that is normally present within the host organism. Types of autoimmune diseases include, but are not limited to, chronic obstructive pulmonary disease, diabetes mellitus type 1, Goodpasture's syndrome, SLE, LN, Grave's disease, Guillain-Barré syndrome, IgA nephropathy, scleroderma, Sjögren's syndrome, Wegener's granulomatosis, pemphigus vulgaris, Chagas disease, rheumatoid arthritis, Crohn's disease, Hashimoto's disease, idiopathic thrombocytopenic purpura, myasthenia gravis, pulmonary biliary cirrhosis, and Miller Fisher syndrome. Autoimmune disorders also include certain autoimmune hemolytic disorders such as cold agglutinin disease (CAD), antiphospholipid syndrome (APS), autoimmune hemolytic disease (e.g., autoimmune hemolytic anemia; AIHA), catastrophic anti-phospholipid syndrome (CAPS), warm autoimmune hemolytic anemia, and paroxysmal cold hemoglobinuria (PCH).

A human "at risk of developing autoimmune disorder" refers to a human with a family history of autoimmune disorders (e.g., a genetic predisposition to one or more autoimmune disorders) or one exposed to one or more autoimmune disorder/autoantibody-inducing conditions. Humans with certain cancers (e.g., liquid tumors such as multiple myeloma or chronic lymphocytic leukemia) can pre-dispose patients to developing certain autoimmune hemolytic diseases. For example, PCH can follow a variety of infections (e.g., syphilis) or neoplasms such as non-Hodgkin's lymphoma. In another example, CAD can be associated with HIV infection, Mycoplasma pneumonia infection, non-Hodgkin's lymphoma, or Waldenstrom's macroglobulinemia. In yet another example, autoimmune hemolytic anemia is a well-known complication of human chronic lymphocytic leukemia, approximately 11% of CLL patients with advanced disease will develop AIHA. As many as 30% of CLL patients may be at risk for developing AIHA. See, e.g., Diehl et al. (1998) Semin Oncol 25(1):80-97 and Gupta et al. (2002) Leukemia 16(10):2092-2095. From the above it will be clear that humans "at risk of developing an autoimmune disorder" are not all the humans within a species of interest.

A human "suspected of having an autoimmune disorder" is one who presents with one or more symptoms of an autoimmune disorder. Symptoms of autoimmune disorders can vary in severity and type with the particular autoimmune disorder and include, but are not limited to, redness, swelling (e.g., swollen joints), joints that are warm to the touch, joint pain, stiffness, loss of joint function, fever, chills, fatigue, loss of energy, pain, fever, pallor, icterus, urticarial dermal eruption, hemoglobinuria, hemoglobinemia, and anemia (e.g., severe anemia), headaches, loss of appetite, muscle stiffness, insomnia, itchiness, stuffy nose, sneezing, coughing, one or more neurologic symptoms such as dizziness, seizures, or pain. From the above it will be clear that humans "suspected of having an autoimmune disorder" are not all the humans within a species of interest.

An anti-CD200 antibody described herein can be co-administered with one or more additional therapeutic agents useful for treating or preventing an inflammatory condition. The one or more agents include, e.g., a non-steroidal anti-inflammatory drug (NSAID), a disease-modifying anti-rheumatic drug (DMARD), a biological response modifier, or a corticosteroid. Biological response modifiers include, e.g., an anti-TNF agent (e.g., a soluble TNF receptor or an antibody specific for TNF such as adulimumab, infliximab, or etanercept). In some embodiments, the one or more additional therapeutic agents can be, e.g., steroids, anti-malarials, aspirin, non-steroidal anti-inflammatory drugs, immunosuppressants, cytotoxic drugs, corticosteroids (e.g., prednisone, dexamethasone, and prednisolone), methotrexate, methylprednisolone, macrolide immunosuppressants (e.g., sirolimus and tacrolimus), mitotic inhibitors (e.g., azathioprine, cyclophosphamide, and methotrexate), fungal metabolites that inhibit the activity of T lymphocytes (e.g., cyclosporine), mycophenolate mofetil, glatiramer acetate, and cytotoxic and DNA-damaging agents (e.g., chlorambucil or any other DNA-damaging agent described herein or known in the art).

The anti-CD200 antibodies described herein can also be used to treat a variety of disorders associated with bone loss including, e.g., osteoporosis and periodontal disease. Bone loss can result from a number of disorders such as, but not limited to, hypercalciuria, nutritional disorders (e.g., eating disorders such as bulimia or anorexia), menopause, premature ovarian failure, hypogonadal conditions such as Turner syndrome, Klinefelter syndrome, Kallmann syndrome, andropause, hypothalamic amenorrhea, or hyperprolactinemia. Osteoporotic bone loss can also result from a number of cancers and inflammatory disorders. For example, bone loss can result from multiple myeloma (MM), rheumatoid arthritis (RA), and systemic lupus erythematosus (SLE). A human "at risk for developing a disorder associated with bone loss" is one with a family history of osteoporosis or a human having a disorder that is associated with osteoporosis. For example, a human at risk for developing osteoporosis can be one who has multiple myeloma, a nutritional disorder, or an osteoporosis-associated inflammatory disorder such as RA or SLE. A human at risk for developing osteoporosis can be, e.g., a menopausal woman. From the above it will be clear that humans "at risk of developing a disorder associated with bone loss" are not all the humans within a species of interest.

A human "suspected of having a disorder associated with bone loss" is one who presents with one or more symptoms of the disorder. Symptoms of osteoporosis include, e.g., fragility fractures, pain (e.g., neck pain or lower back), and stooped posture resulting from spinal compression fractures.

In addition to the administration of one or more anti-CD200 antibodies, or CD200-binding fragments thereof, described herein, a disorder associated with bone loss can be treated with a bisphosphonate, recombinant parathyroid hormone, hormone replacement therapy (e.g., estrogen therapy in women), and a selective estrogen receptor modulator.

CD200 has been shown in animal models to play a role in pregnancy. For example, increased CD200 expression, by way of a soluble CD200-Fc fusion protein, has been shown to decrease the rate of spontaneous abortion in mice. (See, e.g., Clark et al. (2001) *Mol Human Reprod* 7:185-194 and Gorczynski et al. (2001) *Graft* 4:338-345). Thus, prior to administering an anti-CD200 antibody or CD200-binding fragment thereof to a woman, a medical practitioner can determine if the woman is pregnant. If the woman is pregnant, the medical practitioner may opt not to administer the anti-CD200 antibody to the woman. The medical practitioner can optionally select an alternative therapy for the woman.

In some embodiments, the therapeutic efficacy of myeloablative therapies followed by bone marrow transplantation, or adoptive transfer of T cells reactive with CLL cells, is enhanced by anti-CD200 therapy. Furthermore, anti-CD200 treatment can substantially enhance efficacy of cancer vaccines such as dendritic cells loaded with CLL cell proteins, peptides or RNA derived from such cells, patient-derived heat-shock proteins (HSPs), tumor peptides or protein. In other embodiments, an anti-CD200 antibody or CD200-binding fragment thereof can be used in combination with an immuno-stimulatory compound, such as CpG, toll-like receptor agonists or any other adjuvant, anti-CTLA-4 antibodies, and the like. In some embodiments, efficacy of anti-CD200 antibody (or CD200-binding fragment) treatment can be improved by blocking of immunosuppressive mechanisms using anti-PDL1 and/or anti-PDL2 antibodies, anti-IL-10 antibodies, anti-IL-6 antibodies, and the like. In some embodiments, the efficacy of an anti-CD200 antibody treatment is improved by administration of agents that increase NK cell number or T-cell activity such as the small molecule inhibitor IMiDs, thalidomide, or thalidomide analogs.

In some embodiments, it can be advantageous to eliminate plasmacytoid dendritic cells, shown to be immunosuppressive in the cancer environment. In these embodiments in which delivery of an anti-CD200 antibody or CD200-binding fragment thereof is intended to augment an immune response, an anti-CD200 antibody lacking effector function is advantageous.

In some embodiments, the methods described herein can include, after administering the anti-CD200 antibody, monitoring the human for an improvement in the disorder and/or one or more symptoms thereof. Monitoring a human for an improvement in a disorder (e.g., a cancer, an inflammatory condition, or a disorder associated with bone loss), as defined herein, means evaluating the subject for a change in a disease parameter, e.g., an improvement in one or more symptoms of the disease. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The human can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a disorder described herein.

In some embodiments, monitoring the progress and/or effectiveness of a therapeutic treatment includes monitoring the level of CD200 expression before and after treatment. For example, pre-treatment levels of CD200 can be ascertained and, after at least one administration of the therapy, levels of CD200 can again be determined. A decrease in CD200 levels can be indicative of an effective treatment (see below). Measurement of CD200 levels can be used by the practitioner as a guide for increasing dosage amount or frequency of the therapy. It should of course be understood that CD200 levels can be directly monitored or, alternatively, any marker that correlates with CD200 can be monitored.

The inventors have also discovered that upon administration of an anti-CD200 antibody to a patient with a cancer comprising cells expressing CD200, CD200 expression by the cancer cells is reduced. As noted above, cancer cells have evolved a number of ways to evade detection by the immune system, which can identify malignant cells within a host organism and kill the cells before a cancer develops. See, e.g., Geertsen et al. (1999) *Int J Mol Med* 3(1):49-57; Kerebijn et al. (1999) *Crit. Rev Oncol Hematol* 31(1):31-53; and Pardoll (2003) *Annu Rev Immunol* 21:807-39. One potential mechanism by which cancer cells escape immunosurveillance is expression or overexpression of the immunosuppressive CD200 protein. In fact, CD200 protein has been shown to be expressed or overexpressed on a variety of human cancer cells including, e.g., B cell chronic lymphocytic leukemia cells, prostate cancer cells, breast cancer cells, colon cancer cells, and brain cancer cells. See, e.g., Kawasaki et al. (2007) *Biochem Biophys Res Commun* 364(4):778-782; Kretz-Rommel et al. (2007), supra; and Siva et al. (2008) *Cancer Immunol Immunother* 57(7):987-96. Thus, while the disclosure is not bound by any particular theory or mechanism of action, the inventors believe that the anti-CD200 antibody-dependent downregulation of CD200 on the cancer cells relieves an inhibition of immunosurveillance and allows the immune system to more effectively identify and fight the cancer.

Accordingly, it is believed to be beneficial to administer to the human an anti-CD200 antibody in an amount and with a frequency sufficient to sustain the reduced expression of CD200 by the cancer cells in the human. Methods for detecting expression or a change in expression of CD200 by cancer cells are well known in the art (e.g., Western blot, immunohistochemistry, and flow cytometry techniques) and described herein. For example, following the administration of an anti-CD200 antibody to a human, the level of expression of CD200 by cancer cells can be determined by flow cytometry analysis of the cancer cells present in a biological sample obtained from a patient. The CD200 expression level of the cancer cells post-treatment can be compared to a control expression level and/or the level of expression of the patient's cancer cells prior to treatment with the antibody, wherein a reduction in the level of CD200 expression by the cancer cells indicates that the anti-CD200 antibody has been administered to the human in an amount and with a frequency sufficient to reduce CD200 expression by the cancer cells.

Through an iterative process, a medical practitioner can determine the appropriate dose amount, and frequency of administration of each dose, required to maintain a reduced level of CD200 expression by the cancer cells in the patient. For example, a medical practitioner can administer to a cancer patient at least two (e.g., at least three, four, five, six, seven, or eight or more) times an anti-CD200 antibody in an amount that reduces (or is at least expected to reduce) the level of expression of CD200 by the cancer cells. The at least two doses should be spaced apart in time by at least one (e.g., at least two, three, four, five, six, seven, eight, nine, 10, 11, 12, 13, or even 14) day(s). Biological samples (e.g., blood samples) containing cancer cells are obtained from the patient at various times, e.g., prior to the first anti-CD200 antibody administration, between the first dose and at least one additional dose, and at least one biological sample collection following the second dose. In some embodiments, biological samples may be collected at least two times between doses and/or at least one time after the final dose administered to the patient. The cancer cells in each biological sample obtained are then interrogated for CD200 expression to determine whether the amount and/or the frequency of administration of the anti-CD200 antibody are sufficient to maintain a reduced level of CD200 expression by the cancer cells. Armed with information on CD200 expression by the patient's cancer cells over time and the effect on CD200 expression by the cells over time by administering the anti-CD200 antibody to the patient, a medical practitioner (and/or a computer) can determine an anti-CD200 antibody dosing schedule for the patient that is sufficient to maintain a reduced level of CD200 expression by the patient's cancer cells over the course of the treatment.

As described above, the inventors have also observed that upon administration of an anti-CD200 antibody to a patient with a cancer comprising cells expressing CD200: (i) the level of expression of CD200 by leukocytes is reduced as compared to the expression level of CD200 by leukocytes of the same histological type in a control sample; (ii) the level of expression of CD200R by leukocytes is increased as compared to the expression level of CD200R by leukocytes of the same histological type in a control sample; (iii) the concentration of $CD200^+$ T cells, as compared to the concentration of $CD200^+$ T cells of the same histological type in a control sample, is reduced; and (iv) the concentration of $CD200R^+$ leukocytes, as compared to the concentration of $CD200R^+$ leukocytes of the same histological type in a control sample, is increased. Similarly, the inventors have also observed that upon administration of an anti-CD200 antibody to an animal with an autoimmune disease the concentration of $CD200^+$ leukocytes and $CD200^+$ bone marrow cells is reduced as compared to the concentration of such cells in an animal not treated with the antibody. Accordingly, the disclosure also features methods for determining the appropriate dose amount, and frequency of administration of each dose, required to maintain, e.g., a reduced level of CD200 expression by leukocytes in the patient; an increased level of CD200R expression by leukocytes in the patient; a reduced concentration of $CD200^+$ leukocytes and/or $CD200^+$ bone marrow cells in the patient; and/or an increased concentration of $CD200R^+$ leukocytes in the patient, for the duration of the treatment of the patient with an anti-CD200 antibody.

Using the information provided herein on the immunomodulatory effect(s) of an anti-CD200 antibody (e.g., the reduction in the expression level of CD200 by cancer cells or the increase in CD200R expression by leukocytes in a patient treated with an anti-CD200 antibody), it would be a matter of routine experimentation for a skilled artisan in the field of medicine to determine an appropriate dosing schedule of an anti-CD200 antibody for a patient that maintains in the patient the presence of at least one of the immunomodulatory effects disclosed herein.

For example, an antibody described herein can be administered as a fixed dose, or in a milligram per kilogram (mg/kg) dose. In some embodiments, the dose can also be chosen to reduce or avoid production of antibodies or other host immune responses against one or more of the active antibodies in the composition. While in no way intended to be limiting, exemplary dosages of an antibody include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of an antibody described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg. Exemplary doses (e.g., of a whole anti-CD200 antibody such as samalizumab) also include, e.g., greater than or equal to 50 mg/m$^2$, 75 mg/m$^2$, 100 mg/m$^2$, 150 mg/m$^2$, 200 mg/m$^2$, 250 mg/m$^2$, 300 mg/m$^2$, 350 mg/m$^2$, 400 mg/m$^2$, 450 mg/m$^2$, 500 mg/m$^2$, 550 mg/m$^2$, 600 mg/m$^2$, and/or 700 mg/m$^2$.

A pharmaceutical composition can include a therapeutically effective amount of an antibody described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody described herein can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of the cancer and/or the presence of at least one of the immunomodulatory effect biomarkers described herein. A therapeutically effective amount is also one in which any toxic or detrimental effects of the composition are outweighed by the therapeutically beneficial effects.

Toxicity and therapeutic efficacy of such compositions can be determined by known pharmaceutical procedures in cell cultures or experimental animals (e.g., animal models of any of the disorders described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An anti-CD200 antibody that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The inventors have also discovered an inverse correlation between the peripheral tumor load (e.g., B CLL tumor cell load) and the concentration (or number) of T cells present in cancer patients. That is, the greater the concentration of non-cancer T cells present in a cancer patient, the lower the tumor burden in the patient. While the discovery is not by any particular theory or mechanism of action, the inventors believe that a cancer patient may receive an enhanced benefit from an anti-CD200 antibody therapy if the cancer patient exhibits normal or elevated levels of T cells at the time of therapy. Similarly, the inventors have also determined that an anti-CD200 antibody therapy is likely to have even more efficacy and/or a stronger immunomodulatory effect in patients with an intact immune system, e.g., an immune system that is capable of mounting an immune response against a cancer present in the patient. To wit, as described below, all four of the cancer patients in the study who had not received prior chemotherapy before samalizumab treatment had clinically stable or improved disease after samalizumab treatment. In fact, patient 102-502, who had not received an immunosuppressive or chemotherapeutic therapy prior to administration of the anti-CD200 antibody, exhibited a substantial reduction in tumor burden, which correlated with changes in a number of the immunomodulatory biomarkers described herein, including, a marked reduction in the concentration of $CD45^+$ B CLL cells, an increase in $CD8^+$ T cells, a decrease in regulatory T cells, an increase in activated T cells, and an increase in the ratio of percent activated T cells to percent regulatory T cells.

Accordingly, a cancer patient who has an intact immune system capable of mounting an immune response to the patient's cancer can be selected for treatment with an anti-CD200 antibody. Selection can include, e.g., quantifying the concentration of $CD3^+$ cells present in a biological sample from a patient suffering from a cancer; and administering to the patient the anti-CD200 antibody in an amount effective to treat the cancer in the patient if the patient has a concentration of T cells sufficient to enhance the efficacy of the anti-CD200 antibody therapy in the patient. The average concentration of $CD3^+$ cells in blood from a healthy human and a human having a cancer such as B-CLL are well known in the art. In some embodiments, a sufficient concentration of $CD3^+$ cells in the biological sample is a concentration of $CD3^+$ cells that is greater than 300 (e.g., 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, or 1300 or more) cells per microliter. In some embodiments, a sufficient concentration of $CD3^+$ cells in the biological sample is a concentration of $CD3^+/CD4^+$ cells that is greater than or equal to 200 (e.g., 225, 250, 275, 300, 325, 350, 375, 400, 425, 450, 475, or 500 or more) cells per microliter. In some embodiments, a sufficient concentration of $CD3^+$ cells in the biological sample is a concentration of $CD3^+/CD8^+$ cells that is greater than or equal to 150 (e.g., 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, or 1300 or more) cells per microliter. Methods for determining the concentration of $CD3^+$ cells are known in the art and include, e.g., flow cytometry. Methods for administering an anti-CD200 antibody therapeutically to a cancer patient are known in the art, described herein, and elaborated on in, e.g., U.S. Pat. No. 7,408,041.

In some embodiments, immune competence can be determined by quantifying the absolute number of certain lymphocyte populations in a biological sample (e.g., a blood sample) obtained from a patient as measured by, e.g., flow cytometry. See, e.g., Shearer et al. (2003) *J Allergy Clin Immunol* 112 (5):973-980 and Paglieroni and Holland (1994) *Transfusion* 34:512-516. For example, in some embodiments, immune competence is indicated by a $CD45^+$ lymphocyte count, by flow cytometry, of: $0.66$-$4.60\times10^3$ cells/µL (for patients 0 to 17 years of age); $0.99$-$3.15\times10^3$ cells/µL (for patients aged 18 to 55 years); or $1.00$-$3.33\times10^3$ cells/µL (for patients older than 55 years).

In some embodiments, immune competence can be determined by quantifying the absolute number of $CD3^+$ T cells, by flow cytometry, in a biological sample obtained from a patient. For example, in some embodiments, immune competence is indicated by a $CD3^+$ lymphocyte count, by, e.g., flow cytometry, of: 2,500-5,500 cells/µL (for patients 0 to 2 months of age); 2,500-5,600 cells/µL (for patients aged 3 to 5 months); 1,900-5,900 cells/µL (for patients aged 6 to 11 months); 2,100-6,200 cells/µL (for patients aged 12 to 23 months); 1,400-3,700 cells/µL (for patients aged 2 to 5 years); 1,200-2,600 cells/µL (for patients aged 6 to 11 years); 1,000-2,200 cells/µL (for patients aged 12 to 17 years); 677-2,383 cells/µL (for patients aged 18 to 55 years); or 617-2,254 cells/µL (for patients older than 55 years of age).

In some embodiments, immune competence can be determined by quantifying the absolute number of $CD19^+$ B cells, by, e.g., flow cytometry, in a biological sample obtained from a patient. For example, in some embodiments, immune competence is indicated by a $CD19^+$ B cell count, by flow cytometry, of: 300-2,000 cells/µL (for patients 0 to 2 months of age); 430-3,000 cells/µL (for patients aged 3 to 5 months); 610-2,600 cells/µL (for patients aged 6 to 11 months); 720-2,600 cells/µL (for patients aged 12 to 23 months); 390-1,400 cells/µL (for patients aged 2 to 5 years); 270-860 cells/µL (for patients aged 6 to 11 years); 110-570 cells/µL (for patients aged 12 to 17 years); 99-527 cells/pt (for patients aged 18 to 55 years); or 31-409 cells/µL (for patients older than 55 years of age).

In some embodiments, immune competence can be determined by quantifying the absolute number of $CD16^+CD56^+$ Natural Killer (NK) cells, by, e.g., flow cytometry, in a biological sample obtained from a patient. For example, in some embodiments, immune competence is indicated by a $CD16^+CD56^+$ NK cell count, by flow cytometry, of: 170-1,100 (for patients 0 to 2 months of age); 170-830 cells/µL (for patients aged 3 to 5 months); 160-950 cells/µL (for patients aged 6 to 11 months); 180-920 cells/µL (for patients aged 12 to 23 months); 130-720 cells/µL (for patients aged 2 to 5 years); 100-480 cells/µL (for patients aged 6 to 11 years); 110-570 cells/µL (for patients aged 12 to 17 years); 101-678 cells/µL (for patients aged 18 to 55 years); or 110-657 cells/µL (for patients older than 55 years of age).

In some embodiments, immune competence can be determined by quantifying the absolute number of $CD4^+$ Helper T cells, by, e.g., flow cytometry, in a biological sample obtained from a patient. For example, in some embodiments, immune competence is indicated by a $CD4^+$ Helper T cell count, by flow cytometry, of: 1,600-4,000 (for patients 0 to 2 months of age); 1,800-4,000 cells/µL (for patients aged 3 to months); 1,400-4,300 cells/µL (for patients aged 6 to 11 months); 1,300-3,400 cells/µL (for patients aged 12 to 23 months); 700-2,200 cells/µL (for patients aged 2 to 5 years); 650-1,500 cells/µL (for patients aged 6 to 11 years); 530-1,300 cells/µL (for patients aged 12 to 17 years); 424-1,509 cells/µL (for patients aged 18 to 55 years); or 430-1,513 cells/µL (for patients older than 55 years of age).

In some embodiments, immune competence can be determined by quantifying the absolute number of $CD8^+$ T cells, by, e.g., flow cytometry, in a biological sample obtained from a patient. For example, in some embodiments, immune competence is indicated by a $CD8^+$ T cell count, by flow cytometry, of: 560-1,700 (for patients 0 to 2 months of age); 590-1,600 cells/µL (for patients aged 3 to 5 months); 500-1,700 cells/µL (for patients aged 6 to 11 months); 620-2,000 cells/µL (for patients aged 12 to 23 months); 490-1,300 cells/µL (for patients aged 2 to 5 years); 370-1,100 cells/µL (for patients aged 6 to 11 years); 330-920 cells/µL (for patients aged 12 to 17 years); 169-955 cells/µL (for patients aged 18 to 55 years); or 101-839 cells/µL (for patients older than 55 years of age).

It is understood that immune cell counts that fall below these levels, as measured in a biological sample obtained from a patient, may indicate that the patient is immunocompromised. Immune cell counts that fall within one or more of the ranges set forth above may indicate that the patient is immunocompetent and likely to receive an enhanced benefit from an anti-CD200 antibody therapy described herein. Any of the methods described herein can include assaying a biological sample to determine: (a) the number per microliter of one or more of the immune cell subsets described herein and/or (b) whether the assayed numbers fall within a pre-determined range such as the pre-determined ranges described above.

In some embodiments, the methods described herein can include identifying or selecting a subject that has an intact immune system, e.g., one competent to mount an immune response against the cancer present in or on the subject. Methods for determining whether an immune system is competent to mount an immune response against a cancer are well known in the art. For example, a medical practitioner may assay for antibody (e.g., IgG, IgM, or IgA) responses specific for cancer by testing for the presence of antibodies that bind to cancer tissue systemically (e.g., in serum) or, for example, at various mucosal sites (e.g., in saliva or gastric and bronchoalveolar lavages) using in vitro assays familiar to those in the art, e.g., an ELISA. Practitioners may also assess the general immunocompetence of the patient by evaluating one or more of: (a) the ability to mount a normal proliferative response to mitogens (e.g., PHA or LPS) or anti-CD3 antibody stimulation; (b) $CD4^+$ cell:$CD8^+$ cell ratios in a predetermined normal range (e.g., $>1.0$); and (c) tumor-specific immune responses such as quantitating T cells specific for tumor antigens using, e.g., ELISPOT or tetramer or cytokine analysis.

Alternatively, or in addition, since CD4+ T cell responses are generally required for antibody responses, in vitro $CD4^+$ T cell responses to the cancer can be measured using methods known in the art. Such methods include $CD4^+$ T cell proliferation or lymphokine (e.g., interleukin-2, interleukin-4, or interferon-$\gamma$) production assays. Part of the determination can include a quantitative or qualitative assessment/evaluation as to whether the patient has previously been administered a chemotherapeutic or immunosuppressive therapy as such therapies are known to inhibit the immune system of the patient to which the therapies are administered.

The following examples are intended to illustrate, not limit, the invention.

EXAMPLES

Example 1

Preliminary Results of a Dose Escalation Trial Evaluating an Anti-CD200 Antibody in Humans Samalizumab (Alexion Pharmaceuticals, Inc.) is a first-in-class recombinant, humanized monoclonal antibody that is currently being evaluated clinically for the treatment of B-CLL. The antibody inhibits the interaction between CD200 and CD200R and thus, in patients with cancers expressing CD200, inhibits CD200-dependent immune suppression. Accordingly, administration to the patient of samalizumab enables the patient's immune system to adequately identify and eradicate the cancer.

An ongoing dose escalation trial was performed to evaluate the safety and maximum tolerated dose (MTD) of samalizumab in patients with relapsing or refractory B-CLL or Multiple myeloma (MM) using a modified Fibonacci design of three patients per cohort. Cohorts were to be expanded to six patients if dose-limiting toxicities (DLT) occurred. Study patients received a single intravenous dose per 28 day cycle and optional additional intravenous doses of samalizumab at 28 day intervals. A total of seven cohorts have been evaluated, ranging from 50 $mg/m^2$ to 600 $mg/m^2$ per treatment cycle. The study has assessed in the patients, among other things, complete blood counts, computed tomography (CT) scans, standard safety evaluations, pharmacokinetic (PK) and pharmacodynamic (PD) measurements of the antibody; and whether an anti-samalizumab antibody response has been generated in the patients.

Figure 1:
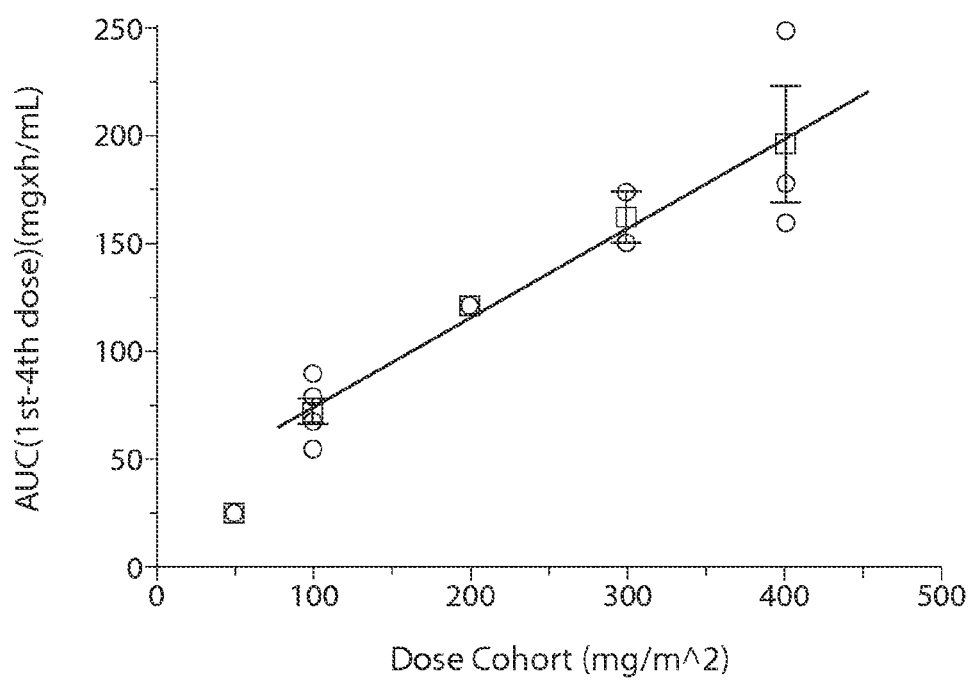
FIG. 1 is a line graph depicting a dose-dependent linear increase in serum AUC (area under the curve) for the first four cycles (doses) of treatment with the anti-CD200 antibody samalizumab. Only subjects that received four doses of samalizumab were included in the AUC analysis. The X-axis depicts the dose (mg/m2) of antibody administered to the patient within a particular cohort (see Examples 1 and 2 below). The Y-axis represents the AUC (for the first, second, third, and fourth doses) in units of (mg×hours)×mL$^{-1}$. The open circles represent individual AUC for each patient within the cohort. The box/whisker represents the mean AUC for each cohort.

The study enrolled 26 B-CLL patients, including three multiple myeloma (MM) patients and one patient with small lymphocytic lymphoma (SLL), in seven (7) dose cohorts with doses ranging from 50 $mg/m^2$ to 600 $mg/m^2$. Two of the MM patients were enrolled in the 500 $mg/m^2$ cohort and one in the 600 $mg/m^2$ cohort. The SLL patient was enrolled in the 500 $mg/m^2$ cohort. Four patients had received no prior chemotherapy for their cancer, whereas the other 22 patients had received a median of two regimens (ranging between 1 to 9 cycles per patient) of chemotherapy prior to administration of the first dose of samalizumab. There were 18 male patients and 8 female patients, the patients having an age range of 41-87 years (the median age being 67). Twenty patients received optional dosing; three of these (one dosed at 50 $mg/m^2$; two dosed at 200 $mg/m^2$) developed a human anti-human antibody response against samalizumab. Nine of 13 patients who completed four (4) dosing cycles exhibited stable disease (SD) based on serial assessments of peripheral blood counts and CT scans. The protocol was amended to allow for greater than four (4) treatment cycles for patients exhibiting SD at four cycles. No clinically adverse cytokine reactions were observed. One non-drug, non-malignancy related death occurred. Adverse events were mostly mild or moderate in severity, and no maximum tolerated dose (MTD) has been observed as of the end of the cohort six evaluation period. Samalizumab exhibits a dose-dependent linear increase in serum area under the curve (AUC). The mean AUC of serum drug levels (100-400 $mg/m^2$) for the first four (4) cycles of treatment are consistent with a linear relationship between dose and AUC (FIG. 1).

Initial results suggest that samalizumab is generally safe and well tolerated and exhibits a desired immunomodulatory activity in this patient population as elaborated on below.

Example 2

Observation of Biomarkers of the Occurrence of an Immunomodulatory Effect in Humans Treated with Samalizumab Among patients with evaluable cell populations, antibody treatment resulted in observable immunomodulatory effects on both immune cells and B-CLL cancer cells in the peripheral blood. A summary of the effects is shown in Table 1. For example, a reduction in $CD200^+$ T cells was observed in 19 out of 20 patients (95%) following administration of samalizumab (Table 1).

TABLE 1

Dosing and Pharmacodynamic (PD) Parameters by Cohort

| Antibody Dose (mg/m$^2$) | N (patients) | | | | N/N evaluable | | | |
|---|---|---|---|---|---|---|---|---|
| | Total | ≥4 cycles | HAHA | Th1 cytokines$^a$ | Antibody-bound CLL | CD200 loss on CLL | CD200$^+$ T cell reduction | CD200R$^+$ T cell increase |
| 50 | 4$^b$ | 1$^c$ | 1$^c$ | 3/4 | 1/4 | 1/4 | 2/2 | 0/2 |
| 100 | 5$^b$ | 5 | 0 | 5/5 | 2/5 | 5/5 | 5/5 | 2/5 |
| 200 | 3 | 1$^d$ | 2 | 3/3 | 2/2 | 2/2 | 3/3 | 2/3 |
| 300 | 3 | 2 | 0 | 3/3 | 1/2 | 1/2 | 2/2 | 2/2 |
| 400 | 3 | 2 | 0 | 2/3 | 2/3 | 3/3 | 2/2 | 0/2 |
| 500 | 7$^e$ | 2 | 0 | 5/6$^f$ | 2/5 | 2/5 | 4/5 | 2/4 |
| 600 | 1$^g$ | 0 | 0 | 1/1 | NA | NA | 1/1 | 0/1 |

Figure 2:
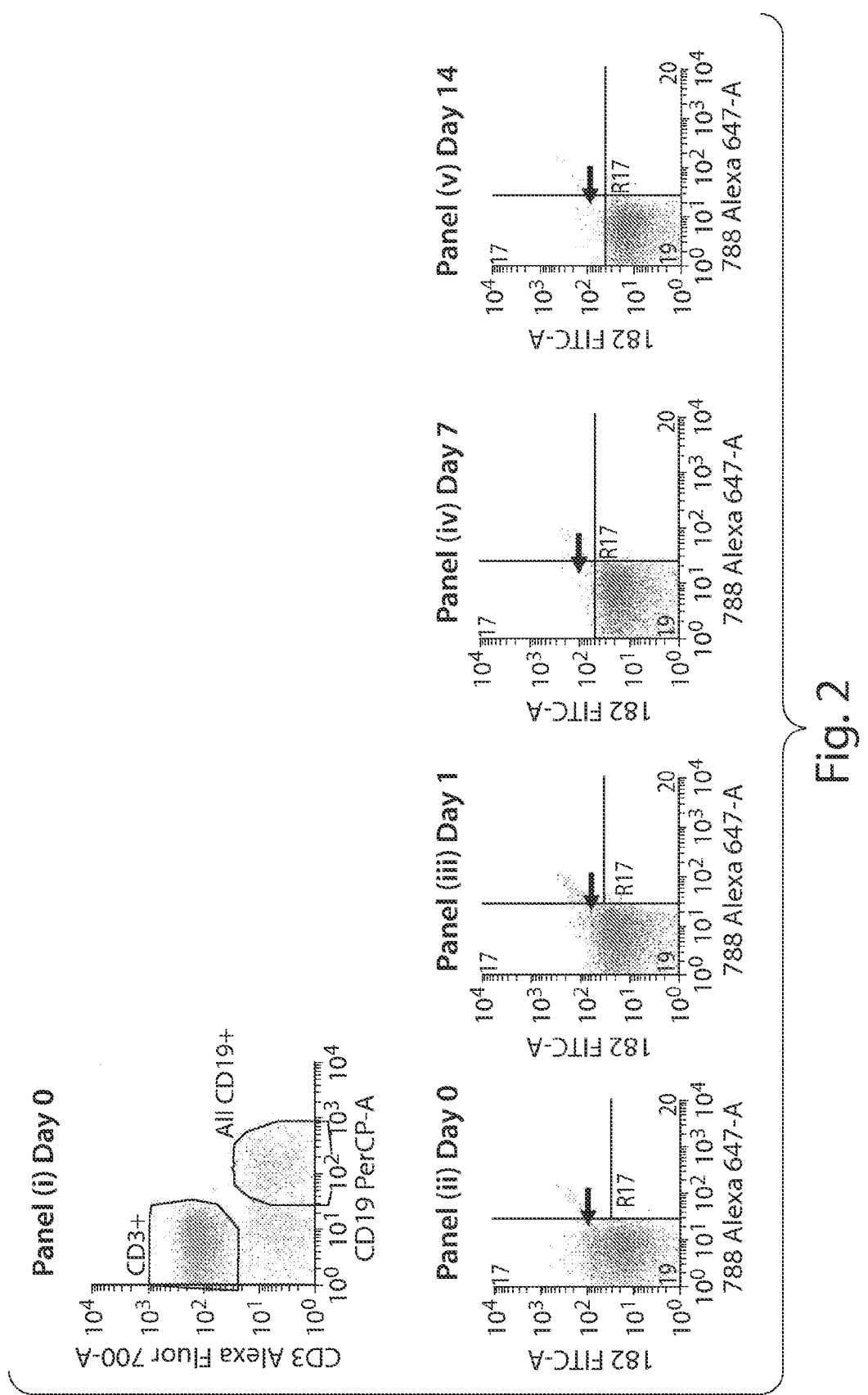
FIG. 2 is a series of flow cytometry dot plots depicting the observed reduction of CD200$^+$ T cells in the peripheral blood of a patient treated with the anti-CD200 antibody samalizumab at 100 mg/m$^2$. In panel (i), the X-axis represents the relative fluorescence intensity of the signal produced from an anti-CD19 antibody/PerCP conjugate bound to the evaluated cells and the Y-axis represents the relative fluorescence intensity of the signal produced from an anti-CD3 antibody/Alexa Fluor® 700 bound to the evaluated cells. The T cells identified in panel (i) were then interrogated for both the expression of CD200 and for evidence of bound samalizumab (panels ii to v). In panels (ii) to (v), the Y-axis represents the relative fluorescence intensity of the signal produced from an anti-CD200 antibody/FITC conjugate bound to CD3$^+$ cells (T cells) in the patient blood sample and the X-axis represents the relative fluorescence intensity of an antibody specific for samalizumab (e.g. an anti-idiotypic antibody)/Alexa 647 conjugate bound to the cells. Panel (i) depicts the flow cytometry profile of cells in a blood sample obtained from the patient prior to administration of samalizumab and specifically the CD3$^+$ and CD19$^+$ populations present in the blood sample. Panel (ii) depicts the flow cytometry profile of the gated CD3$^+$ cell from panel (i), showing the concentration of CD3$^+$ cells in the population of (i) that are also CD200$^+$ (see the upper left quadrant of the panel) on day 0 (prior to samalizumab dosing), and panel (iii) shows the same on day 1 following samalizumab dosing. Panel (iv) depicts the flow cytometry profile showing the concentration of CD200$^+$/CD3$^+$ cells in a biological sample obtained from the patient seven days after the patient was administered samalizumab (see the upper left quadrant of the panel). Panel (v) depicts the flow cytometry profile showing the concentration of CD200'/CD3$^+$ cells in a biological sample obtained from the patient fourteen days after the patient was administered samalizumab (see the upper left quadrant of the panel). The large, filled arrows indicate the relevant cell population.

"Antibody" refers to samalizumab.
"N" is the number of patients.
"HAHA" refers to the occurrence of a human anti-human antibody response against samalizumab in the patient.
$^a$Th1 cytokines detected at any time point during the treatment of the patient.
$^b$Greater than three patients enrolled to evaluate multiple-dose safety.
$^c$Refers to the same patient.
$^d$No HAHA response detected.
$^e$Two of seven patients were Multiple Myeloma (MM) patients
$^f$Th1 cytokine information was not available for one patient in this cohort.
$^g$Patient afflicted with multiple myeloma.
"NA" refers to Not Applicable FIG. 2 provides a representative analysis of a treated patient showing a reduction in CD200+ T cells. As shown in FIG. 3, the reduction of CD200$^+$ T cells in patients was transient, with CD200$^+$ T cells beginning to recover to pre-treatment levels around day 14. However, administration of a second dose of samalizumab to these patients again resulted in a transient reduction in the concentration of CD200$^+$ T cells (FIG. 3). The transient nature of the effect was observed more frequently at lower doses of samalizumab (e.g., 50 to 200 mg/m$^2$), compared to a sustained effect at higher doses (300 to 500 mg/m$^2$) of the antibody. This indicated that the immunomodulatory effect of the anti-CD200 antibody in the patients was dose-dependent and that modification of a dosing schedule to maintain the immunomodulatory effect in the patients could be achieved by one or both of an increase in the dose of samalizumab and/or more frequent administration of samalizumab.

The reduction or recovery in CD200$^+$ T cells was not associated with an overall change in the total concentration of CD3$^+$ T cells in the patients suggesting that the CD200+ T cells are either downregulating CD200 expression and/or are being mobilized out of the periphery, rather than being deleted. (Samalizumab does not crossblock the binding of the antibody used to detect CD200 expression by the leukocytes in the patient blood samples, and thus does not substantially affect the ability to detect CD200 expression using these assays).

Figure 4:
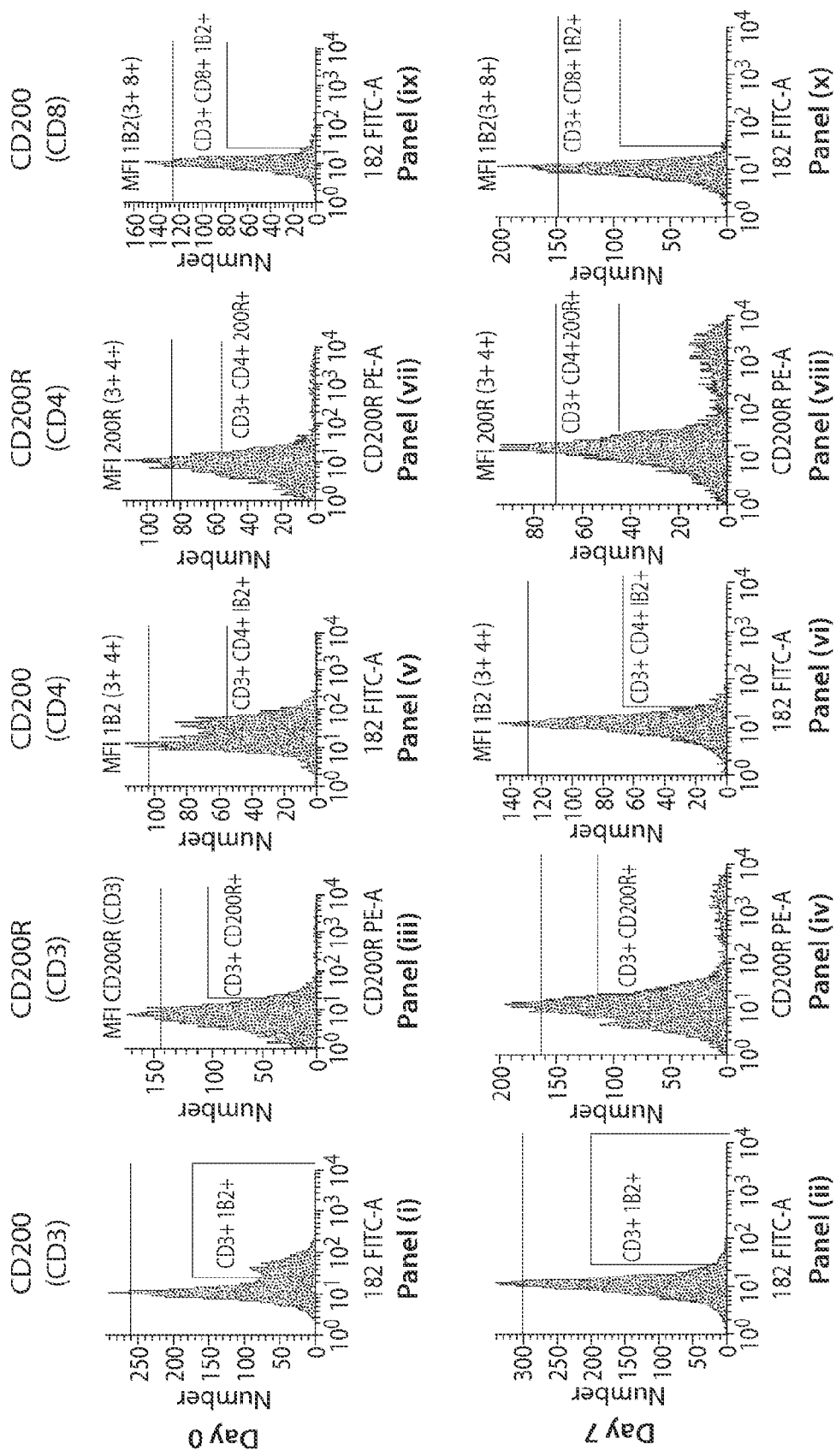
FIG. 4 is a series of flow cytometry histograms depicting the change in expression of CD200 and CD200R on CD4$^+$ and CD8$^+$ T cell subsets in blood samples obtained from a patient treated with samalizumab at a dose of 100 mg/m². The Y-axis in all panels represents the number of cells. In panels (i), (ii), (v), (vi), (ix), and (x), the X-axis represents the relative fluorescence intensity of an anti-CD200 antibody/FITC conjugate bound to the cells. In panels (iii), (iv), (vii), and (viii), the X-axis represents the relative fluorescence intensity of an anti-CD200R antibody/phycoerythrin conjugate bound to the cells. Panel (i) depicts the number of CD200$^+$/CD3$^+$ T cells in a blood sample from the patient prior to receiving samalizumab. Panel (ii) depicts the number of CD200$^+$/CD3$^+$ T cells in a blood sample from the patient obtained seven days after receiving samalizumab. Panel (iii) depicts the number of CD200R$^+$/CD3$^+$ T cells in a blood sample from the patient prior to receiving samalizumab. Panel (iv) depicts the number of CD200R$^+$/CD3$^+$ T cells in a blood sample from the patient obtained seven days after receiving samalizumab. Panel (v) depicts the number of CD200$^+$/CD3$^+$/CD4$^+$ T cells in a blood sample from the patient prior to receiving samalizumab. Panel (vi) depicts the number of CD200$^+$/CD3$^+$/CD4$^+$ T cells in a blood sample from the patient obtained seven days after receiving samalizumab. Panel (vii) depicts the number of CD200R$^+$/CD3$^+$/CD4$^+$ T cells in a blood sample from the patient prior to receiving samalizumab. Panel (viii) depicts the number of CD200R$^+$/CD3$^+$/CD4$^+$ T cells in a blood sample from the patient obtained seven days after receiving samalizumab. Panel (ix) depicts the number of CD200$^+$/CD3$^+$/CD8$^+$ T cells in a blood sample from the patient prior to receiving samalizumab. Panel (x) depicts the number of CD200$^+$/CD3$^+$/CD8$^+$ T cells in a blood sample from the patient obtained seven days after receiving samalizumab.

In addition, an elevated level of CD200R expression on leukocyte subsets (e.g., CD200R$^+$/CD4$^+$ leukocyte subsets) by day seven (7) following the administration of samalizumab was also observed in eight of 19 patients (see, e.g., FIG. 4). Reductions in CD200$^+$ cells and increases in CD200R expression by leukocytes were predominately observed in the CD4$^+$ T cell populations (FIG. 4). As described above, increases in CD200R expression by leukocyte subsets may be the result of compensation by the cells to the reduction in CD200 expression.

Ten out of 25 patients (40%) exhibited modest first-dose Th1 cytokine responses, whereas twenty-two of twenty-five (88%) patients had detectable Th1 cytokines at one or more time points during the study. This is also consistent with immunomodulatory activity of samalizumab in the patients.

Figure 5:
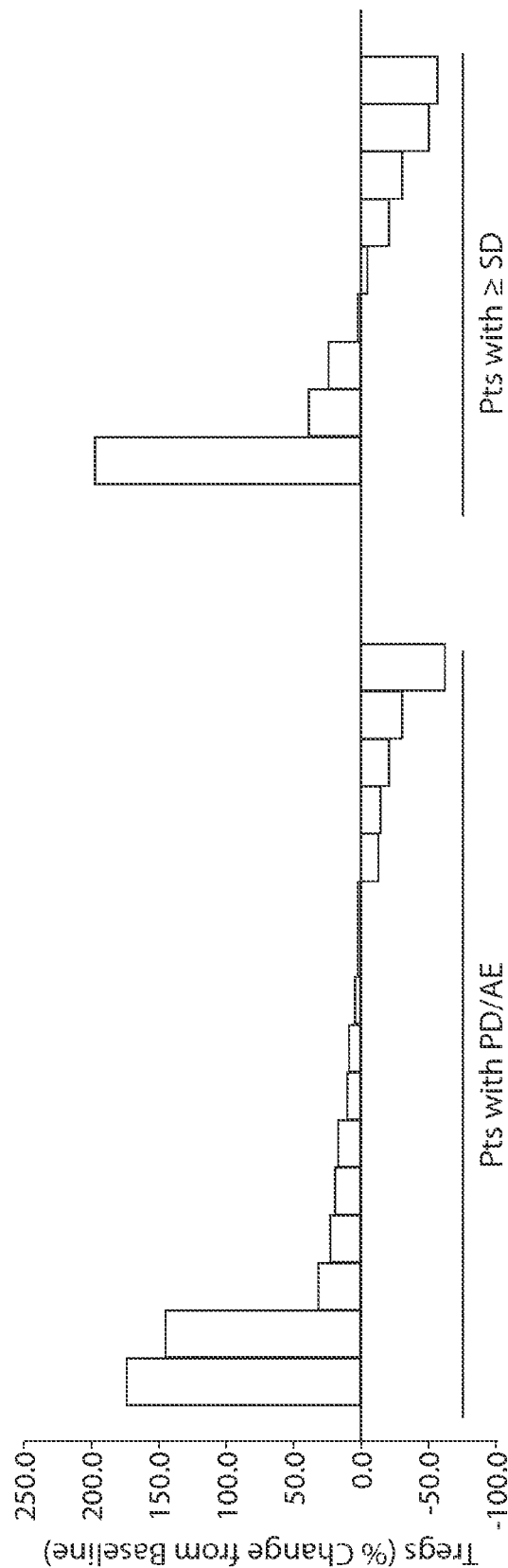
FIG. 5 is a bar graph depicting the reduction in regulatory T cells (CD4$^+$/CD25$^+$/FoxP3$^+$) in subsets of samalizumab-treated patients having stable or improved disease ("≥SD"; rightmost grouping of bars) or progressive disease/adverse events ("PD/AE"; leftmost grouping of bars). Each bar within the graph represents an individual patient. The Y-axis represents the percentage change in the concentration of regulatory T cells at the last visit, as compared to baseline (the concentration of cells of the same histological type in a biological sample obtained from the patient prior to administration of the antibody), in a biological sample obtained from each patient.

A loss of regulatory T cells (Tregs) was also observed in patients administered samalizumab. Particularly four out of nine (44.4%) patients with clinically stable or improved disease exhibited a reduction in Tregs, whereas only five out of sixteen (31.2%) patients whose disease clinically progressed exhibited a similar loss of Tregs (FIG. 5).

Figure 6:
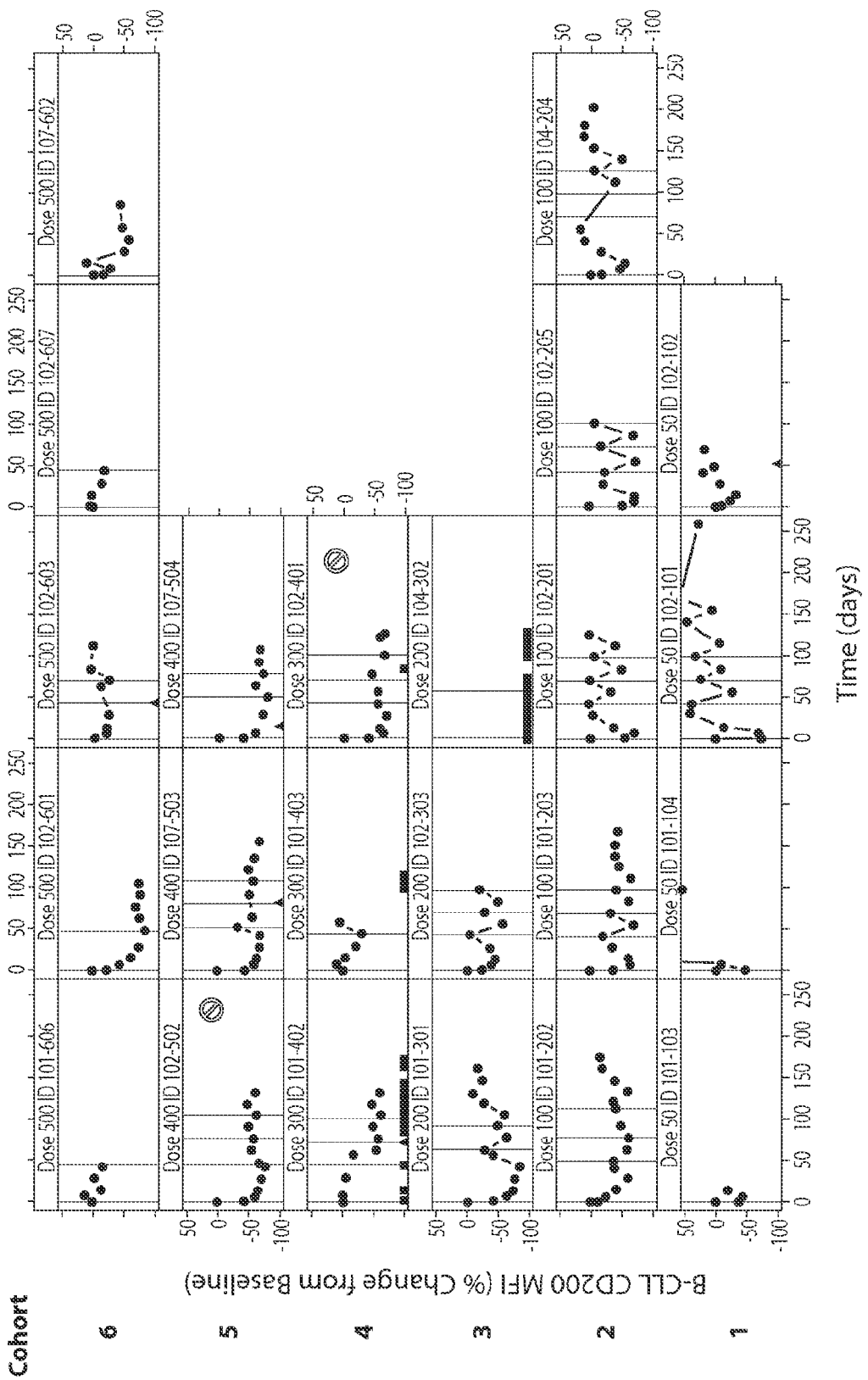
FIG. 6 is a series of line graphs depicting the reduction in CD200$^+$ expression by B-CLL cells in different patients, respectively, following the administration of different doses of samalizumab to the patients. The Y-axis represents the percent (%) change from baseline in mean fluorescence intensity (MFI) of an anti-CD200 antibody/FITC conjugate bound to B-CLL cells present in the patient samples. The numeric units identified on the Y-axis are, in descending order from the top of each graph: 50, 0, −50, and −100. The X-axis represents the time in days following initial administration of samalizumab. The vertical bars represent the days on which samalizumab was administered. Each row of line graphs corresponds to a particular cohort numbered 1 to 6. As elaborated on below in the working Examples, patients in cohort 6 received 500 mg/m² of samalizumab each dose. Patients in cohort 5 received 400 mg/m² of samalizumab each dose. Each dose of samalizumab administered to patients in cohort 4 was 300 mg/m². Each dose of samalizumab administered to patients in cohort 3 was 200 mg/m². Patients in cohort 2 received 100 mg/m² of samalizumab and patients in cohort 1 received 50 mg/m² of samalizumab for each dose. Each individual line graph corresponds to one patient within each cohort. Unevaluable patients are designated by a once-crossed circle.

A reduction of CD200 protein expression by B-CLL tumor cells in the peripheral blood was also observed in 14 of 21 patients (67%) following administration of samalizumab. The reduction was transient at lower doses of samalizumab (e.g., 50 to 200 mg/m$^2$), with CD200 expression by B-CLL cells beginning to recover to (or nearly to) pre-treatment levels around day 14. However, administration of a second dose of samalizumab to these patients again resulted in a transient reduction in the expression of CD200 protein by the cells (FIG. 6). A sustained loss of CD200 on B-CLL tumor cells was observed at higher doses (300 to 500 mg/m$^2$) of the antibody. As noted above, this result further indicated that the immunomodulatory effect of the anti-CD200 antibody in the patients was dose-dependent and that modification of a dosing strategy to maintain the immunomodulatory effect in the patients could be achieved by one or both of an increase in the dose of samalizumab and/or more frequent administration of samalizumab. Such an anti-CD200 antibody dosing strategy will likely provide improved clinical benefit to treated patients.

Changes in expression of CD200R and/or CD200 on other leukocyte subsets, or a change in the concentration of other CD200$^+$ or CD200R$^+$ leukocytes was not observed due to a lack of sufficient quantity of cells to make such an observation.

Of the nine patients exhibiting stable disease, one was from cohort 1, three were from cohort 2, one in each of cohorts 3, 4 and 5, and two in the higher dose cohort (500 mg/m$^2$). Exemplary anti-CD200 antibody-associated immunomodulatory effects observed in the patients are as follows:

1. CD4$^+$/CD200$^+$ T cells: All patients with stable disease in cohorts 1, 2 and 3 showed a transient reduction in CD200$^+$/CD4$^+$ T cells after the 1$^{st}$ and subsequent samalizumab doses. Patient in cohorts 4, 5 and 6 with stable disease exhibited a sustained reduction in CD200+/CD4+ T cells.

2. CD200R+/CD4+ T cell: One of three of the patients in cohort 2 with stable disease, the patient in cohort 3, and the patient in cohort 4 (all with stable disease) exhibited an increase in CD200R+/CD4+ T cells after the first dose.

These patients with stable disease had varying numbers of T cells at baseline (2%, 2%, 14%, 23% and 39% of the CD45+ leukocytes) and percent CD4+/CD200+ T cells varied from 10-35% of total CD3+ T cells at baseline in these patients. In addition, in all patients with stable disease, the expression of CD200 on the B CLL cells was reduced.

These results indicate that the anti-CD200 antibody is capable of producing an immunomodulatory effect in patients to whom the antibody was administered. As nine patients treated with samalizumab exhibited stable disease at four treatment cycles, the biomarkers may also indicate that the dose of samalizumab, by virtue of its observed immunomodulatory effect in the human, is sufficient to achieve a clinically-meaningful effect on the disease.

Example 3

Biomarkers, Immunomodulatory Effect, and Efficacy of Samalizumab Treatment in Patients Who Had not Previously Received Chemotherapy As described above, four of the patients enrolled in the study had not received chemotherapy prior to the samalizumab therapy. All four of these patients received samalizumab therapy and exhibited clinically stable or improved disease—four of the nine responders. One of the four patients, patient 102-502, is a 66 year old male who presented with advanced CLL (RAI stage 4 at study entry with no prior treatment), including a large abdominal mass and fatigue at the point of enrollment. Prior to beginning the anti-CD200 antibody treatment regimen, patient 102-502 had not received any chemotherapeutic treatments or other immunosuppressive therapies for CLL. Within weeks after receiving the first 400 mg/m$^2$ dose of samalizumab, the patient's abdominal mass had been reduced by 57.6% as determined by CT scan. The patient's treatment with samalizumab continued for an additional four cycles (4 doses) at 400 mg/m$^2$. After the fourth cycle, the patient's abdominal mass had been further reduced—a total of a 71% reduction since the time of enrollment. The patient's fatigue had also been eliminated. The patient has received 13 doses of samalizumab administered once per month and has achieved a partial response (PR).

Figure 7A:
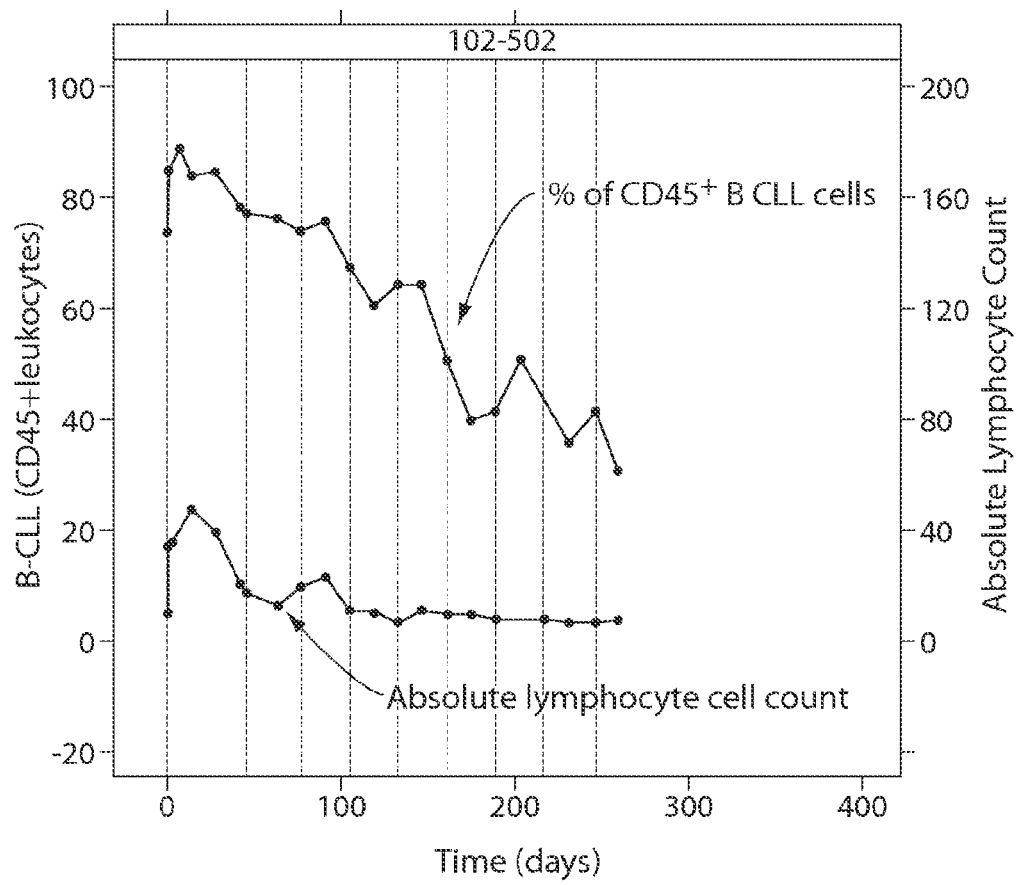
FIG. 7A is a line graph depicting embodiments of the immunomodulatory effect of samalizumab as observed in CLL patient 102-502. The X-axis represents time in days. The Y-axis to the left of FIG. 7A represents the percentage of CD45$^+$ B-CLL cells as measured in a blood sample obtained from the patient. The Y-axis to the right of FIG. 7A represents the absolute lymphocyte count in a blood sample obtained from the patient. The vertical, hashed lines represent points at which samalizumab was administered to the patient. Each dose of samalizumab administered to patient 102-502 was 400 mg/m².
Figure 8B:
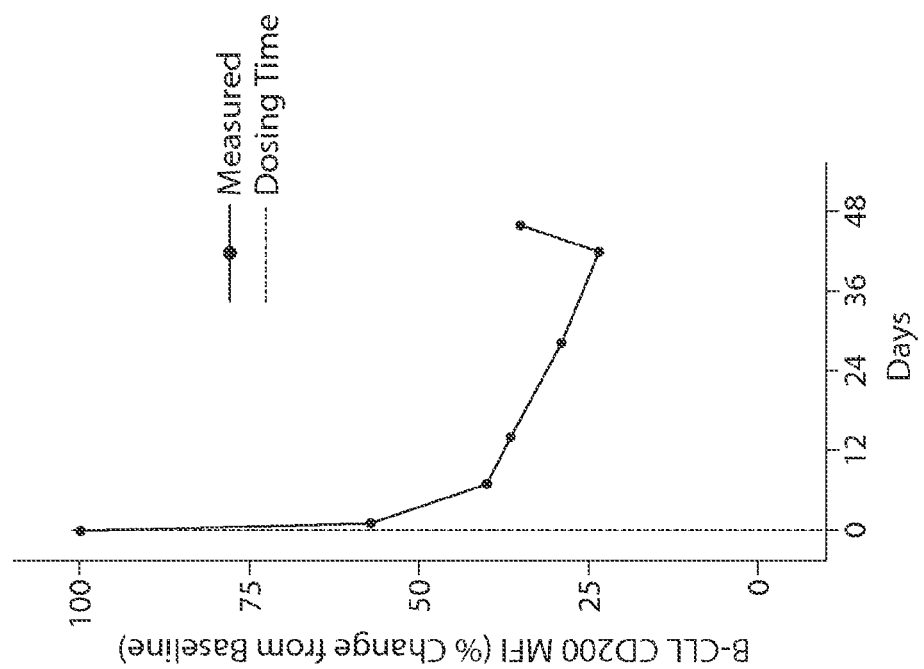
FIG. 8B is a line graph depicting the reduction in the level of CD200 expression by B CLL cells in patient 102-502 over time after the first dose. The Y-axis represents the mean fluorescence intensity (MFI) of an anti-CD200 antibody/FITC conjugate bound to B-CLL cells present in the patient samples. The X-axis represents the time in days following administration of samalizumab.
Figure 8A:
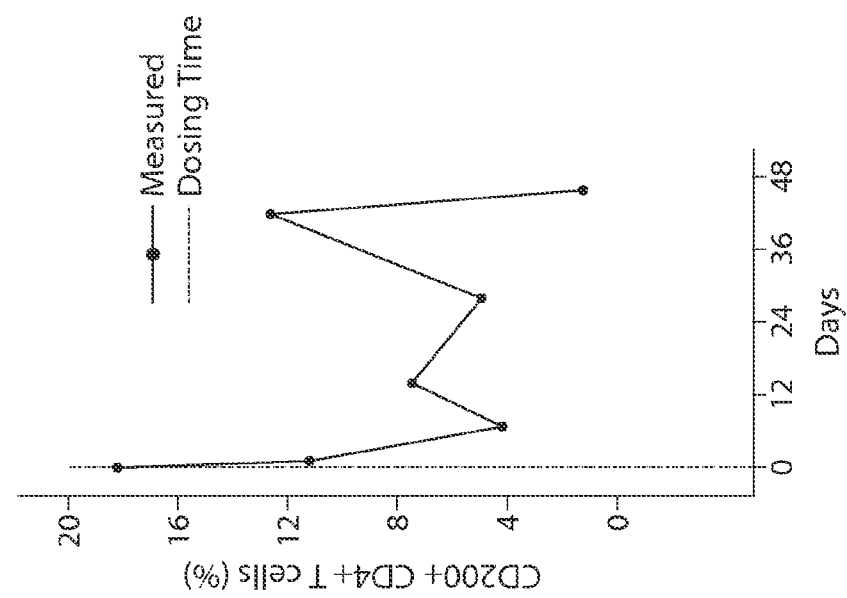
FIG. 8A is a line graph depicting the reduction in the percentage of CD200$^+$/CD4+ T cells in patient 102-502 over time after the first dose. The Y-axis represents the percentage of CD200$^+$/CD4$^+$ T cells. The X-axis represents the time in days following administration of samalizumab.

Concomitantly with the reduction in tumor burden (FIG. 7A), a change in a number of anti-CD200 antibody-associated immunomodulatory biomarkers was observed in this patient. For example, like other evaluated patients, the concentration of CD200+ lymphocytes (e.g., CD200+CD4+ T cells) also decreased in this patient over the course of treatment (FIG. 8A). In addition, the concentration of B CLL cells and the expression level of CD200 by the remaining B CLL cells were also dramatically reduced in this patient (FIG. 8B).

Figure 7B:
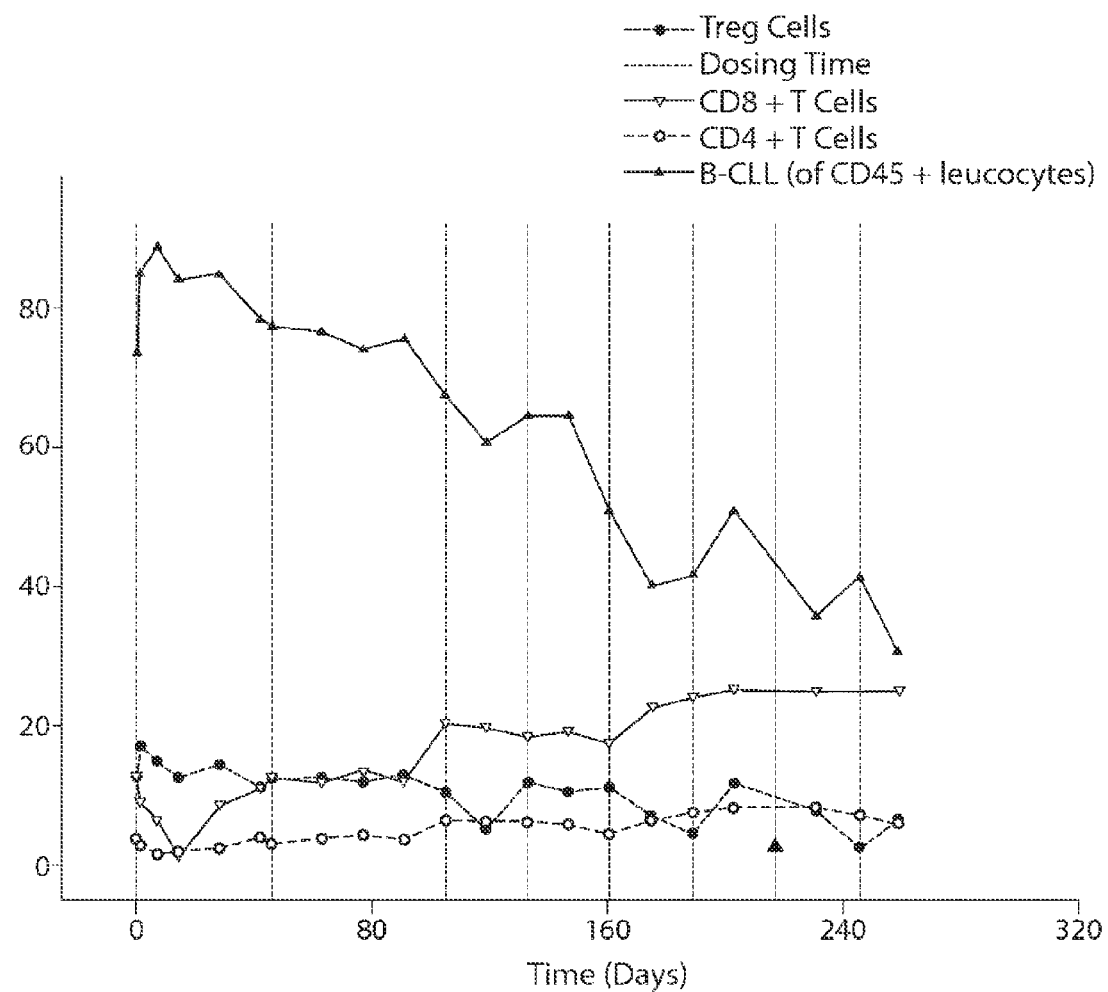
FIG. 7B is a line graph depicting an embodiment of the immunomodulatory effect of samalizumab as observed in CLL patient 102-502. The X-axis represents time in days. The filled triangles represent the percentage of circulating CD45$^+$ B CLL cells. The non-filled triangles represent the percentage of CD8$^+$ T cells. The lines representing the percentage of CD4$^+$ T cells or regulatory T cells are indicated by arrows. The Y-axis of FIG. 7B represents the percentage of lymphocyte cells in the assayed population. The vertical, hashed lines represent points at which samalizumab was administered to the patient.
Figure 9:
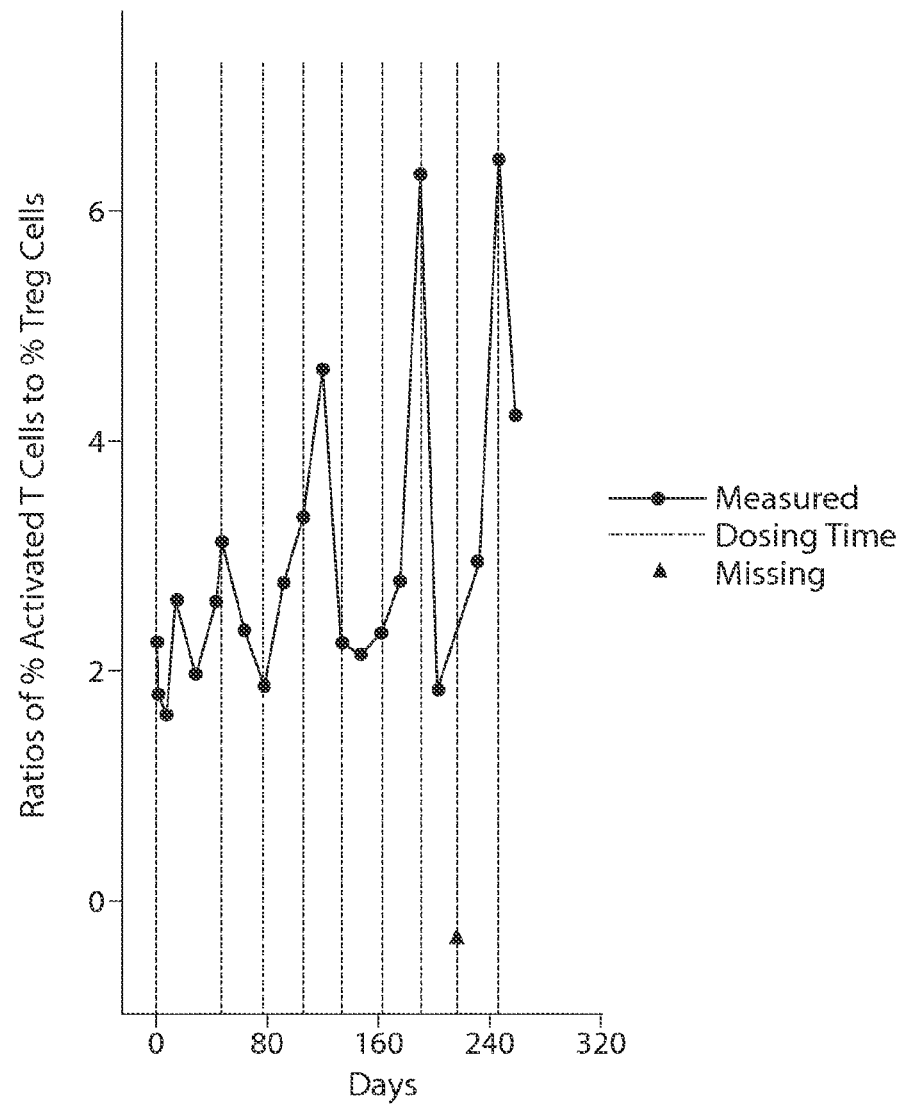
FIG. 9 is a line graph depicting the change in ratio of percent activated T cells to percent regulatory T cells in patient 102-502. The X-axis represents time in days. Y-axis represents ratio of percent activated T cells to percent regulatory T cells in the assayed population. The vertical, hashed lines represent points at which samalizumab was administered to the patient.

Also observed in the patient was an increase in CD8+ T cells as well as CD4+ T cells (FIG. 7B). In contrast, there was a loss of Tregs in patient 102-502 over the course of the treatment. The ratio of percent activated T cells to percent regulatory T cells increased over the course of treatment from approximately 2:1, to 3:1, to 4:1, to 5:1, and eventually to over 6:1. See FIG. 9.

These results further indicated that the anti-CD200 antibody is even more capable of producing an immunomodulatory effect in patients and that changes in the biomarkers described herein correlate with a clinically-meaningful effect on the disease. That four of the nine responders had not, prior to administration of the anti-CD200 antibody, received any chemotherapeutic treatment for CLL so as to immunosuppress the patients indicates that administration of an anti-CD200 antibody to a patient with an intact immune system (or one that has not been compromised by immunosuppressive agents) may likely receive an even greater therapeutic benefit from an anti-CD200 antibody therapy described herein.

Example 4

Efficacy of an Anti-CD200 Antibody in a Mouse Model of Autoimmune Hemolytic Disease Study 0 (Prevention Model).

Therapeutic anti-CD200 antibodies were tested for their ability to prevent, delay, or lessen the severity of, the production of autoantibodies associated with autoimmune hemolytic disease using a mouse model of the disease. See, e.g., Playfair and Marshall-Clarke (1973) *Nat New Biol* 243:213-214; Naysmith et al. (1981) *Immunol Rev* 55:55-87.

To elicit in mice the production of autoantibodies that bind to mouse red blood cells (RBCs), 2×10$^8$ rat RBCs were administered intraperitoneally (i.p.) to female C57BL/6 mice once on study day 0 and then once per week thereafter for the remainder of the study. Production of anti-rat RBC alloantibodies by the immunized mice was observed by the second week of the study and production by the mice of anti-mouse RBC autoantibodies was observed by week three.

The rat RBC-immunized mice were divided into six experimental groups designated: Group 1 (six mice), Group 2 (6 mice), Group 3 (8 mice), Group 4 (7 mice), Group 5 (9 mice), and Group 6 (9 mice). One additional group—Group 7 (6 mice)—was also evaluated as a control. The Group 7 mice were neither immunized with rat RBCs nor did they receive any of the additional treatments described below.

Starting at day 0 (that is the day of the first administration of the rat RBCs), the mice of each of Groups 2 to 6 were administered a therapeutic agent or vehicle under the following schedule: for each week of the study, five doses of agent or vehicle administered as one dose per day for five consecutive days. Group 1 mice were treated with only vehicle-phosphate-buffered saline (PBS). Group 2 mice were treated under the above treatment schedule using 5 mg/kg of a Control antibody that does not bind to CD200, but possesses effector function (IgG2a). Group 3 mice were treated under the aforementioned treatment schedule with Antibody 1—an anti-CD200 antibody (IgG2a) having effector function—each dose being 5 mg/kg. Group 4 mice were treated with cyclosporine at a dose of 15 mg/kg. Group 5 mice were treated with the Control Antibody at 5 mg/kg and cyclosporine at 15 mg/kg. Group 6 mice were treated with Antibody 1 at a dose of 5 mg/kg and cyclosporine at a dose of 15 mg/kg. The antibody treatments were administered i.p. Cyclosporine was administered to the mice subcutaneously (s.c.). The Group design and treatment schedules for each group are summarized in Table 2.

TABLE 2

Group Design and Treatment Schedule for Study 0.

| Groups | N | Therapeutic Administered | Dose |
|---|---|---|---|
| Group 1 | 6 | Vehicle | N/A |
| Group 2 | 6 | Control antibody (IgG2a) that does not bind to CD200 but possesses effector function | 5 mg/kg |
| Group 3 | 8 | Antibody 1 (anti-CD200 antibody IgG2a with effector function) | 5 mg/kg |
| Group 4 | 7 | Cyclosporine | 15 mg/kg |
| Group 5 | 9 | Control antibody (IgG2a) that does not bind to CD200 but possesses effector function; and Cyclosporine | 5 mg/kg<br>15 mg/kg |
| Group 6 | 9 | Antibody 1 (anti-CD200 antibody IgG2a with effector function); and Cyclosporine | 5 mg/kg<br>15 mg/kg |
| Group 7 | 6 | Non-immunized, non-treated control group | N/A |

N refers to the number of mice in each group.
N/A = not applicable.

Figure 10:
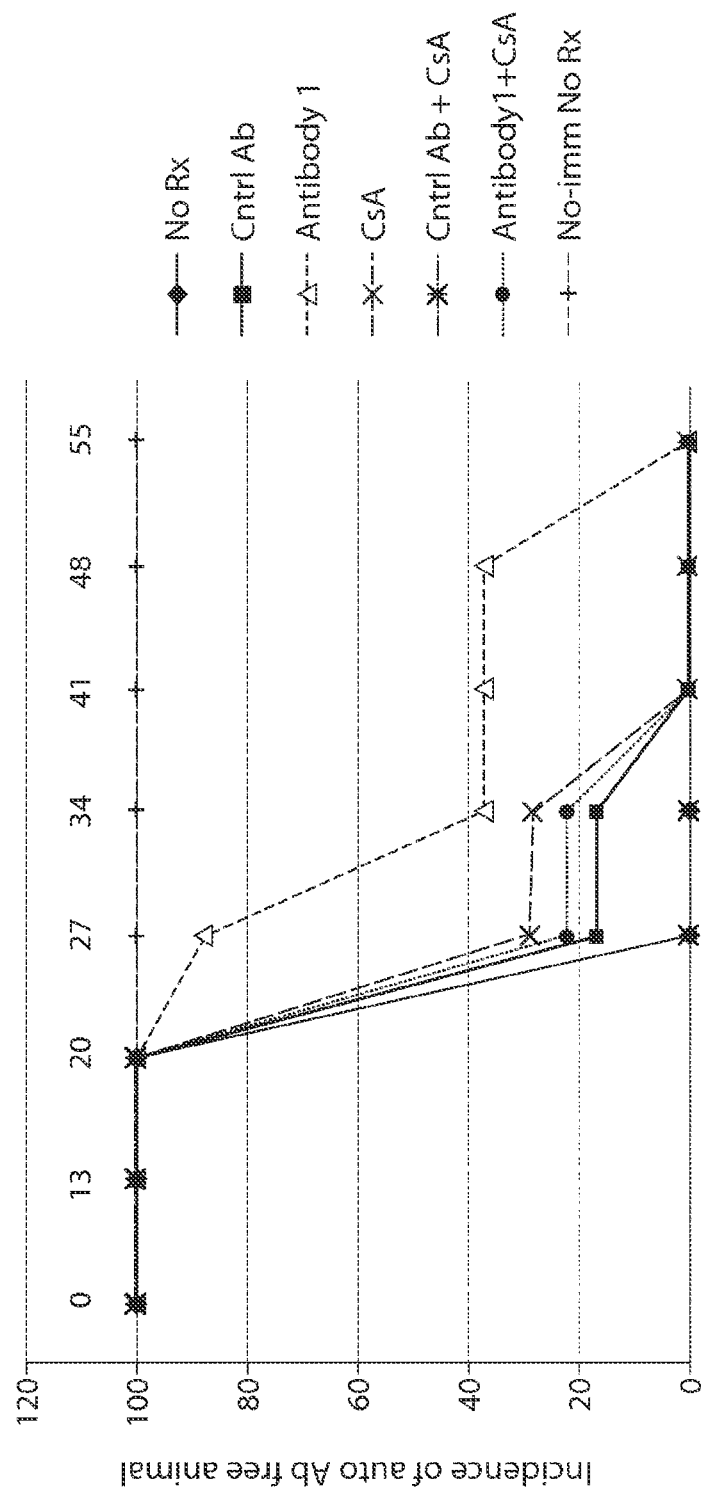
FIG. 10 is a line graph depicting the delay in anti-mouse RBC autoantibody production in mice with autoimmune hemolytic disease treated with an anti-CD200 antibody. The Y-axis represents the incidence (%) of autoantibody production in the mice in each group. The X-axis represents the time in which the presence of autoantibodies in each mouse is detected. The seven groups of mice evaluated included: mice that were immunized with rat RBCs, but not treated with an antibody (No Rx); mice that were immunized with rat RBCs and treated with a control antibody (Cntrl Ab); mice that were immunized with rat RBCs and treated with an anti-CD200 antibody (Antibody 1); mice that were immunized with rat RBCs and treated with cyclosporine (CsA); mice that were immunized with rat RBCs and treated with the control antibody and cyclosporine A (Cntrl Ab+CsA); mice that were immunized with rat RBCs and treated with an anti-CD200 antibody and cyclosporine A (Antibody 1+CsA); and mice that were neither immunized with rat RBCs nor treated with antibody or cyclosporine (No-imm No Rx).

On a weekly basis, blood was drawn from the mice of Groups 1 to 7 prior to, during, and after the above treatments to evaluate by flow cytometry whether treatment affected the titer of anti-mouse RBC autoantibodies and/or anti-rat RBC alloantibodies in the mice. To determine the relative concentration of anti-mouse autoantibodies produced in a subject mouse (e.g., a treated mouse from Group 3), whole blood obtained from the mouse was incubated with a preparation of fluorescently-labeled anti-mouse antibody to thereby detect the presence of anti-mouse RBC antibodies present on the surface of mouse RBC in the blood of the animals. The cells were washed with PBS and then subjected to flow cytometry to evaluate the relative amount of mouse anti-mouse RBCs bound to the mouse RBCs as a function of the mean fluorescence intensity. Between day 13 and 27, the concentration of anti-mouse RBC autoantibodies in the mice of Groups 1, 2, 4, 5, and 6 increased. In contrast, the concentration of anti-mouse RBC autoantibodies in the mice of Group 3 was markedly reduced as compared to the concentration of autoantibody in the other groups. In addition, the production of autoantibody by the mice in Group 3 was markedly delayed as compared to the mice in the other groups (FIG. 10). For example, 50% of mice in Groups 1, 2, 4, 5, and 6 developed autoantibodies between day 20 and 27 of the study. In contrast, autoantibody production in at least 50% of mice in Group 3 did not occur until between day 27 and day 34. These results indicate that Antibody 1, an anti-CD200 antibody, at 5 mg/kg was capable of not only reducing the concentration of anti-mouse RBC autoantibodies in a mice model of autoimmune hemolytic disease, but was also capable of delaying significantly the production of the autoantibodies in the mice.

To determine the relative concentration of alloantibodies produced in a subject mouse (e.g., a treated mouse from Group 3), serum obtained from the mouse was incubated with a sample of isolated rat RBCs for a time and under conditions sufficient for any rat RBC-specific alloantibodies present in the serum to bind to the rat RBCs. The cells were washed with PBS and then incubated with a fluorescently-labeled antibody that binds to mouse antibodies. Following an additional washing step, the cells were subjected to flow cytometry to evaluate the relative amount of mouse anti-rat RBCs bound to the rat RBCs as the mean fluorescence intensity. Sera obtained from mice of Groups 1, 2, 4, 5, and 6 contained an increasing concentration of anti-rat RBC alloantibodies over the course of the experiment. In contrast, sera obtained from the mice of Group 3 contained much less detectable anti-rat RBC autoantibodies as compared to the other Groups. These results further indicated that Antibody 1, an anti-CD200 antibody, at 5 mg/kg was capable of reducing the titer of RBC-specific alloantibodies, as well as anti-RBC autoantibodies, produced in a mouse model of autoimmune hemolytic disease.

Study 1 (Treatment Model).

Therapeutic anti-CD200 antibodies were tested for their ability to reduce the production of autoantibodies associated with autoimmune hemolytic disease using a mouse model of the disease. To elicit in mice the production of autoantibodies that bind to mouse red blood cells (RBCs), $2 \times 10^8$ rat RBCs were administered intraperitoneally (i.p.) to female C57BL/6 mice once on study day 0 and then once per week thereafter for the remainder of the study. Production of anti-rat RBC alloantibodies by the immunized mice was observed by the second week of the study and production by the mice of anti-mouse RBC autoantibodies was observed by week three.

The rat RBC-immunized mice were divided into five groups designated Group 1 (8 mice), Group 2 (8 mice), Group 3 (8 mice), Group 4 (7 mice), and Group 5 (8 mice). A sixth group of mice (designated Group 6; 6 mice) was also evaluated as a control. The Group 6 mice were neither immunized with rat RBCs nor did they receive any of the additional treatments described below.

Starting on day 112, the mice of each of Groups 1 to 5 received an additional treatment of 14 doses of a therapeutic agent or vehicle control administered under the following schedule: (i) five doses of agent or vehicle administered as one dose per day for five consecutive days; (ii) a two day break in treatment; (iii) an additional five doses of the agent or vehicle administered one dose per day for five consecutive days; another two day break in treatment; and (iv) four more doses of agent or vehicle administered one dose per day for four consecutive days. Group 1 mice were treated with only vehicle-phosphate-buffered saline (PBS). Group 2 mice were treated under the aforementioned treatment schedule with Antibody 1—an anti-CD200 antibody (IgG2a) having effector function—each dose being 5 mg/kg. Group 3 mice were treated with Antibody 1 at a dose of 1 mg/kg. Group 4 mice were treated under the above treatment schedule with Antibody 2—an anti-CD200 antibody that lacked effector function—each dose at 5 mg/kg. Group 5 mice were treated under the above treatment schedule using a dose of 5 mg/kg of a Control antibody that does not bind to CD200, but possesses effector function (IgG2a). The Group design and treatment schedules for each group are summarized in Table 3.

TABLE 3

Group Design and Treatment Schedule for Study 1.

| Groups | N | Therapeutic Administered | Dose |
|---|---|---|---|
| Group 1 | 8 | Vehicle | N/A |
| Group 2 | 8 | Antibody 1 (anti-CD200 antibody IgG2a with effector function) | 5 mg/kg |
| Group 3 | 8 | Antibody 1 (anti-CD200 antibody IgG2a with effector function) | 1 mg/kg |
| Group 4 | 7 | Antibody 2 (anti-CD200 antibody that does not possess effector function) | 5 mg/kg |
| Group 5 | 8 | Control antibody (IgG2a) that does not bind to CD200 but possesses effector function | 5 mg/kg |
| Group 6 | 6 | Non-immunized, non-treated control group | N/A |

N refers to the number of mice in each group.
N/A = not applicable.

On a weekly basis, blood was drawn from the mice of Groups 1 to 6 prior to, during, and after the above treatments to evaluate by flow cytometry whether treatment affected the titer of anti-mouse RBC autoantibodies and/or anti-rat RBC alloantibodies in the mice. Between day 133 and 137 of the study, the mice were sacrificed and their spleens harvested. To determine the relative concentration of alloantibodies produced in a subject mouse (e.g., a treated mouse from Group 2), serum obtained from the mouse (e.g., at day 133) was contacted to a sample of isolated rat RBCs for a time and under conditions sufficient for any rat RBC-specific alloantibodies present in the serum to bind to the rat RBCs. The cells were washed with PBS and then incubated with a fluorescently-labeled antibody that binds to mouse antibodies. Following an additional washing step, the cells were subjected to flow cytometry to evaluate the relative amount of mouse anti-rat RBCs bound to the rat RBCs as the mean fluorescence intensity. The inventors observed that the post-treatment sera obtained from mice of Groups 1, 3, 4, and 5 contained an increased concentration of anti-rat RBC alloantibodies as compared to the corresponding sera obtained from the mice prior to treatment. In contrast, sera obtained from the mice of Group 2 post-treatment contained less detectable anti-rat RBC alloantibodies as compared to the corresponding sera obtained from the mice prior to treatment. These results indicated that Antibody 1, an anti-CD200 antibody, at 5 mg/kg was capable of reducing the production of RBC-specific antibodies in a mouse model of autoimmune hemolytic disease.

The inventors subsequently observed that Antibody 2 had a significantly shorter half-life in the treated mice as compared to the half-life of Antibody 1. Thus the results observed with Antibody 2 in Study 1 and in other studies described herein may not fully reflect the true efficacy of the Antibody 2 in the autoimmune hemolytic disease model nor the immunodulatory effect of the antibody in animals.

Study 2 (Prevention Model).

Therapeutic anti-CD200 antibodies were tested for their ability to prevent, delay, or lessen the severity of, the production of autoantibodies associated with autoimmune hemolytic disease using the above-described mouse model of the disease.

To elicit in mice the production of autoantibodies that bind to mouse red blood cells (RBCs), rat RBCs were administered intraperitoneally (i.p.) to female BALB/c mice once on study day 0 and then once per week thereafter for the remainder of the study. As described above, production of anti-rat RBC alloantibodies by the immunized mice was observed by the second week of the study and production by the mice of anti-mouse RBC autoantibodies was observed by week three.

The rat RBC-immunized mice were divided into five groups designated Group 1 (8 mice), Group 2 (8 mice), Group 3 (8 mice), Group 4 (8 mice), and Group 5 (8 mice). A sixth group of mice (designated Group 6; 6 mice) was also evaluated as a control. The Group 6 mice were neither immunized with rat RBCs nor did they receive any of the additional treatments described below.

Starting at day 0 (that is the day of the first administration of the rat RBCs), the mice of each of Groups 1 to 5 were administered a therapeutic agent or vehicle under the following schedule: for each week of the study, five doses of agent or vehicle administered as one dose per day for five consecutive days. Group 1 mice were treated with only vehicle-phosphate-buffered saline (PBS). Group 2 mice were treated under the aforementioned treatment schedule with Antibody 1—an anti-CD200 antibody (IgG2a) having effector function—each dose being 5 mg/kg. Group 3 mice were treated with Antibody 1 at a dose of 1 mg/kg. Group 4 mice were treated under the above treatment schedule with Antibody 2—an anti-CD200 antibody that lacked effector function—each dose at 5 mg/kg. Group 5 mice were treated under the above treatment schedule using 5 mg/kg of a Control antibody that does not bind to CD200, but possesses effector function (IgG2a). The Group design and treatment schedules for each group are summarized in Table 4.

TABLE 4

Group Design and Treatment Schedule for Study 2.

| Groups | N | Therapeutic Administered | Dose |
|---|---|---|---|
| Group 1 | 8 | Vehicle | N/A |
| Group 2 | 8 | Antibody 1 (anti-CD200 antibody IgG2a with effector function) | 5 mg/kg |
| Group 3 | 8 | Antibody 1 (anti-CD200 antibody IgG2a with effector function) | 1 mg/kg |
| Group 4 | 8 | Antibody 2 (anti-CD200 antibody that does not possess effector function) | 5 mg/kg |
| Group 5 | 8 | Control antibody (IgG2a) that does not bind to CD200 but possesses effector function | 5 mg/kg |
| Group 6 | 6 | Non-immunized, non-treated control group | N/A |

N refers to the number of mice in each group.
N/A = not applicable.

Figure 11:
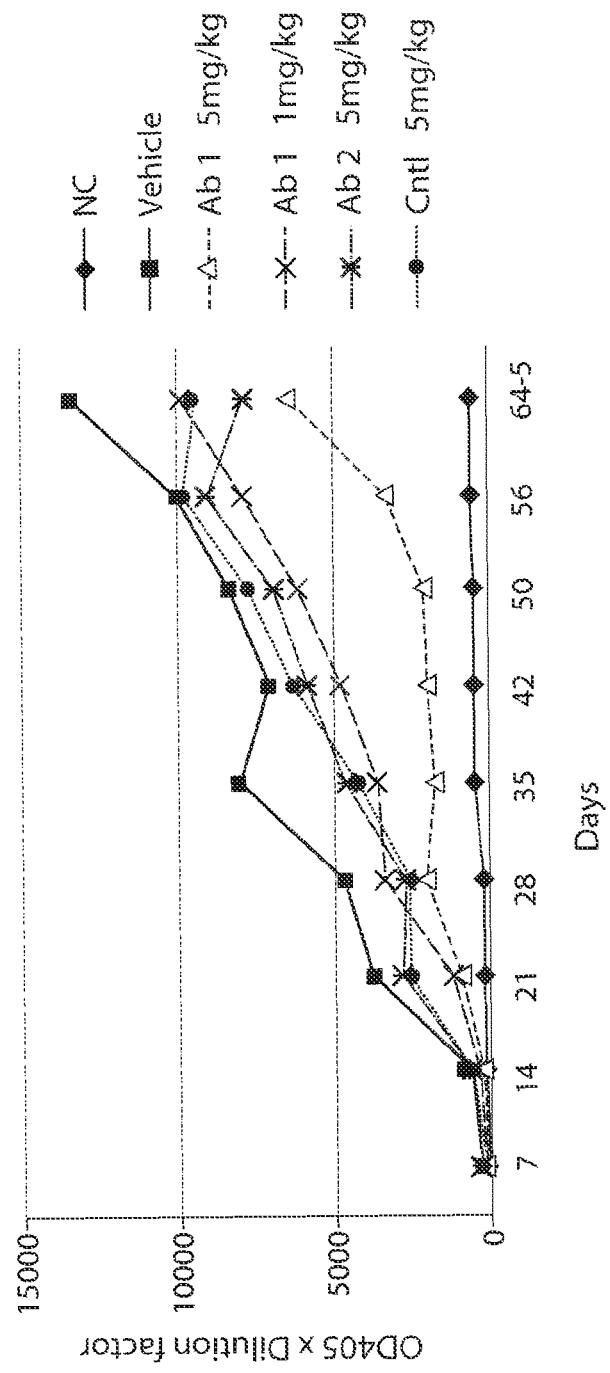
FIG. 11 is a line graph depicting the effect of an anti-CD200 antibody on anti-RBC antibody titer in a mouse model of autoimmune hemolytic disease. C57BL/6 mice were administered $2\times10^8$ rat RBCs intraperitoneally (i.p.) once on study day 0 and then once per week thereafter for the remainder of the study. The rat RBC-immunized mice were then treated with an anti-CD200 antibody that possessed effector function (Antibody 1; Ab 1) at 5 mg/kg or 1 mg/kg; an anti-CD200 antibody that did not possess effector function (Antibody 2; Ab 2) at 5 mg/kg; or a control antibody (Cntl) at 5 mg/kg. A group of mice was also treated with vehicle only. A final group of mice received no immunization or antibody treatment (NC). The Y-axis depicts the relative fluorescence intensity reflected as the OD405× serum dilution factor and the X-axis represents the number of days following the start of the study.

On a weekly basis, blood was drawn from the mice of Groups 1 to 6 prior to, during, and after the above treatments to evaluate by flow cytometry whether treatment affected the titer of anti-mouse RBC autoantibodies and/or anti-rat RBC alloantibodies in the mice. On day 64 or 65 of the study, the mice were sacrificed and their spleens harvested. (Four mice in each group were sacrificed on day 64 and the other four mice in each group were sacrificed on day 65). To determine the relative concentration of alloantibodies produced in a subject mouse (e.g., a treated mouse from Group 3), serum obtained from the mouse was contacted to a sample of isolated rat RBCs for a time and under conditions sufficient for any rat RBC-specific alloantibodies present in the serum to bind to the rat RBCs. The cells were washed with PBS and then incubated with a fluorescently-labeled antibody that binds to mouse antibodies. Following an additional washing step, the cells were subjected to flow cytometry to evaluate the relative amount of mouse anti-rat RBCs bound to the rat RBCs as the mean fluorescence intensity. As shown in FIG. 11, sera obtained from mice of Groups 1, 3, 4, and 5 contained an increasing concentration of anti-rat RBC alloantibodies over the course of the experiment. In contrast, sera obtained from the mice of Group 2 post-treatment contained much less detectable anti-rat RBC alloantibodies as compared to the other Groups. These results further indicated that Antibody 1, an anti-CD200 antibody, at 5 mg/kg was capable of reducing the titer of RBC-specific alloantibodies produced in a mouse model of autoimmune hemolytic disease.

Study 3 (Treatment Model).

Therapeutic anti-CD200 antibodies were tested for their ability to treat autoimmune hemolytic disease using a mouse model of the disease. To elicit in mice the production of autoantibodies that bind to mouse red blood cells (RBCs), rat RBCs were administered intraperitoneally (i.p.) to female C57BL/6 mice once on study day 0 and then once per week thereafter for the remainder of the study. As described above, production of anti-rat RBC alloantibodies by the immunized mice was observed by the second week of the study and production by the mice of anti-mouse RBC autoantibodies was observed by week three. The rat RBC-immunized mice were divided into three groups designated Group 1 (6 mice), Group 2 (3 mice), and Group 3 (5 mice).

Starting on day 86, the mice of each of Groups 1 to 3 received an additional treatment of 10 doses of a therapeutic agent or vehicle control administered under the following schedule: (i) five doses of agent or vehicle administered as one dose per day for five consecutive days; (ii) a two day break in treatment; and (iii) an additional five doses of the agent or vehicle administered one dose per day for five consecutive days. Group 1 mice were treated under the aforementioned treatment schedule with Antibody 1—an anti-CD200 antibody (IgG2a) having effector function—each dose being 5 mg/kg. Group 2 mice were treated with Antibody 1 at a dose of 1 mg/kg. Group 3 mice were treated under the above treatment schedule with Antibody 2—an anti-CD200 antibody that lacked effector function—each dose at 5 mg/kg. The Group design and treatment schedules for each group are summarized in Table 5.

TABLE 5

Group Design and Treatment Schedule for Study 3.

| Groups | N | Therapeutic Administered | Dose |
|---|---|---|---|
| Group 1 | 6 | Antibody 1 (anti-CD200 antibody IgG2a with effector function) | 5 mg/kg |
| Group 2 | 3 | Antibody 1 (anti-CD200 antibody IgG2a with effector function) | 1 mg/kg |
| Group 3 | 5 | Antibody 2 (anti-CD200 antibody that does not possess effector function) | 5 mg/kg |
| Group 4 | 3 | Non-immunized, non-treated control group | N/A |

N refers to the number of mice in each group.
N/A = not applicable.

At the conclusion of the study, the mice were sacrificed and their spleens harvested. To determine whether administration of Antibody 1 to the mice affected activation of splenocytes by RBC, in addition to affecting the production of anti-RBC antibodies in the mice, splenocyte activation in the presence of RBCs was evaluated using an in vitro proliferation assay. Briefly, isolated splenocytes were cultured with one of three different antigens—mouse RBCs, rat RBCs, or bovine serum albumin (control)—or with media alone. Following contact of the splenocytes with the antigens, $^3$H-thymidine was added to the splenocyte culture medium for approximately 16 hours. The medium was removed and the cells harvested. The relative activation of the splenocytes by the antigens was then measured as a function of the amount of $^3$H-thymidine incorporated into the DNA of the splenocytes.

Figure 12:
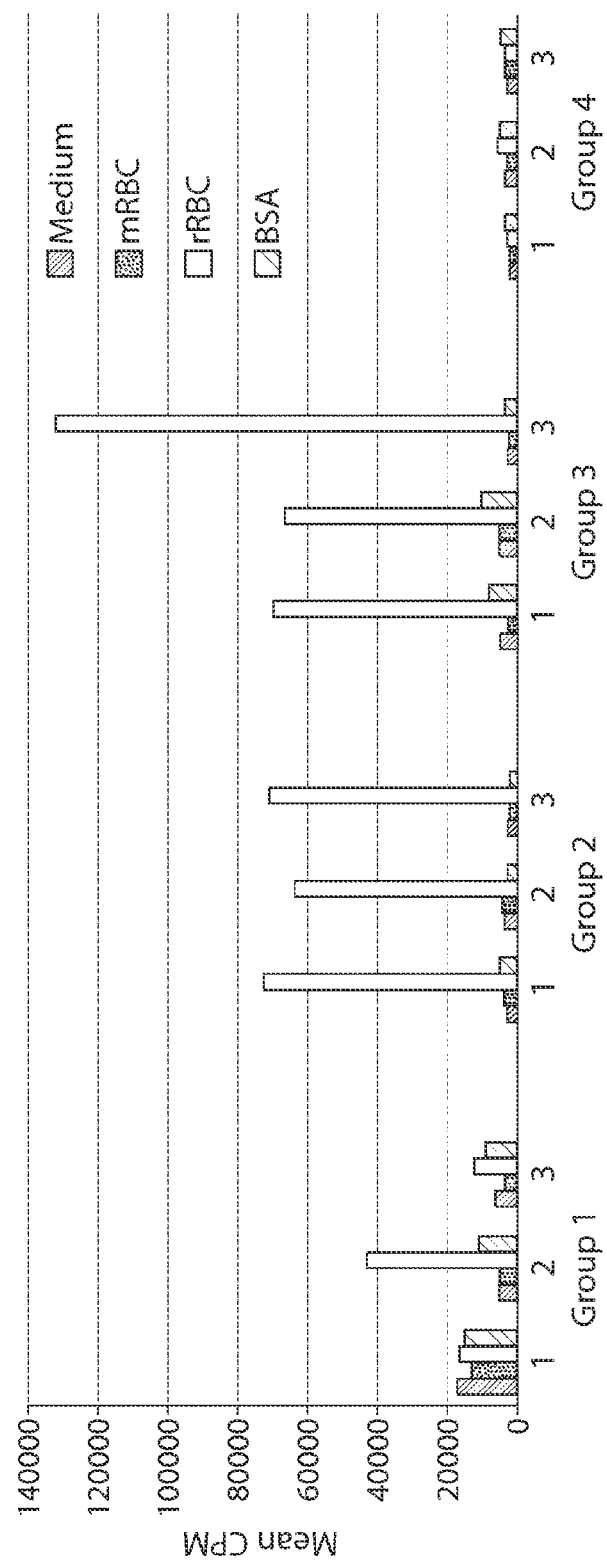
FIG. 12 is a bar graph depicting the reduction in antigen-induced proliferation of splenocytes isolated from mice treated with an anti-CD200 antibody. The Y-axis represents the mean counts per minute of $^3$H-thymidine radioactivity in nucleic acid isolated from each cell population. The X-axis represents individual mice, three (3) depicted in each group. For each mouse, the four measurements are for proliferation of splenocytes induced by medium alone, mouse red blood cells (mRBC), rat red blood cells (rRBC), or bovine serum albumin (BSA). The mice of Group 1 were treated with an anti-CD200 antibody with effector function (Antibody 1) at a dose of 5 mg/kg. The mice of Group 2 were treated with Antibody 1 at a dose of 1 mg/kg. The mice of Group 3 were treated with a control antibody that does not bind to CD200 and the mice of Group 4 were not treated with an antibody or immunized with the rat red blood cells.

As shown in FIG. 12, splenocytes from Group 2 and 3 mice exhibited a robust proliferative response following contact with rat RBCs. In contrast, splenocytes from Group 1 mice proliferated very little in the presence of rat RBCs indicating that administration of an anti-CD200 antibody at 5 mg/kg was capable of inhibiting the activation of splenocytes by rat RBCs in a mouse model of autoimmune hemolytic disease.

Study 4 (Treatment Model).

As described above, to elicit in mice the production of autoantibodies that bind to mouse red blood cells (RBCs), rat RBCs were administered intraperitoneally (i.p.) to female C57BL/6 mice once on study day 0 and then once per week thereafter for the remainder of the study.

The rat RBC-immunized mice were divided into seven (7) groups designated Group 1, Group 2, Group 3, Group 4, Group 5, Group 6, and Group 7. An eighth group of mice (designated Group 8) was also evaluated as a control. The Group 8 mice were neither immunized with rat RBCs nor did they receive any of the additional treatments described below. Ten mice were in each group.

Starting on day 21, the mice of each of Groups 1 to 7 received an additional treatment of one or more therapeutic agents or vehicle control administered under the following schedule: for each week of the study, five doses of one or more agents or vehicle administered as one dose per day for five consecutive days. Group 1 mice were treated with only vehicle-phosphate-buffered saline (PBS). Group 2 mice were treated under the above treatment schedule using a dose of 5 mg/kg of a Control antibody that does not bind to CD200, but possesses effector function (IgG2a). Group 3 mice were treated under the aforementioned treatment schedule with Antibody 1—an anti-CD200 antibody (IgG2a) having effector function—each dose being 5 mg/kg. Group 4 mice were treated under the above schedule with 15 mg/kg cyclosporine. Group 5 mice were treated under the above dosing schedule with both the Control antibody (at 5 mg/kg) and cyclosporine (at 15 mg/kg). Group 6 mice were treated under the above dosing schedule with both Antibody 1 (at 5 mg/kg) and cyclosporine (at 15 mg/kg). Group 7 mice were treated under the above dosing schedule with both Antibody 1 (at 1 mg/kg) and cyclosporine (at 15 mg/kg). The Group design and treatment schedules for each group are summarized in Table 6.

TABLE 6

Group Design and Treatment Schedule for Study 4.

| Groups | N | Therapeutic Administered | Dose |
|---|---|---|---|
| Group 1 | 10 | Vehicle | N/A |
| Group 2 | 10 | Control antibody (IgG2a) that does not bind to CD200 but possesses effector function | 5 mg/kg |
| Group 3 | 10 | Antibody 1 (anti-CD200 antibody IgG2a with effector function) | 5 mg/kg |
| Group 4 | 10 | Cyclosporine | 15 mg/kg |
| Group 5 | 10 | Control antibody; and cyclosporine | 5 mg/kg 15 mg/kg |
| Group 6 | 10 | Antibody 1; and cyclosporine | 5 mg/kg 15 mg/kg |
| Group 7 | 10 | Antibody 1; and cyclosporine | 1 mg/kg 15 mg/kg |
| Group 8 | 10 | Non-immunized, non-treated control group | N/A |

N refers to the number of mice in each group.
N/A = not applicable.

On a weekly basis, blood was drawn from the mice of Groups 1 to 8 prior to, during, and after the above treatments to evaluate by flow cytometry whether treatment affected the titer of anti-mouse RBC autoantibodies and/or anti-rat RBC alloantibodies in the mice. On day 37 of the study, the mice were sacrificed and their spleens harvested. Bone marrow cells were also obtained from the two mouse femur and tibia bones. The spleen and bone marrow cells were subjected to flow cytometry as described below (Example 5).

A reduced concentration of anti-rat RBC alloantibodies was present in post-treatment sera obtained from mice of Groups 3 and 4 as compared to the corresponding pre-treatment sera. The post-treatment reduction in anti-rat RBC alloantibodies was even greater in the mice of Groups 6 and 7, indicating that cyclosporine and Antibody 1 have a synergistic effect on reducing alloantibody production in the mice. These results even further indicated that an anti-CD200 antibody was capable of reducing the titer of RBC-specific antibodies produced in a mouse model of autoimmune hemolytic disease and that an anti-CD200 antibody is useful for treating the disease.

Example 5

Figure 13:
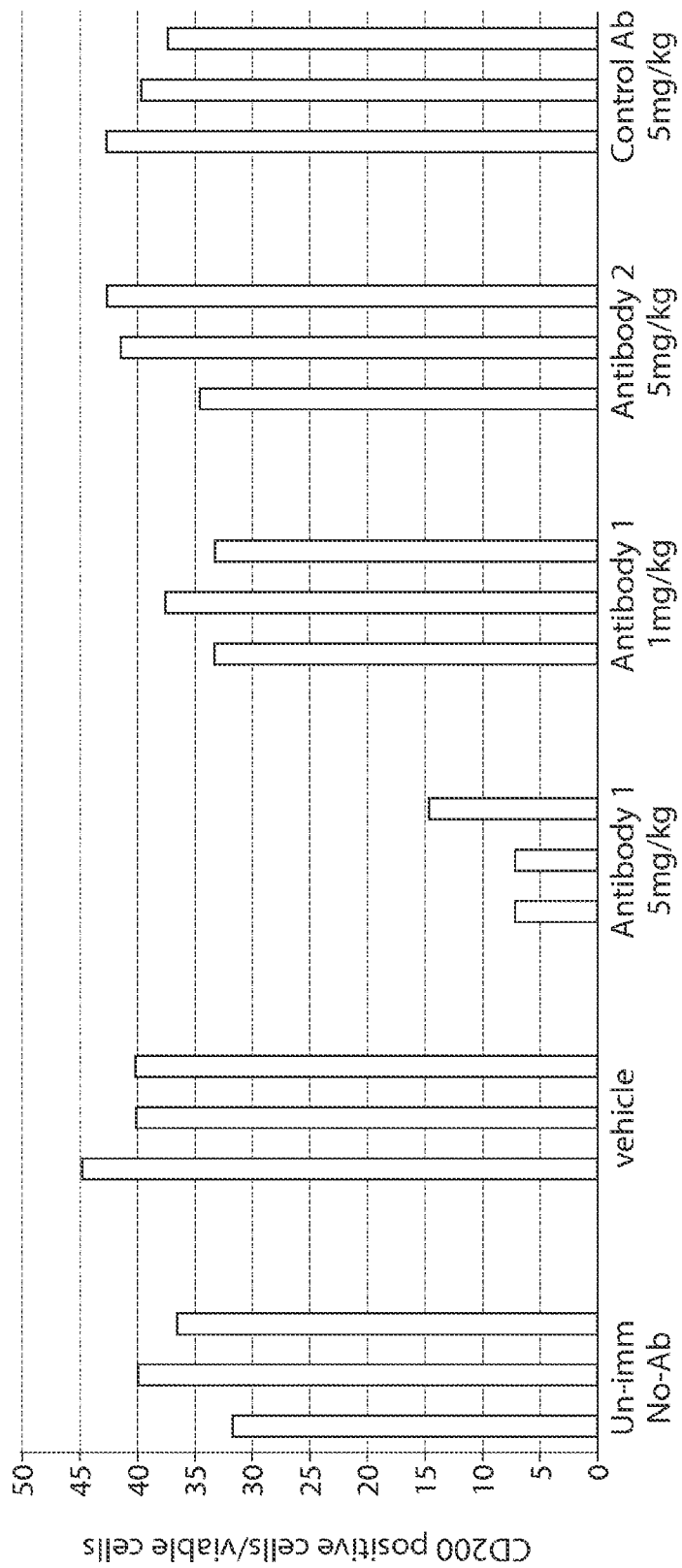
FIG. 13 is a bar graph depicting the reduction in CD200+ splenocytes in mice treated with an anti-CD200 antibody. C57BL/6 mice were administered $2\times10^8$ rat RBCs intraperitoneally (i.p.) once on study day 0 and then once per week thereafter for the remainder of the study. The rat RBC-immunized mice were then treated with an anti-CD200 antibody that possessed effector function (Antibody 1; Ab 1) at 5 mg/kg or 1 mg/kg; an anti-CD200 antibody that did not possess effector function (Antibody 2; Ab 2) at 5 mg/kg; or a control antibody (Cntl) at 5 mg/kg. A group of mice was also treated with vehicle only. A final group of mice received no immunization or antibody treatment (Un-imm, No-Ab). The Y-axis represents the percentage of CD200+ cells in the total population of viable splenocytes. The X-axis represents individual mice, three (3) depicted in each group.

Administration of an Anti-CD200 Antibody to Mice Affects the Concentration of Splenocyte and Bone Marrow Cell Populations in the Mice Splenocytes obtained from the mice of Study 1 were evaluated to determine the percentage of cells that express CD200. Cells were harvested from the spleens of the mice and incubated with a composition of biotin-labeled anti-CD200 antibodies (polyclonal) for an amount of time and under conditions sufficient to allow for binding of the antibodies to CD200, if present on the cells. The polyclonal antibody preparation was used to prevent or lessen any masking effect due to the presence of residual therapeutic anti-CD200 antibody (e.g., Antibody 1 or Antibody 2) on the cells. The cells were washed and incubated with a fluorescently-labeled streptavidin moiety. Following an additional washing step, the cells were then subjected to flow cytometry. As shown in FIG. 13, there was a marked reduction in the concentration of $CD200^+$ splenocytes in mice treated with fourteen 5 mg/kg doses of Antibody 1 as compared to the concentration of CD200+ splenocytes in mice treated with vehicle, the Control antibody, or Antibody 2.

Splenocytes harvested from the spleens of the mice of Study 2 were also subjected to staining and flow cytometry analysis as described above. There was a marked reduction in the concentration of $CD200^+$ splenocytes in mice chronically treated with 5 mg/kg of Antibody 1, as compared to the concentration of $CD200^+$ splenocytes in mice treated with vehicle or the Control antibody. There was also no change in the concentration of $CD200^+$ splenocytes in the Group 3 mice treated with 1 mg/kg dose of Antibody 1 and Group 4 mice trated with 5 mg/kg Antibody 2.

Splenocytes harvested from the spleens of the mice of Study 4 were also subjected to staining and flow cytometry analysis as described above. There was a marked reduction in the concentration of $CD200^+$ splenocytes in mice treated with 5 mg/kg of Antibody 1 with or without cyclosporine, as compared to the concentration of $CD200^+$ splenocytes in mice treated with vehicle, the Control antibody, cyclosporine alone, or a combination of the Control antibody and cyclosporine. There was also no change in the concentration of $CD200^+$ splenocytes in the Group 7 mice treated with a combination schedule of cyclosporine and a 1 mg/kg dose of Antibody 1. An analysis of the mean fluorescence intensity (MFI) of the $CD200^+$ splenocytes from each mouse (which is a measure of the relative expression level of CD200 by each $CD200^+$ splenocyte) was also performed. The MFI of $CD200^+$ splenocytes from Groups 3 and 6 was markedly reduced as compared to the MFI of $CD200^+$ splenocytes in the remaining Groups (save Group 8). This indicated that not only does administration of Antibody 1 to the mice reduce the total number of $CD200^+$ splenocytes, but the remaining cells that do express $CD200^+$ in Antibody 1-treated mice express CD200 at much lower levels.

Taken together, these results confirm that administration of an anti-CD200 antibody to an animal reduces the concentration of $CD200^+$ splenocytes in the animal. The results also indicate that the anti-CD200 antibody-mediated reduction in $CD200^+$ splenocytes is neither positively nor negatively affected by cyclosporine.

The inventors also further examined the effect of anti-CD200 antibodies on: (i) the concentration of particular $CD200^+$ lymphocyte subsets of splenocytes from the mice of Study 4 and (ii) the concentration of particular CD200+ subsets of bone marrow-derived cells from the mice of Study 4.

Concentration of Splenic Lymphocyte Subsets in the Mice of Study 4

$CD3^+/CD200^+$ Lymphocyte Subset.

A sample of splenocytes from each of the mice of Study 4 was incubated with the polyclonal anti-CD200 antibody preparation and a detectably-labeled antibody that binds to CD3 to thereby identify the proportion of $CD3^+/CD200^+$ cells in the spleens of mice from Groups 1 to 8. The $CD3^+$ population of cells includes T cells such as $CD4^+$ and $CD8^+$ T cells. The labeled cells were subjected to flow cytometry. There was a marked reduction in the concentration of $CD3^+/CD200^+$ splenocytes in mice chronically treated with 5 mg/kg of Antibody 1 with or without cyclosporine, as compared to the concentration of $CD3^+/CD200^+$ splenocytes in mice treated with vehicle, the Control antibody, cyclosporine alone, or a combination of the Control antibody and cyclosporine. There was also no significant change in the concentration of $CD3^+/CD200^+$ splenocytes in the Group 7 mice treated with a combination schedule of cyclosporine and a 1 mg/kg dose of Antibody 1.

$CD5^+/CD200^+$ Lymphocyte Subset.

A sample of splenocytes from each of the mice of Study 4 was incubated with the polyclonal anti-CD200 antibody preparation and a detectably-labeled antibody that binds to CD5 to thereby identify the proportion of $CD5^+/CD200^+$ cells in the spleens of mice from Groups 1 to 8. The $CD5^+$ population of cells includes T cells as well as B cells (the B1 cell population). The labeled cells were subjected to flow cytometry. There was a marked reduction in the concentration of $CD5^+/CD200^+$ splenocytes in mice chronically treated with 5 mg/kg of Antibody 1 with or without cyclosporine, as compared to the concentration of $CD5^+/CD200+$ splenocytes in mice treated with vehicle, the Control antibody, cyclosporine alone, or a combination of the Control antibody and cyclosporine. There was also no significant change in the concentration of $CD5^+/CD200+$ splenocytes in the Group 7 mice treated with a combination schedule of cyclosporine and a 1 mg/kg dose of Antibody 1.

$CD19^+/CD200^+$ Lymphocyte Subset.

A sample of splenocytes from each of the mice of Study 4 was incubated with the polyclonal anti-CD200 antibody preparation and a detectably-labeled antibody that binds to CD19 to thereby identify the proportion of $CD19^+/CD200^+$ cells in the spleens of mice from Groups 1 to 8. The $CD19^+$ population of cells includes B cells. The labeled cells were subjected to flow cytometry. Like $CD5^+/CD200^+$ cells and $CD3^+/CD200+$ cells, there was also a marked reduction in the concentration of $CD19^+/CD200^+$ splenocytes in mice chronically treated with 5 mg/kg of Antibody 1 with or without cyclosporine, as compared to the concentration of $CD19^+/CD200^+$ splenocytes in mice treated with vehicle, the Control antibody, cyclosporine alone, or a combination of the Control antibody and cyclosporine. There was also no significant change in the concentration of $CD19^+/CD200^+$ splenocytes in the Group 7 mice treated with a combination schedule of cyclosporine and a 1 mg/kg dose of Antibody 1.

$CD138^+/CD200^+$ Lymphocyte Subset.

A sample of splenocytes from each of the mice of Study 4 was incubated with the polyclonal anti-CD200 antibody preparation and a detectably-labeled antibody that binds to CD138 to thereby identify the proportion of $CD138^+/CD200^+$ cells in the spleens of mice from Groups 1 to 8. The $CD138^+$ population of cells includes plasma cells. The labeled cells were subjected to flow cytometry. There was a marked reduction in the concentration of $CD138^+/CD200^+$ splenocytes in mice chronically treated with 5 mg/kg of Antibody 1 with or without cyclosporine, as compared to the concentration of $CD138^+/CD200^+$ splenocytes in mice treated with vehicle, the Control antibody, cyclosporine alone, or a combination of the Control antibody and cyclosporine. There was also no significant change in the concentration of $CD138^+/CD200^+$ splenocytes in the Group 7 mice treated with a combination schedule of cyclosporine and a 1 mg/kg dose of Antibody 1.

$F4/80^+$ Lymphocyte Subset.

F4/80 is 125 kDa transmembrane protein present on the cell-surface of mature mouse macrophages. To determine whether administration of an anti-CD200 antibody affects the concentration of resident macrophages in spleen, a sample of splenocytes from each mouse of Study 4 was incubated with a detectably-labeled antibody that binds to F4/80. The labeled cells were subjected to flow cytometry to thereby identify the proportion of $F4/80^+$ cells in the spleens of mice from Groups 1 to 8. The concentration of $F4/80^+$ splenocytes increased in mice treated with 5 mg/kg of Antibody 1 (10 doses) with or without cyclosporine, as compared to the concentration of $F4/80^+$ splenocytes in mice treated with vehicle, the Control antibody, cyclosporine alone, or a combination of the Control antibody and cyclosporine. There was also no significant change in the concentration of $F4/80^+$ splenocytes in the Group 7 mice treated with a combination schedule of cyclosporine and a 1 mg/kg dose of Antibody 1.

Taken together, these results indicate that administration of an anti-CD200 antibody reduces a variety of $CD200^+$ splenocyte subsets, but increases certain macrophage subsets, in the treated animals.

Concentration of Bone Marrow Cell Subsets in the Mice of Study 4

$CD34^+/CD200^+$ Bone Marrow Cell Subset.

A sample of bone marrow cells from each of the mice was incubated with the polyclonal anti-CD200 antibody preparation and a detectably-labeled antibody that binds to CD34 to thereby identify the proportion of $CD34^+/CD200^+$ cells in the bone marrow of mice from Groups 1 to 8. The $CD34^+$ cells include a population of hematopoietic stem cells (HSCs). The labeled cells were subjected to flow cytometry also selecting for those cells that are lineage low ($Lin^{-/Low}$). There was a marked reduction in the concentration of $CD34^+/CD200^+$ bone marrow cells in mice treated with 5 mg/kg of Antibody 1 (10 doses) with or without cyclosporine, as compared to the concentration of $CD34^+/CD200^+$ bone marrow cells in mice treated with vehicle, the Control antibody, cyclosporine alone, or a combination of the Control antibody and cyclosporine. There was also no significant change in the concentration of $CD34^+/CD200^+$ bone marrow cells in the Group 7 mice treated with a combination schedule of cyclosporine and a 1 mg/kg dose of Antibody 1.

$Sca-1^+/CD200^+$ Bone Marrow Cell Subsets.

A sample of bone marrow cells from each of the mice was incubated with the polyclonal anti-CD200 antibody preparation and a detectably-labeled antibody that binds to Sca-1 to thereby identify the proportion of $Sca-1^+/CD200^+$ cells in the bone marrow of mice from Groups 1 to 8. The $Sca-1^+$ cells include a population of HSCs and mesenchymal stem cells (MSCs). The labeled cells were subjected to flow cytometry also selecting for those cells that are lineage low ($Lin^{-/Low}$). There was a marked reduction in the concentration of $Sca-1^+/CD200^+$ bone marrow cells in mice treated with 5 mg/kg of Antibody 1 (10 doses) with or without cyclosporine, as compared to the concentration of $Sca-1^+/CD200^+$ bone marrow cells in mice treated with vehicle, the Control antibody, cyclosporine alone, or a combination of the Control antibody and cyclosporine. There was also no significant change in the concentration of $Sca-1^+/CD200^+$ bone marrow cells in the Group 7 mice treated with a combination schedule of cyclosporine and a 1 mg/kg dose of Antibody 1.

$Sca-1^+/CD34^+$ Bone Marrow Cell Subsets.

A sample of bone marrow cells from each of the mice was incubated with a first detectably-labeled antibody that binds to CD34 and a second detectably-labeled antibody that binds to Sca-1 to thereby identify the proportion of $Sca-1^+/CD34^+$ cells in the bone marrow of mice from Groups 1 to 8. The labeled cells were subjected to flow cytometry also selecting for those cells that are lineage low ($Lin^{-/Low}$). The $Sca-1^+/CD34^+/Lin^-$ cells include a population of MSCs. There was a marked reduction in the concentration of $Sca-1^+/CD34^+$ bone marrow cells in mice treated with 5 mg/kg of Antibody 1 (10 doses) with or without cyclosporine, as compared to the concentration of $Sca-1^+/CD34^+$ bone marrow cells in mice treated with vehicle, the Control antibody, cyclosporine alone, or a combination of the Control antibody and cyclosporine. There was also no significant change in the concentration of $Sca-1^+/CD34^+$ bone marrow cells in the Group 7 mice treated with a combination schedule of cyclosporine and a 1 mg/kg dose of Antibody 1.

$c-kit^+/CD200^+$ Bone Marrow Cell Subsets.

A sample of bone marrow cells from each of the mice was incubated with the polyclonal anti-CD200 antibody preparation and a detectably-labeled antibody that binds to c-kit to thereby identify the proportion of $c-kit^+/CD200^+$ cells in the bone marrow of mice from Groups 1 to 8. The $c-kit^+$ cells include a population of HSCs and MSCs. The labeled cells were subjected to flow cytometry also selecting for those cells that are lineage low ($Lin^{-/Low}$). There was a marked reduction in the concentration of $c-kit^+/CD200^+$ bone marrow cells in mice chronically treated with 5 mg/kg of Antibody 1 with or without cyclosporine, as compared to the concentration of $c-kit^+/CD200^+$ bone marrow cells in mice treated with vehicle, the Control antibody, cyclosporine alone, or a combination of the Control antibody and cyclosporine. There was also no significant change in the concentration of $c-kit^+/CD200^+$ bone marrow cells in the Group 7 mice treated with a combination schedule of cyclosporine and a 1 mg/kg dose of Antibody 1.

$CD200^+/CD200R^+$ Bone Marrow Cell Subset.

A sample of bone marrow cells from each of the mice was incubated with the polyclonal anti-CD200 antibody preparation and a detectably-labeled antibody that binds to CD200R to thereby identify the proportion of $CD200^+/CD200R^+$ cells in the bone marrow of mice from Groups 1 to 8. The labeled cells were subjected to flow cytometry. There was a marked reduction in the concentration of $CD200^+/CD200R^+$ bone marrow cells in mice chronically treated with 5 mg/kg of Antibody 1 with or without cyclosporine, as compared to the concentration of $CD200^+/CD200R^+$ bone marrow cells in mice treated with vehicle, the Control antibody, cyclosporine alone, or a combination of the Control antibody and cyclosporine. There was also no significant change in the concentration of $CD200"/CD200R^+$ bone marrow cells in the Group 7 mice treated with a combination schedule of cyclosporine and a 1 mg/kg dose of Antibody 1.

Example 6

Recovery of Bone Marrow Cell and CD200+ Splenocyte Subsets after Withdrawal of Anti-CD200 Therapy Study 5 (Treatment Model).

The therapeutic anti-CD200 antibodies were again tested for their ability to modulate the concentration of specific subset populations of splenocytes and bone marrow cells. The antibodies were administered to the mice in the context of a mouse model of autoimmune hemolytic disease. As described above, to elicit in mice the production of autoantibodies that bind to mouse red blood cells (RBCs), $2 \times 10^8$ rat RBCs were administered intraperitoneally (i.p.) to female BALB/c mice once on study day 0 and then once per week thereafter for the remainder of the study. Production of anti-rat RBC alloantibodies by the immunized mice was observed by the second week of the study and production by the mice of anti-mouse RBC autoantibodies was observed by week three.

The rat RBC-immunized mice were divided into five groups designated Group 2 (20 mice), Group 3 (20 mice), Group 4 (20 mice), Group 5 (15 mice), and Group 6 (15 mice). A sixth group of mice (designated Group 1; 20 mice) was also evaluated as a control. The Group 1 mice were neither immunized with rat RBCs nor did they receive any of the additional treatments described below.

Starting on day 21, the mice of each of Groups 2 to 6 received an additional treatment of 10 doses of a therapeutic agent or vehicle control administered under the following schedule: (i) five doses of agent or vehicle administered as one dose per day for five consecutive days; (ii) a two day break in treatment; and (iii) an additional five doses of the agent or vehicle administered one dose per day for five consecutive days. Group 6 mice were treated with only vehicle-phosphate-buffered saline (PBS). Group 2 mice were treated under the aforementioned treatment schedule with Antibody 1—an anti-CD200 antibody (IgG2a) having effector function—each dose being 5 mg/kg. Group 3 mice were treated under the above treatment schedule with Antibody 2—an anti-CD200 antibody that lacked effector function—each dose at 5 mg/kg. Group 4 mice were treated under the above treatment schedule using a dose of 5 mg/kg of a Control antibody that does not bind to CD200, but possesses effector function (IgG2a). Group 5 mice were treated under the above treatment schedule using a dose of 5 mg/kg of a Control antibody that does not bind to CD200 and does not possess effector function. The Group design and treatment schedules for each group are summarized in Table 7.

TABLE 7

Group Design and Treatment Schedule for Study 5.

| Groups | N | Therapeutic Administered | Dose |
| --- | --- | --- | --- |
| Group 1 | 20 | Non-immunized, non-treated control group | N/A |
| Group 2 | 20 | Antibody 1 (anti-CD200 antibody IgG2a with effector function) | 5 mg/kg |
| Group 3 | 20 | Antibody 2 (anti-CD200 antibody that does not possess effector function) | 5 mg/kg |
| Group 4 | 20 | Control antibody (IgG2a) that does not bind to CD200 but possesses effector function | 5 mg/kg |
| Group 5 | 15 | Control antibody (IgG2a) that does not bind to CD200 and does not possess effector function | 5 mg/kg |
| Group 6 | 15 | Vehicle | N/A |

N refers to the number of mice in each group.
N/A = not applicable.

On a weekly basis, blood was drawn from the mice of Groups 1 to 6 prior to, during, and after the above treatments to evaluate by flow cytometry whether treatment affected the titer of anti-mouse RBC autoantibodies and/or anti-rat RBC alloantibodies in the mice. On day 35 of the study, three of the mice in each group were sacrificed and their spleens harvested. Bone marrow was also isolated from the femurs and tibias of each mouse. As described above, the cells were labeled with detectably-labeled antibodies (e.g., the polyclonal anti-CD200 antibody preparation and an additional fluorescently-labeled antibody) and subjected to flow cytometry. A summary of the results are shown below in Table 8.

TABLE 8

Effect of Anti-CD200 Antibodies on Splenocyte and Bone Marrow Cell Subsets at day 35

| Tissue Type | Cell Subset/Expression Profile | Reduction (R) or Increase (I) in Group 2 Mice** | Reduction (R) or Increase (I) in Group 3 Mice** |
| --- | --- | --- | --- |
| Spleen | $CD200^+$ | R | R |
| Spleen | $CD3^+/CD200^+$ | R | — |
| Spleen | $CD5^+/CD200^+$ | R | — |
| Spleen | $CD19^+/CD200^+$ | R | — |
| Spleen | $CD45R^+/CD200^+$ | R | — |
| Spleen | $CD138^+/CD200^+$ (Gated on $CD45R^+$ cells) | R | R |
| Spleen | $CD200^+$ (Gated on $CD45R^+$ cells) | R | R* |
| Bone Marrow | $CD200^+$ | R | — |
| Bone Marrow | $CDIgk^+/CD200^+$ | R | — |
| Bone Marrow | $CD200^+$ (Gated on $CD45R^+$ cells) | R | — |
| Bone Marrow | $CD200^+$ (Gated on $CD138^+/CD45R^-$ cells) | R | — |
| Bone Marrow | $c\text{-}kit^+/CD200^+$ (Gated on $Lin^-$ cells) | R | R |

*indicates that the reduction in concentration of a particular cell subset in mice treated with Antibody 2 is not as profound as the reduction observed in the same cell subset in mice treated with Antibody 1.
**indicates that the reduction or increase in the concentration of a particular cell subset is relative the concentration of the particular subset in vehicle treated mice (Group 6) and the corresponding isotype control. Thus, the reduction of $CD200^+$ splenocytes observed in mice of Group 2 mice is relative to the concentration of $CD200^+$ splenocytes in Group 6 mice and Group 4 mice.
"—" indicates that no difference in the levels was observed between Antibody 2 and its corresponding Control antibody.

From day 35 to day 91, the remaining mice in each group received additional RBC immunizations but no treatments with the antibodies, the purpose being to determine if the populations of splenocytes and bone marrow cells would recover over time. Three mice in each group were sacrificed at day 91 and their spleens and bone marrow harvested as described above. Flow cytometry analysis was performed on the isolated cells to determine whether particular population subsets of splenocytes and bone marrow cells, which were reduced at day 35, recovered by day 91. Each of the cell populations recovered fully by day 91, indicating that the immunomodulatory effects of the anti-CD200 antibody on the concentration of bone marrow cell and splenocyte subsets is reversible upon withdrawal of the antibody.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating a human afflicted with a cancer, the method comprising administering to the human an anti-CD200 antibody or antigen-binding fragment thereof in an amount and with a frequency sufficient to produce a change in one or more anti-CD200 antibody-associated biomarkers in the human to thereby treat the human's cancer, wherein the change in one or more biomarkers is selected from the group consisting of:

(a) a reduction in the concentration of CD200⁺ T cells in a biological sample obtained from the patient after administration of the antibody or antigen-binding fragment thereof, as compared to the concentration of CD200⁺ T cells in a control sample, (b) a reduction in the level of expression of CD200 by T cells in a biological sample obtained from the patient after administration of the antibody or antigen-binding fragment thereof, as compared to a control expression level of CD200 by T cells of the same histological type in a control sample, (c) an increase in the concentration of CD200R⁺ leukocytes in a biological sample obtained from the patient after administration of the antibody or antigen-binding fragment thereof, as compared to the concentration of CD200R⁺ leukocytes in a control sample, (d) an increase in the level of expression of CD200R by leukocytes in a biological sample obtained from the patient after administration of the antibody or antigen-binding fragment thereof, as compared to a control expression level of CD200R by leukocytes of the same histological type in a control sample, (e) a reduction in the concentration of regulatory T cells in a biological sample obtained from the patient after administration of the antibody or antigen-binding fragment thereof, as compared to the concentration of regulatory T cells of the same histological type in a control sample, (f) an increase in the concentration of activated T cells in a biological sample obtained from the patient after administration of the antibody or antigen-binding fragment thereof, as compared to the concentration of activated T cells of the same histological type in a control sample, (g) a ratio of percent activated T cells to percent regulatory T cells of at least 2:1 in a biological sample obtained from the patient after administration of the antibody or antigen-binding fragment thereof, (h) an increase in the ratio of percent activated T cells to percent regulatory T cells in a biological sample obtained from the patient after administration of the antibody or antigen-binding fragment thereof, as compared to the corresponding ratio in a control sample, (i) a reduction in the concentration of one or more subsets of CD200⁺ bone marrow cells in a biological sample obtained from the patient after administration of the antibody or antigen-binding fragment thereof, as compared to the concentration of one or more subsets of CD200⁺ bone marrow cells of the same histological type in a control sample, (j) a reduction in the concentration of one or more subsets of CD200⁺ leukocytes in a biological sample obtained from the patient after administration of the antibody or antigen-binding fragment thereof, as compared to the concentration of one or more subsets of CD200⁺ leukocytes of the same histological type in a control sample, and (k) a reduction in the level of expression of CD200 by one or more subsets of bone marrow cells in a biological sample obtained from the patient after administration of the antibody or antigen-binding fragment thereof, as compared to a control expression level of CD200 by bone marrow cells of the same histological type in a control sample.

2. The method according to claim 1, wherein:

(a) less than two months prior to administration of the anti-CD200 antibody or antigen-binding fragment thereof, the patient has not been administered a chemotherapeutic agent or an immunosuppressive agent; or (b) the patient is not infected with HIV.

3. The method according to claim 1, wherein the cancer is chronic lymphocytic leukemia (CLL).

4. The method according to claim 1, wherein the cancer is a solid tumor.

5. The method according to claim 4, wherein the solid tumor is a colon cancer, a breast cancer, a lung cancer, a renal cancer, a pancreatic cancer, a thyroid cancer, a skin cancer, a cancer of the nervous system, a cervical cancer, an ovarian cancer, a testicular cancer, a head and neck cancer, a cancer of the eye, a stomach cancer, or a liver cancer.

6. The method according to claim 5, wherein the cancer of the nervous system is a neuroblastoma.

7. The method according to claim 1, wherein the per-dose amount of the anti-CD200 antibody or antigen-binding fragment thereof administered to the patient is at least: (i) 100 mg/m² of the patient; (ii) 200 mg/m² of the patient; or (iii) 400 mg/m² of the patient.

8. The method according to claim 1, wherein the anti-CD200 antibody or an antigen-binding fragment thereof is administered to the patient at least once every two weeks.

9. The method according to claim 1, wherein the anti-CD200 antibody is a murine antibody, a chimeric antibody, a humanized antibody, or a human antibody.

10. The method according to claim 1, wherein the antigen-binding fragment is selected from the group consisting of an Fab, an F(ab')₂, an Fv, and a single-chain antibody.

11. The method according to claim 1, wherein the anti-CD200 antibody or antigen-binding fragment thereof comprises a variant constant region that has decreased or no effector function, relative to a non-variant form of the constant region.

12. The method according to claim 1, wherein the anti-CD200 antibody or antigen-binding fragment thereof inhibits the interaction between CD200 and CD200R.

13. The method according to claim 1, wherein the anti-CD200 antibody or antigen-binding fragment thereof comprises:

(i) a heavy chain CDR1 (HCDR1) comprising the amino acid sequence: GFTFSGFAMS (SEQ ID NO:4); a heavy chain CDR2 (HCDR2) comprising the amino acid sequence: SISSGGTTYYLDSVKG (SEQ ID NO:5); a heavy chain CDR3 (HCDR3) comprising the amino acid sequence: GNYYSGTSYDY (SEQ ID NO:6); a light chain CDR1 (LCDR1) comprising the amino acid sequence: RASESVDSYGNSFMH (SEQ ID NO:7); a light chain CDR2 (LCDR2) comprising the amino acid sequence: RASNLES (SEQ ID NO:8); and a light chain CDR3 (LCDR3) comprising the amino acid sequence: QQSNEDPRT (SEQ ID NO:9);

(ii) a HCDR1 comprising the amino acid sequence: GFNIKDYYMH (SEQ ID NO:10); a HCDR2 comprising the amino acid sequence: WIDPENGDTKYAPKFQG (SEQ ID NO:11); a HCDR3 comprising the amino acid sequence: KNYYVSNYNFFDV (SEQ ID NO:12); a LCDR1 comprising the amino acid sequence: SASSSVRYMY (SEQ ID NO:13); a LCDR2 comprising the amino acid sequence: DTSKLAS (SEQ ID NO:14); and a LCDR3 comprising the amino acid sequence: FQGSGYPLT (SEQ ID NO:15);

(iii) a HCDR1 comprising the amino acid sequence: GFNIKDYYIH (SEQ ID NO:16); a HCDR2 comprising the amino acid sequence: WIDPEIGATKYVPKFQG (SEQ ID NO:17); a HCDR3 comprising the amino acid sequence: LYGNYDRYYAMDY (SEQ ID NO:18); a LCDR1 comprising the amino acid sequence: KASQN-VRTAVA (SEQ ID NO:19); a LCDR2 comprising the amino acid sequence: LASNRHT (SEQ ID NO:20); and a LCDR3 comprising the amino acid sequence: LQH-WNYPLT (SEQ ID NO:21);
(iv) a HCDR1 comprising the amino acid sequence: GYS-FTDYIIL (SEQ ID NO:22); a HCDR2 comprising the amino acid sequence: HIDPYYGSSNYNLKFKG (SEQ ID NO:23); a HCDR3 comprising the amino acid sequence: SKRDYFDY (SEQ ID NO:24); a LCDR1 comprising the amino acid sequence: KASQDINSYLS (SEQ ID NO:25); a LCDR2 comprising the amino acid sequence: RANRLVD (SEQ ID NO:26); and a LCDR3 comprising the amino acid sequence: LQYDEFPYT (SEQ ID NO:27);
(v) a HCDR1 comprising the amino acid sequence: GYT-FTEYTMH (SEQ ID NO:28); a HCDR2 comprising the amino acid sequence: GVNPNNGGALYNQKFKG (SEQ ID NO:29); a HCDR3 comprising the amino acid sequence: RSNYRYDDAMDY (SEQ ID NO:30); a LCDR1 comprising the amino acid sequence: KSSQS-LLDIDEKTYLN (SEQ ID NO:31); a LCDR2 comprising the amino acid sequence: LVSKLDS (SEQ ID NO:32); and a LCDR3 comprising the amino acid sequence: WQGTHFPQT (SEQ ID NO:33); or
(vi) a HCDR1 comprising the amino acid sequence: AFNI-KDHYMH (SEQ ID NO:34); a HCDR2 comprising the amino acid sequence: WIDPESGDTEYAPKFQG (SEQ ID NO:35); a HCDR3 comprising the amino acid sequence: FNGYQALDQ (SEQ ID NO:36); a LCDR1 comprising the amino acid sequence: TASSSVSSSYLH (SEQ ID NO:37); a LCDR2 comprising the amino acid sequence: STSNLAS (SEQ ID NO:38); and a LCDR3 comprising the amino acid sequence: RQYHRSPPIFT (SEQ ID NO:39).

14. The method of claim 1, wherein the change is a reduction in the concentration of CD200$^+$T cells in a biological sample obtained from the patient after administration of the antibody or antigen-binding fragment thereof, as compared to the concentration of CD200$^+$T cells in a control sample.

15. The method of claim 1, wherein the change is a reduction in the level of expression of CD200 by T cells in a biological sample obtained from the patient after administration of the antibody or antigen-binding fragment thereof, as compared to a control expression level of CD200 by T cells of the same histological type in a control sample.

16. The method of claim 1, wherein the change is an increase in the concentration of CD200R$^+$leukocytes in a biological sample obtained from the patient after administration of the antibody or antigen-binding fragment thereof, as compared to the concentration of CD200R$^+$leukocytes in a control sample.

17. The method of claim 1, wherein the change is an increase in the level of expression of CD200R by leukocytes in a biological sample obtained from the patient after administration of the antibody or antigen-binding fragment thereof, as compared to a control expression level of CD200R by leukocytes of the same histological type in a control sample.

18. The method of claim 1, wherein the change is a reduction in the concentration of regulatory T cells in a biological sample obtained from the patient after administration of the antibody or antigen-binding fragment thereof, as compared to the concentration of regulatory T cells of the same histological type in a control sample.

19. The method of claim 1, wherein the change is an increase in the concentration of activated T cells in a biological sample obtained from the patient after administration of the antibody or antigen-binding fragment thereof, as compared to the concentration of activated T cells of the same histological type in a control sample.

20. The method of claim 1, wherein the change is a ratio of percent activated T cells to percent regulatory T cells of at least 2:1 in a biological sample obtained from the patient after administration of the antibody or antigen-binding fragment thereof.

21. The method of claim 1, wherein the change is an increase in the ratio of percent activated T cells to percent regulatory T cells in a biological sample obtained from the patient after administration of the antibody or antigen-binding fragment thereof, as compared to the corresponding ratio in a control sample.

22. The method of claim 1, wherein the change is a reduction in the concentration of one or more subsets of CD200$^+$ bone marrow cells in a biological sample obtained from the patient after administration of the antibody or antigen-binding fragment thereof, as compared to the concentration of one or more subsets of CD200$^+$bone maow cells of the same histological type in a control sample.

23. The method of claim 1, wherein the change is a reduction in the concentration of one or more subsets of CD200$^+$ leukocytes in a biological sample obtained from the patient after administration of the antibody or antigen-binding fragment thereof, as compared to the concentration of one or more subsets of CD200$^+$leukocytes of the same histological type in a control sample.

24. The method of claim 1, wherein the change is a reduction in the level of expression of CD200 by one or more subsets of bone marrow cells in a biological sample obtained from the patient after administration of the antibody or antigen-binding fragment thereof, as compared to a control expression level of CD200 by bone maow cells of the same histological type in a control sample.

* * * * *

SEQUENCE LISTING

<160> NUMBER OF SEQ ID NOS: 39

<210> SEQ ID NO 1
<211> LENGTH: 269
<212> TYPE: PRT
<213> ORGANISM: Homo sapiens

<400> SEQUENCE: 1

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Val Leu Ile Ser Ile Leu
                245                 250                 255

Leu Tyr Trp Lys Arg His Arg Asn Gln Asp Arg Glu Pro
            260                 265

<210> SEQ ID NO 2
<211> LENGTH: 294
<212> TYPE: PRT
<213> ORGANISM: Homo sapiens

<400> SEQUENCE: 2

Met Glu Arg Leu Thr Leu Thr Arg Thr Ile Gly Gly Pro Leu Leu Thr
1               5                   10                  15

Ala Thr Leu Leu Gly Lys Thr Thr Ile Asn Asp Tyr Gln Val Ile Arg
            20                  25                  30

Met Pro Phe Ser His Leu Ser Thr Tyr Ser Leu Val Trp Val Met Ala
        35                  40                  45

Ala Val Val Leu Cys Thr Ala Gln Val Gln Val Val Thr Gln Asp Glu

```
            50                  55                  60
Arg Glu Gln Leu Tyr Thr Pro Ala Ser Leu Lys Cys Ser Leu Gln Asn
 65                  70                  75                  80

Ala Gln Glu Ala Leu Ile Val Thr Trp Gln Lys Lys Ala Val Ser
                 85                  90                  95

Pro Glu Asn Met Val Thr Phe Ser Glu Asn His Gly Val Val Ile Gln
                100                 105                 110

Pro Ala Tyr Lys Asp Lys Ile Asn Ile Thr Gln Leu Gly Leu Gln Asn
                115                 120                 125

Ser Thr Ile Thr Phe Trp Asn Ile Thr Leu Glu Asp Glu Gly Cys Tyr
        130                 135                 140

Met Cys Leu Phe Asn Thr Phe Gly Phe Gly Lys Ile Ser Gly Thr Ala
145                 150                 155                 160

Cys Leu Thr Val Tyr Val Gln Pro Ile Val Ser Leu His Tyr Lys Phe
                165                 170                 175

Ser Glu Asp His Leu Asn Ile Thr Cys Ser Ala Thr Ala Arg Pro Ala
                180                 185                 190

Pro Met Val Phe Trp Lys Val Pro Arg Ser Gly Ile Glu Asn Ser Thr
                195                 200                 205

Val Thr Leu Ser His Pro Asn Gly Thr Thr Ser Val Thr Ser Ile Leu
        210                 215                 220

His Ile Lys Asp Pro Lys Asn Gln Val Gly Lys Glu Val Ile Cys Gln
225                 230                 235                 240

Val Leu His Leu Gly Thr Val Thr Asp Phe Lys Gln Thr Val Asn Lys
                245                 250                 255

Gly Tyr Trp Phe Ser Val Pro Leu Leu Leu Ser Ile Val Ser Leu Val
                260                 265                 270

Ile Leu Leu Val Leu Ile Ser Ile Leu Leu Tyr Trp Lys Arg His Arg
        275                 280                 285

Asn Gln Asp Arg Glu Pro
    290

<210> SEQ ID NO 3
<211> LENGTH: 274
<212> TYPE: PRT
<213> ORGANISM: Homo sapiens

<400> SEQUENCE: 3

Val Ile Arg Met Pro Phe Ser His Leu Ser Thr Tyr Ser Leu Val Trp
 1               5                  10                  15

Val Met Ala Ala Val Val Leu Cys Thr Ala Gln Val Gln Val Val Thr
                20                  25                  30

Gln Asp Glu Arg Glu Gln Leu Tyr Thr Thr Ala Ser Leu Lys Cys Ser
         35                  40                  45

Leu Gln Asn Ala Gln Glu Ala Leu Ile Val Thr Trp Gln Lys Lys Lys
         50                  55                  60

Ala Val Ser Pro Glu Asn Met Val Thr Phe Ser Glu Asn His Gly Val
 65                  70                  75                  80

Val Ile Gln Pro Ala Tyr Lys Asp Lys Ile Asn Ile Thr Gln Leu Gly
                 85                  90                  95

Leu Gln Asn Ser Thr Ile Thr Phe Trp Asn Ile Thr Leu Glu Asp Glu
                100                 105                 110

Gly Cys Tyr Met Cys Leu Phe Asn Thr Phe Gly Phe Gly Lys Ile Ser
            115                 120                 125
```

```
Gly Thr Ala Cys Leu Thr Val Tyr Val Gln Pro Ile Val Ser Leu His
        130                 135                 140

Tyr Lys Phe Ser Glu Asp His Leu Asn Ile Thr Cys Ser Ala Thr Ala
145                 150                 155                 160

Arg Pro Ala Pro Met Val Phe Trp Lys Val Pro Arg Ser Gly Ile Glu
                165                 170                 175

Asn Ser Thr Val Thr Leu Ser His Pro Asn Gly Thr Thr Ser Val Thr
                180                 185                 190

Ser Ile Leu His Ile Lys Asp Pro Lys Asn Gln Val Gly Lys Glu Val
            195                 200                 205

Ile Cys Gln Val Leu His Leu Gly Thr Val Thr Asp Phe Lys Gln Thr
210                 215                 220

Val Asn Lys Gly Tyr Trp Phe Ser Val Pro Leu Leu Leu Ser Ile Val
225                 230                 235                 240

Ser Leu Val Ile Leu Leu Val Leu Ile Ser Ile Leu Leu Tyr Trp Lys
                245                 250                 255

Arg His Arg Asn Gln Asp Arg Gly Glu Leu Ser Gln Gly Val Gln Lys
            260                 265                 270

Met Thr

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Gly Phe Ala Met Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ile Ser Ser Gly Gly Thr Thr Tyr Tyr Leu Asp Ser Val Lys Gly
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asn Tyr Tyr Ser Gly Thr Ser Tyr Asp Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 7

Arg Ala Ser Glu Ser Val Asp Ser Tyr Gly Asn Ser Phe Met His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Asn Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Asn Glu Asp Pro Arg Thr
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Asn Ile Lys Asp Tyr Tyr Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Asp Pro Glu Asn Gly Asp Thr Lys Tyr Ala Pro Lys Phe Gln
1               5                   10                  15

Gly

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Asn Tyr Tyr Val Ser Asn Tyr Asn Phe Phe Asp Val
1               5                   10

```
<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ala Ser Ser Ser Val Arg Tyr Met Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Ser Lys Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Gln Gly Ser Gly Tyr Pro Leu Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Asn Ile Lys Asp Tyr Tyr Ile His
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ile Asp Pro Glu Ile Gly Ala Thr Lys Tyr Val Pro Lys Phe Gln
1               5                   10                  15

Gly

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Leu Tyr Gly Asn Tyr Asp Arg Tyr Tyr Ala Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Ser Gln Asn Val Arg Thr Ala Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ala Ser Asn Arg His Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Gln His Trp Asn Tyr Pro Leu Thr
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Ser Phe Thr Asp Tyr Ile Ile Leu
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Ile Asp Pro Tyr Tyr Gly Ser Ser Asn Tyr Asn Leu Lys Phe Lys
1               5                   10                  15

Gly
```

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Lys Arg Asp Tyr Phe Asp Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Ala Ser Gln Asp Ile Asn Ser Tyr Leu Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Asn Arg Leu Val Asp
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Gln Tyr Asp Glu Phe Pro Tyr Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Thr Phe Thr Glu Tyr Thr Met His
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

```
Gly Val Asn Pro Asn Asn Gly Gly Ala Leu Tyr Asn Gln Lys Phe Lys
1               5                   10                  15

Gly

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Asn Tyr Arg Tyr Asp Asp Ala Met Asp Tyr
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ser Ser Gln Ser Leu Leu Asp Ile Asp Glu Lys Thr Tyr Leu Asn
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Val Ser Lys Leu Asp Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Gln Gly Thr His Phe Pro Gln Thr
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Phe Asn Ile Lys Asp His Tyr Met His
1               5                   10
```

```
<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Asp Pro Glu Ser Gly Asp Thr Glu Tyr Ala Pro Lys Phe Gln
1               5                   10                  15
Gly

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Asn Gly Tyr Gln Ala Leu Asp Gln
1               5

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Ser Ser Ser Val Ser Ser Ser Tyr Leu His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Thr Ser Asn Leu Ala Ser
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Gln Tyr His Arg Ser Pro Pro Ile Phe Thr
1               5                   10
```